United States Patent
Jacobson et al.

(10) Patent No.: US 10,577,368 B2
(45) Date of Patent: Mar. 3, 2020

(54) A3 ADENOSINE RECEPTOR AGONISTS

(71) Applicants: The United States of America, as represented by the Secretary, Department of Health and Human Services, Bethesda, MD (US); Saint Louis University, St. Louis, MO (US)

(72) Inventors: Kenneth A. Jacobson, Silver Spring, MD (US); Dilip K. Tosh, Rockville, MD (US); Daniela Salvemini, Chesterfield, MO (US)

(73) Assignees: The United States of America, as represented by the Secretary, Department of Health and Human Services, Bethesda, MD (US); Saint Louis University, St. Louis, MO (US)

( * ) Notice: Subject to any disclaimer, the term of this patent is extended or adjusted under 35 U.S.C. 154(b) by 38 days.

(21) Appl. No.: 15/949,701

(22) Filed: Apr. 10, 2018

(65) Prior Publication Data

US 2018/0230150 A1    Aug. 16, 2018

Related U.S. Application Data

(62) Division of application No. 15/039,778, filed as application No. PCT/US2014/066609 on Nov. 20, 2014, now Pat. No. 9,963,450.

(Continued)

(51) Int. Cl.
  *C07D 473/34*   (2006.01)
  *C07D 473/00*   (2006.01)
  *C07F 15/02*    (2006.01)

(52) U.S. Cl.
  CPC ......... *C07D 473/34* (2013.01); *C07D 473/00* (2013.01); *C07F 15/02* (2013.01)

(58) Field of Classification Search
  CPC ...... C07D 473/34; C07D 473/00; C07F 15/02
  See application file for complete search history.

(56) References Cited

U.S. PATENT DOCUMENTS 8,735,407 B2   5/2014   Jacobson et al.
8,796,291 B2   8/2014   Jacobson et al.
(Continued)

FOREIGN PATENT DOCUMENTS

WO   WO 2011/068978 A1   6/2011

OTHER PUBLICATIONS

U.S. Appl. No. 15/039,778, filed May 26, 2016.
(Continued)

*Primary Examiner* — Angela C Brown-Pettigrew
(74) *Attorney, Agent, or Firm* — Leydig, Voit & Mayer, Ltd.

(57) ABSTRACT

Disclosed are compounds of the formula (I) and (II):

(Continued)

-continued

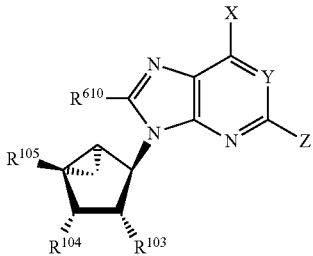
(II)

which are $A_3$ adenosine receptor agonists, pharmaceutical compositions comprising such compounds, and a method of use of these compounds, wherein X, Y, Z, $R^2$-$R^6$, and $R^{103}$-$R^{106}$ are as defined in the specification. These compounds are selective to the $A_3$ receptor, and are contemplated for use in the treatment or prevention of a number of diseases or conditions, for example, neuropathic pain.

13 Claims, 14 Drawing Sheets

Related U.S. Application Data

(60) Provisional application No. 62/033,723, filed on Aug. 6, 2014, provisional application No. 61/909,742, filed on Nov. 27, 2013.

(56) References Cited

U.S. PATENT DOCUMENTS

| 8,916,570 | B2 | 12/2014 | Jacobson et al. |
| 2012/0184569 | A1* | 7/2012 | Jacobson ............. C07D 473/34 514/263.22 |
| 2012/0264769 | A1 | 10/2012 | Jacobson et al. |
| 2017/0002007 | A1 | 1/2017 | Jacobson et al. |

OTHER PUBLICATIONS

Choi et al., "Preparative and stereoselective synthesis of the versatile intermediate for carbocyclic nucleosides: effects of the bulky protecting groups to enforce facial selectivity," *J. Org. Chem.*, 69 (7), 2634-2636 (2004).
International Preliminary Report on Patentability, Application No. PCT/US2014/066609, dated May 31, 2016.
International Search Report, Application No. PCT/US2014/066609, dated May 12, 2015.
Kuo et al., "Metallocene Antitumor Agents. Solution and Solid-State Molybdenocene Coordination Chemistry of DNA Constituents," *J. Am. Chem. Soc.*, 113, 9027-9045 (1991).
Paoletta et al., "Rational design of sulfonated A3 adenosine receptor-selective nucleosides as pharmacological tools to study chronic neuropathic pain," *J. Med. Chem.*, 56 (14), 5949-5963 (2013).
Tosh et al., "Extended N(6) substitution of rigid C2-arylethynyl nucleosides for exploring the role of extracellular loops in ligand recognition at the A3 adenosine receptor," *Bioorg. Med. Chem. Lett.*, 24 (15), 3302-3306 (2014).
Tosh et al., "Structure-guided design of A(3) adenosine receptor-selective nucleosides: combination of 2-arylethynyl and bicyclo[3.1.0]hexane substitutions," *J. Med. Chem.*, 55 (10), 4847-4860 (2012).
Tosh et al., "Truncated Nucleosides as A(3) Adenosine Receptor Ligands: Combined 2-Arylethynyl and Bicyclohexane Substitutions," *ACS Med. Chem. Lett.*, 3 (7), 596-601 (2012).
Written Opinion of the International Searching Authority, Application No. PCT/US2014/066609, dated May 12, 2015.
State Intellectual Property Office of China, Office Action in Application No. 201480073564.6 (dated Mar. 3, 2017) 16 pages.

* cited by examiner

MRS5698

MRS5676

A3 ADENOSINE RECEPTOR AGONISTS

CROSS-REFERENCE TO RELATED APPLICATIONS

This patent application is a divisional of U.S. patent application Ser. No. 15/039,778, filed May 26, 2016, which is a 371 of International Patent Application No. PCT/US2014/066609, filed Nov. 20, 2014, which claims the benefit of U.S. Provisional Patent Applications Nos. 61/909,742, filed Nov. 27, 2013, and 62/033,723, filed Aug. 6, 2014, the disclosures of the '778, '609, '742, and '723 applications are incorporated by reference for all purposes.

FEDERALLY SPONSORED RESEARCH OR DEVELOPMENT

This invention was made with Government support under Project Number DK031117-24 awarded by the National Institute of Diabetes and Digestive and Kidney Diseases. The Government has certain rights in this invention.

BACKGROUND OF THE INVENTION

Chronic neuropathic pain (NP) is a widespread condition that is often associated with diabetes, cancer, injury, exposure to toxic substances and a variety of other diseases such as AIDS and Parkinson's disease (Renfrey, S. et al., *Nat. Rev. Drug Discov.* 2003, 2: 175-6; Farquhar-Smith, P., *Curr. Opin. Support Palliat. Care* 2011, 5: 1-7). When it occurs subsequent to cancer chemotherapy or radiation therapy, it often necessitates the discontinuation of a life-saving treatment. Currently-used therapies for NP are poorly efficacious and suffer from serious side effects, ranging from liver toxicity to addiction and personality changes. In many cases, the therapy involves drugs developed for a different condition that were incidentally found to reduce NP, e.g. biogenic amine reuptake inhibitors such as the antidepressant amitriptyline, or anticonvulsant drugs such as gabapentin. Opioids, which are effective against acute pain, are not the first line of treatment for chronic NP, both because of addiction liability, low efficacy, development of antinociceptive tolerance and hypersensitivities to thermal, cold and mechanical insults (Ossipov, M. H. et al., *J. Neubiol.* 2004, 61: 126-48). Thus, there is an unmet need for chronic neuropathic pain treatment that operates on a different mechanism that can be given as stand alone or as adjuncts to opioids to allow effective pain relief over chronic use without engaging dependence.

BRIEF SUMMARY OF THE INVENTION

The invention provides a compound of the formula (I):

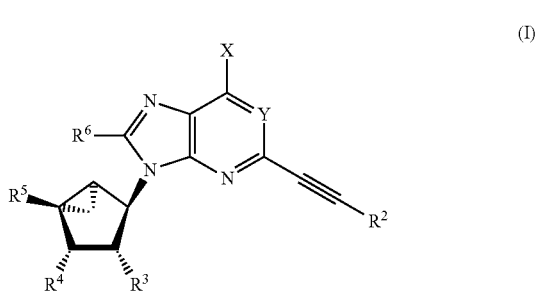

wherein X is selected from $NHR^1$, $CH_3$, and $CH=C(R^a)(R^b)$ wherein $R^a$ and $R^b$ are independently selected from hydrogen, hydroxyl, $C_1$-$C_6$ alkyl, and $C_6$-$C_{14}$ aryl, $R^1$ is selected from $C_1$-$C_6$ alkyl, $C_1$-$C_6$ alkoxy, hydroxyl, $C_3$-$C_8$ cycloalkyl, $C_6$-$C_{14}$ aryl $C_3$-$C_8$ cycloalkyl, $C_3$-$C_8$ cycloalkyl $C_1$-$C_6$ alkyl, $C_3$-$C_8$ dicycloalkyl $C_1$-$C_6$ alkyl, $C_7$-$C_{12}$ bicycloalkyl, $C_7$-$C_{12}$ bicycloalkyl $C_1$-$C_6$ alkyl, $C_7$-$C_{14}$ tricycloalkyl $C_1$-$C_6$ alkyl, $C_6$-$C_{14}$ aryl, $C_6$-$C_{14}$ aryl $C_1$-$C_6$ alkyl, $C_6$-$C_{14}$ diaryl $C_1$-$C_6$ alkyl, $C_6$-$C_{14}$ aryl $C_1$-$C_6$ alkoxy, heterocyclyl $C_1$-$C_6$ alkyl, heterocyclyl, 4-[[[4-[[[(2-amino $C_1$-$C_6$ alkyl) amino]-carbonyl]-$C_1$-$C_6$ alkyl]anilino] carbonyl] $C_1$-$C_6$ alkyl] $C_6$-$C_{14}$ aryl, and $C_6$-$C_{14}$ aryl $C_3$-$C_8$ cycloalkyl, wherein the aryl or heterocyclyl portion of $R^1$ is optionally substituted with one or more substituents selected from halo, amino, hydroxyl, carboxy, alkoxycarbonyl, aminocarbonyl, alkylaminocarbonyl, dialkylaminocarbonyl, $C_1$-$C_6$ alkyl, $C_2$-$C_6$ alkenyl, $C_2$-$C_6$ alkynyl, $C_1$-$C_6$ alkoxy, $C_6$-$C_{14}$ aryloxy, hydroxy $C_1$-$C_6$ alkyl, hydroxy $C_2$-$C_6$ alkenyl, hydroxy $C_2$-$C_6$ alkynyl, carboxy $C_1$-$C_6$ alkyl, carboxy $C_2$-$C_6$ alkenyl, carboxy $C_2$-$C_6$ alkynyl, aminocarbonyl $C_1$-$C_6$ alkyl, aminocarbonyl $C_2$-$C_6$ alkenyl, aminocarbonyl $C_2$-$C_6$ alkynyl, and any combination thereof; and the alkyl or cycloalkyl portion of $R^1$ is optionally substituted with one or more substituents selected from halo, amino, alkyl, alkoxy, aryloxy, hydroxyalkyl, hydroxyalkenyl, hydroxyalkynyl, aminocarbonylalkoxy, and arylalkoxy, and any combination thereof $R^2$ is selected from $C_6$-$C_{12}$ aryl, $C_3$-$C_8$ cycloalkyl, heteroaryl, and metallocenyl, wherein the aryl group is optionally substituted with one or more substituents selected from halo, trifluoromethyl, hydroxyalkyl, alkoxy, sulfonyloxy, carboxyalkyl, sulfonyloxyalkyl, arylcarbonyl, and any combination thereof, wherein the heteroaryl group is optionally substituted with one or more substituents selected from halo, trifluoromethyl, amino, alkyl, hydroxyalkyl, aryl, alkoxy, hydroxyl, carboxyl, sulfonyloxy, carboxyalkyl, sulfonyloxyalkyl, alkylcarbonyl, arylcarbonyl, and any combination thereof, $R^3$ and $R^4$ are independently selected from hydroxyl, amino, mercapto, ureido, $C_1$-$C_6$ alkyl carbonylamino, hydroxy $C_1$-$C_6$ alkyl, and hydrazinyl;

$R^5$ is selected from hydrogen, $C_1$-$C_3$ alkyl aminocarbonyl, di($C_1$-$C_3$ alkyl) aminocarbonyl, $C_1$-$C_3$ alkylthio $C_1$-$C_3$ alkyl, halo $C_1$-$C_3$ alkyl, hydrazinyl, amino $C_1$-$C_3$ alkyl, hydroxy $C_1$-$C_3$ alkyl, $C_3$-$C_6$ cycloalkylamino, hydroxylamino, and $C_2$-$C_3$ alkenyl; and $R^6$ is selected from hydrogen, $C_1$-$C_6$ alkyl, $C_2$-$C_6$ alkenyl, $C_2$-$C_6$ alkynyl, heteroaryl, and $C_1$-$C_6$ aminoalkyl;

or a pharmaceutically acceptable salt thereof.

The invention also provides a compound of the formula (II):

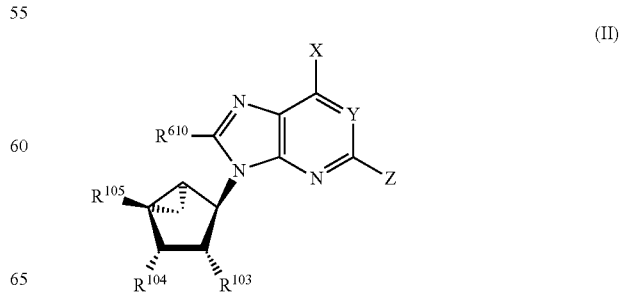

wherein X is selected from NHR$^{101}$, CH$_3$, and CH=C(R$^a$)(R$^b$) wherein R$^a$ and R$^b$ are independently selected from hydrogen, hydroxyl, C$_1$-C$_6$ alkyl, and C$_6$-C$_{14}$ aryl, Y is N or CH, R$^{101}$ is selected from C$_1$-C$_6$ alkyl, C$_1$-C$_6$ alkoxy, hydroxyl, C$_3$-C$_8$ cycloalkyl, C$_6$-C$_{14}$ aryl C$_3$-C$_8$ cycloalkyl, C$_3$-C$_8$ cycloalkyl C$_1$-C$_6$ alkyl, C$_3$-C$_8$ dicycloalkyl C$_1$-C$_6$ alkyl, C$_7$-C$_{12}$ bicycloalkyl, C$_7$-C$_{12}$ bicycloalkyl C$_1$-C$_6$ alkyl, C$_7$-C$_{14}$ tricycloalkyl C$_1$-C$_6$ alkyl, C$_6$-C$_{14}$ aryl, C$_6$-C$_{14}$ aryl C$_1$-C$_6$ alkyl, C$_6$-C$_{14}$ diaryl C$_1$-C$_6$ alkyl, C$_6$-C$_{14}$ aryl C$_1$-C$_6$ alkoxy, heterocyclyl C$_1$-C$_6$ alkyl, heterocyclyl, 4-[[[4-[[[(2-amino C$_1$-C$_6$ alkyl) amino]-carbonyl]-C$_1$-C$_6$ alkyl]anilino] carbonyl] C$_1$-C$_6$ alkyl] C$_6$-C$_{14}$ aryl, and C$_6$-C$_{14}$ aryl C$_3$-C$_8$ cycloalkyl, wherein the aryl or heterocyclyl portion of R$^1$ is optionally substituted with one or more substituents selected from halo, amino, hydroxyl, carboxy, alkoxycarbonyl, aminocarbonyl, alkylaminocarbonyl, dialkylaminocarbonyl, C$_1$-C$_6$ alkyl, C$_2$-C$_6$ alkenyl, C$_2$-C$_6$ alkynyl, C$_1$-C$_6$ alkoxy, C$_6$-C$_{14}$ aryloxy, hydroxy C$_1$-C$_6$ alkyl, hydroxy C$_2$-C$_6$ alkenyl, hydroxy C$_2$-C$_6$ alkynyl, carboxy C$_1$-C$_6$ alkyl, carboxy C$_2$-C$_6$ alkenyl, carboxy C$_2$-C$_6$ alkynyl, aminocarbonyl C$_1$-C$_6$ alkyl, aminocarbonyl C$_2$-C$_6$ alkenyl, aminocarbonyl C$_2$-C$_6$ alkynyl, and any combination thereof; and the alkyl or cycloalkyl portion of R$^{101}$ is optionally substituted with one or more substituents selected from halo, amino, alkyl, alkoxy, aryloxy, hydroxyalkyl, hydroxyalkenyl, hydroxyalkynyl, aminocarbonylalkoxy, and arylalkoxy, and any combination thereof, Z is halo, azido, or a group of the formula:

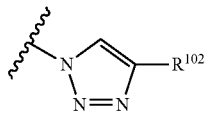

wherein R$^{102}$ is selected from C$_6$-C$_{12}$ aryl, C$_6$-C$_{12}$ aryl-C$_1$-C$_6$ alkyl, C$_3$-C$_8$ cycloalkyl, heteroaryl, and metallocenyl, wherein the aryl group is optionally substituted with one or more substituents selected from trifluoromethyl, hydroxyalkyl, alkoxy, sulfonyloxy, carboxyalkyl, sulfonyloxyalkyl, arylcarbonyl, and any combination thereof, wherein the heteroaryl group is optionally substituted with one or more substituents selected from halo, trifluoromethyl, amino, alkyl, hydroxyalkyl, aryl, alkoxy, hydroxyl, carboxyl, sulfonyloxy, carboxyalkyl, sulfonyloxyalkyl, alkylcarbonyl, arylcarbonyl, and any combination thereof, R$^{103}$ and R$^{104}$ are independently selected from hydrogen, hydroxyl, amino, mercapto, ureido, C$_1$-C$_6$ alkyl carbonylamino, hydroxy C$_1$-C$_6$ alkyl, and hydrazinyl;

R$^{105}$ is selected from hydrogen, C$_1$-C$_3$ alkyl aminocarbonyl, di(C$_1$-C$_3$ alkyl) aminocarbonyl, C$_1$-C$_3$ alkylthio C$_1$-C$_3$ alkyl, halo C$_1$-C$_3$ alkyl, hydrazinyl, amino C$_1$-C$_3$ alkyl, hydroxy C$_1$-C$_3$ alkyl, C$_3$-C$_6$ cycloalkylamino, hydroxylamino, and C$_2$-C$_3$ alkenyl; and R$^{106}$ is selected from hydrogen, C$_1$-C$_6$ alkyl, C$_2$-C$_6$ alkenyl, C$_2$-C$_6$ alkynyl, heteroaryl, and C$_1$-C$_6$ aminoalkyl;

or a pharmaceutically acceptable salt thereof.

The invention further provides a pharmaceutical composition comprising a compound or salt of the invention and a pharmaceutically acceptable carrier.

The invention additionally provides a method for activating an A$_3$ adenosine receptor in a mammal comprising to the mammal an effective amount of a compound or salt of the invention.

The invention also provides a method for treating or preventing neuropathic pain in a mammal in need thereof, comprising administering to the mammal an effective amount of a compound or salt of the invention.

Advantageously, the inventive compounds exhibit desirable drug-like physicochemical properties that include a molecular weight of less than about 500 Daltons, which is expected to confer oral bioavailability. In addition, there are both peripheral and central mechanistic components to protection against neuropathic pain exhibited by A$_3$AR agonists. The inventive compounds possess physicochemical properties that are favorable for crossing the blood-brain barrier and thus may act within the brain.

BRIEF DESCRIPTION OF THE SEVERAL VIEWS OF THE DRAWING(S)

Figure 8A:
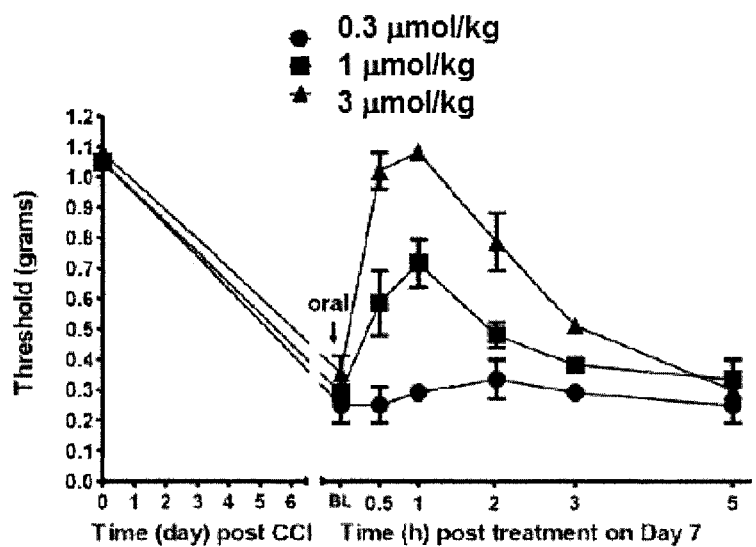
Figure 8B:
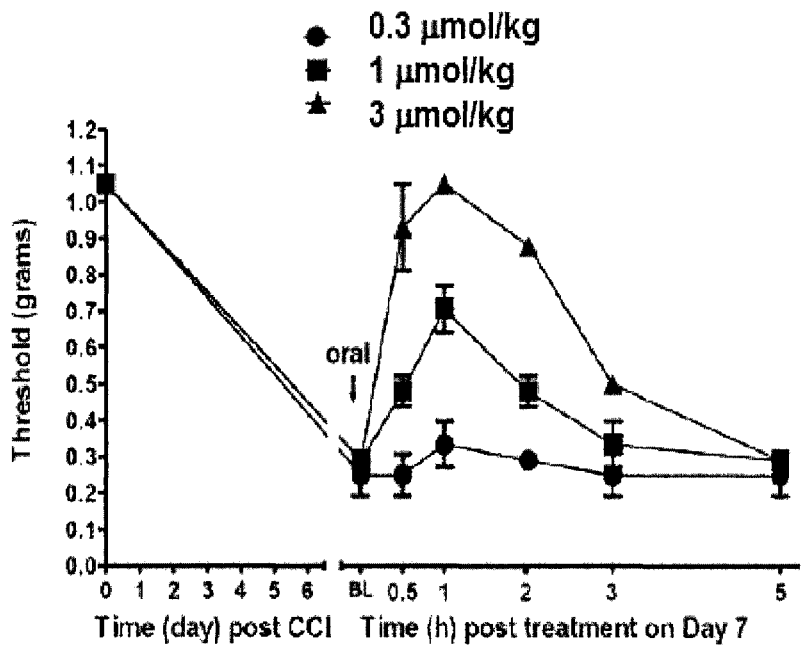
Figure 8C:
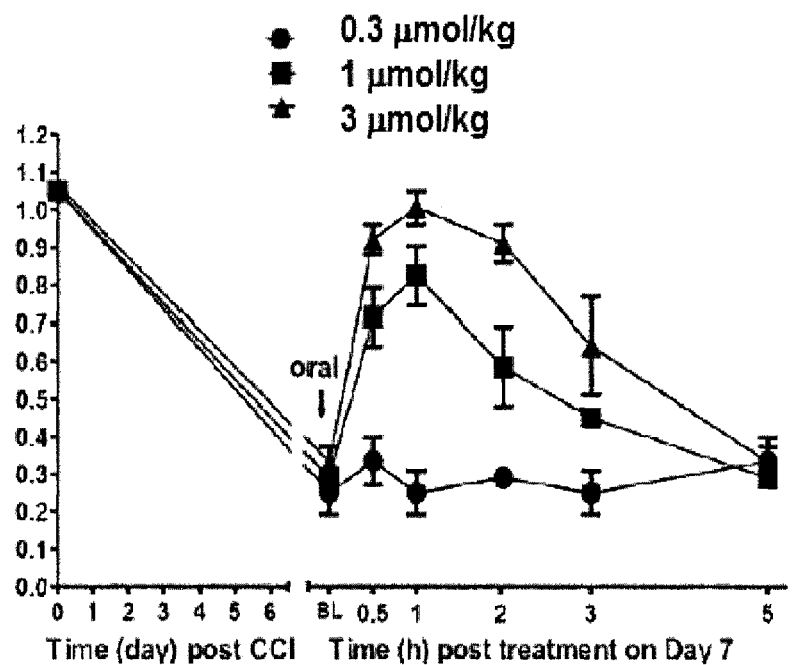

FIGS. 8A-8C illustrate reversal of mechano-allodynia over time exhibited by compounds 7 (FIG. 8A), 17 (FIG. 8B), and 32 (FIG. 8C) at doses of 0.3 mmol/kg, 1 mmol/kg, and 3 mmol/kg in a chronic constriction injury model of neuropathic pain.

Figure 9A:
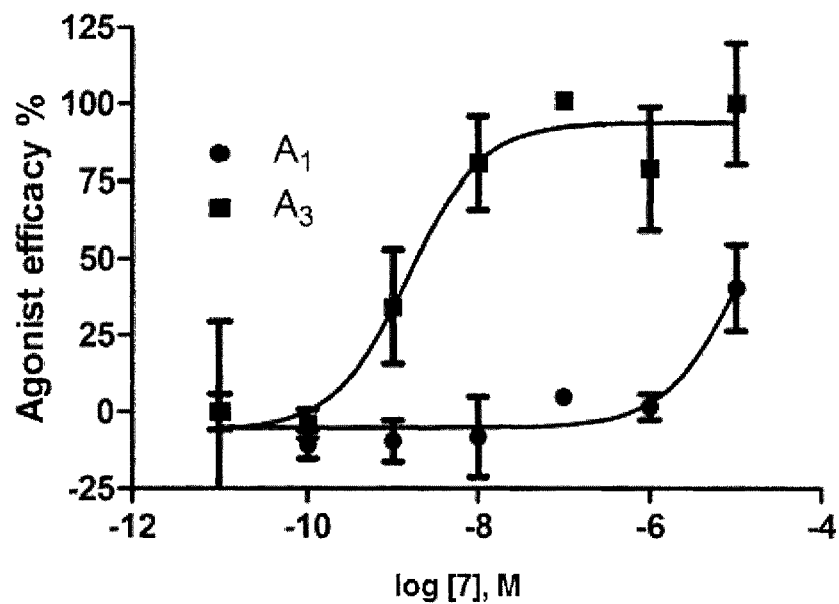
Figure 9B:
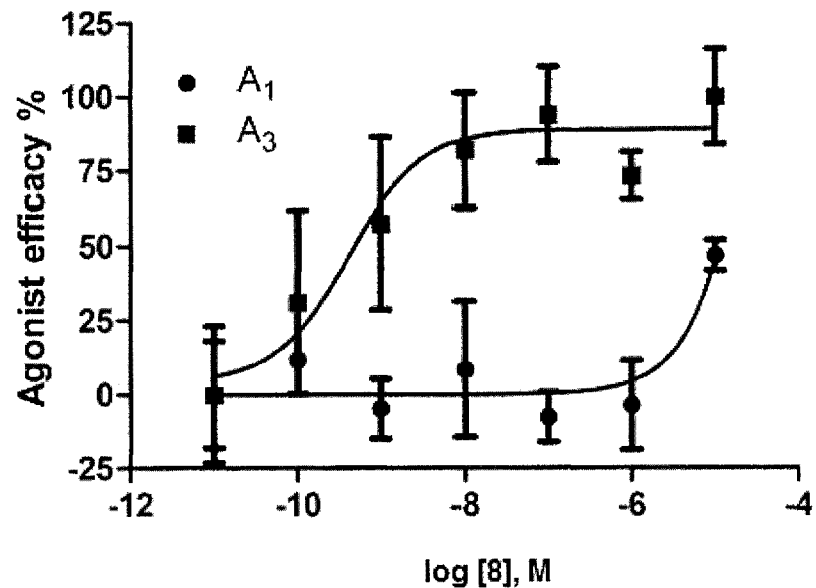

FIGS. 9A and 9B illustrate the activity in the inhibition of cyclic AMP formation at the human A$_1$AR and A$_3$AR of compounds 7 (FIG. 9A) and 8 (FIG. 9B).

Figure 10:
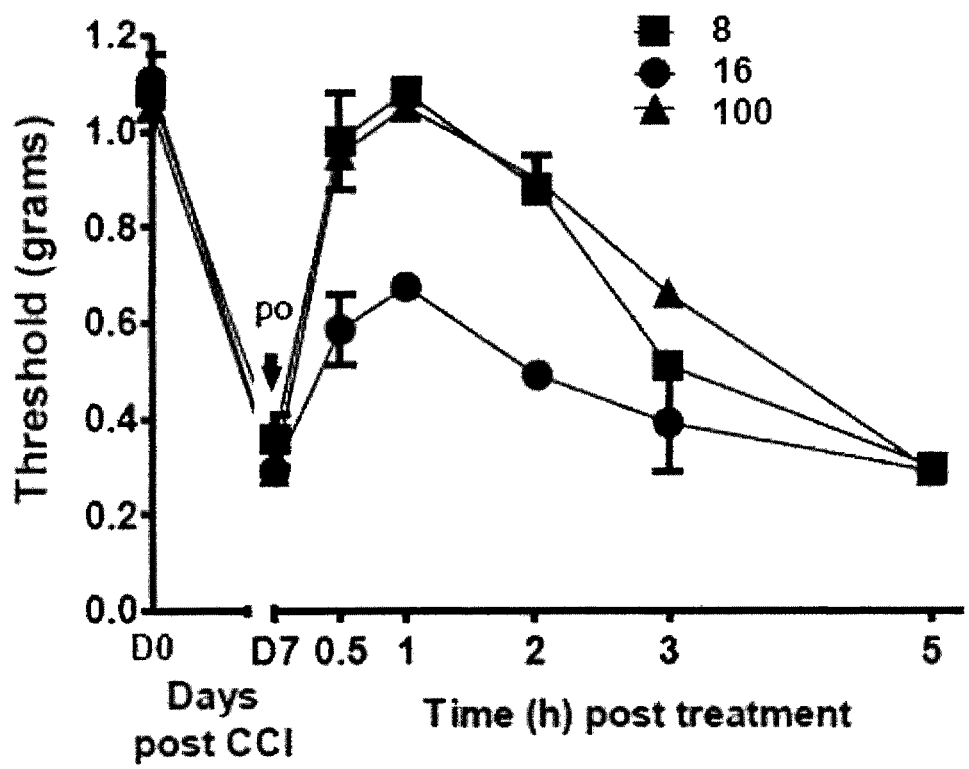

FIG. 10 illustrates the reversal of mechano-allodynia over time exhibited by compounds 8, 16, and 100 in a chronic constriction injury model of neuropathic pain.

Figure 11:
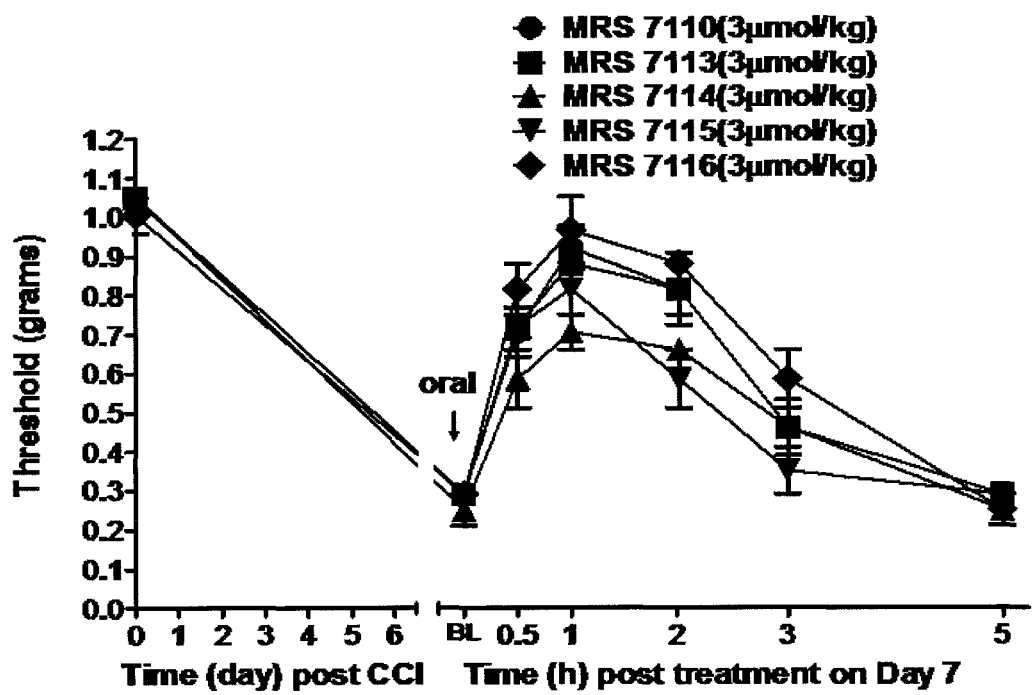

FIG. 11 illustrates the reversal of mechano-allodynia over time exhibited by compounds 100 (MRS7110), 105 (MRS7113), 103 (MRS7114), 101 (MRS7115), and 104 (MRS7116,) respectively, in a chronic constriction injury model of neuropathic pain.

Figure 12:
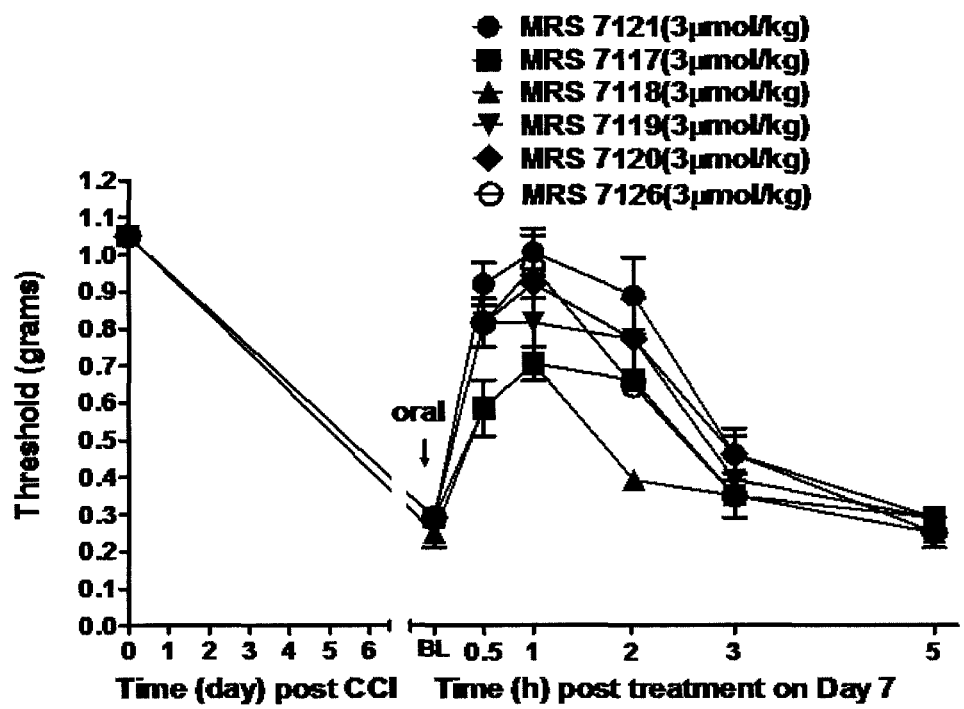

FIG. 12 illustrates the reversal of mechano-allodynia over time exhibited by compounds 112 (MRS7121), 102 (MRS7117), 108 (MRS7118), 111 (MRS7119), 106 (MRS7120), and 110 (MRS7126), respectively, in a chronic constriction injury model of neuropathic pain.

Figure 13A:
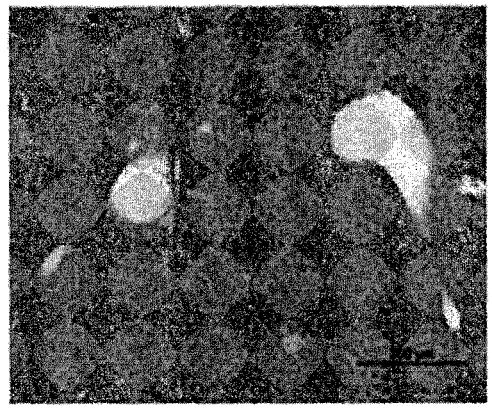
Figure 13B:
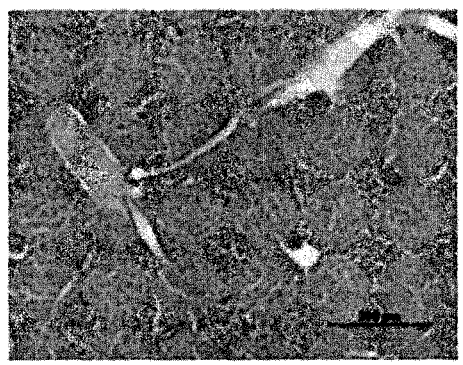

FIGS. 13A and 13B depict the histological analysis of liver samples from control (FIG. 13A) and compound 32-treated (FIG. 13B) groups.

Figure 14:
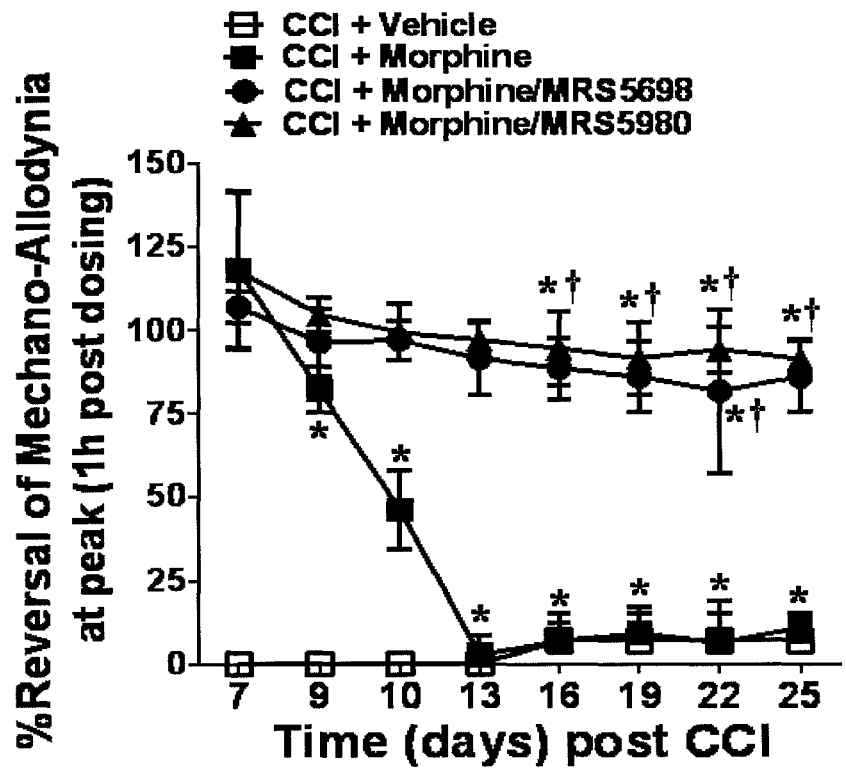

FIG. 14 illustrates the maintenance of the reversal of mechano-allodynia over time exhibited by morphine when dosed in combination with MRS5698 or compound 32.

Figure 15:
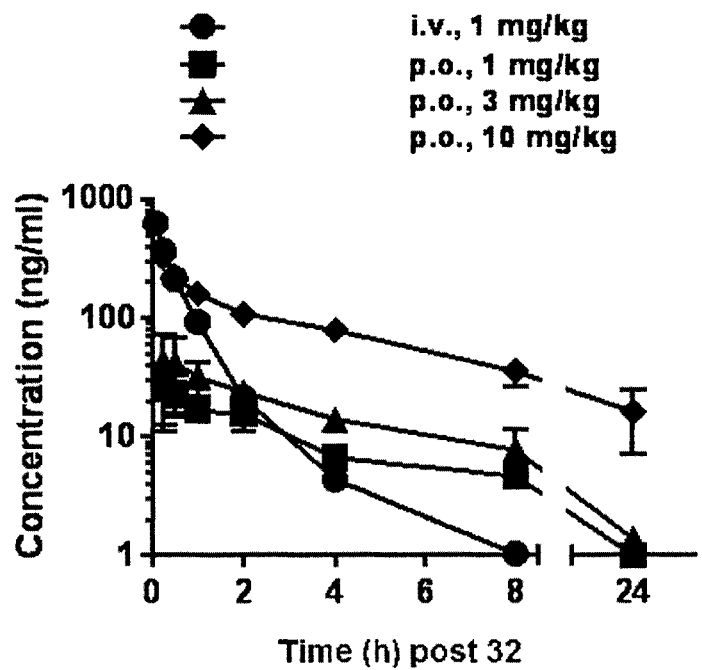

FIG. 15 depicts plasma concentration as a function of time in male SD rats upon intravenous dosing of compound 32 at 1 mg/kg and upon oral dosing at 1, 3, and 10 mg/kg.

Figure 16:
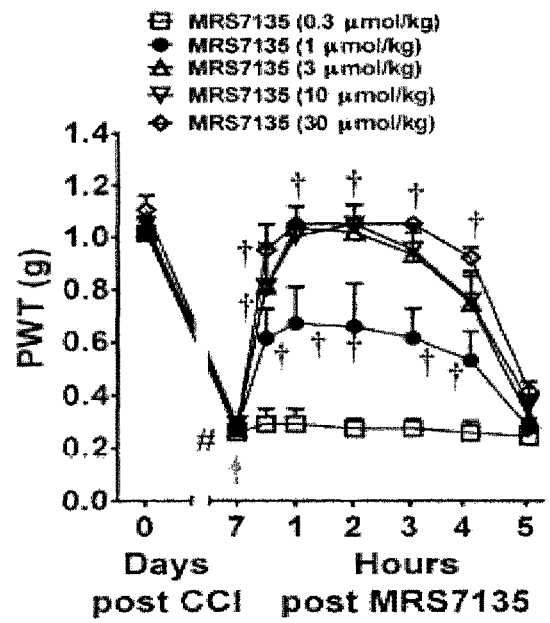

FIG. 16 illustrates the reversal of mechano-allodynia over time exhibited by compound 126 (MRS7135) on oral dosing at 0.3, 1, 2, 10, and 30 μmol/kg dosing.

Figure 17:
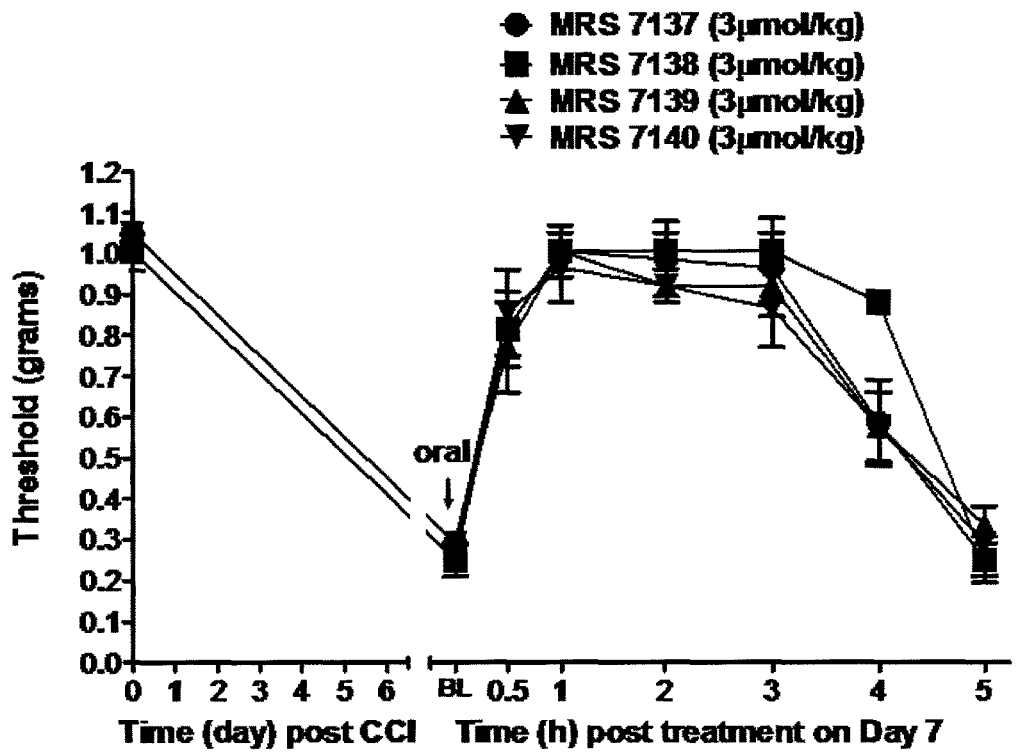

FIG. 17 illustrates the reversal of mechano-allodynia over time exhibited by compounds 125 (MRS7137), 120 (MRS7138), 121 (MRS7139), and 127 (MRS7140,) respectively, in a chronic constriction injury model of neuropathic pain.

DETAILED DESCRIPTION OF THE INVENTION

In an embodiment, the invention provides a compound of the formula (I):

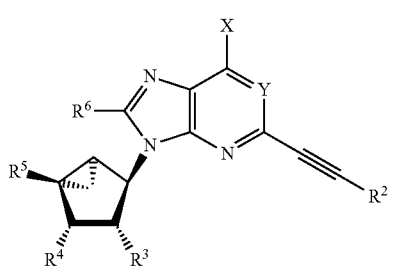

(I)

wherein X is selected from $NHR^1$, $CH_3$, and $CH=C(R^a)(R^b)$ wherein $R^a$ and $R^b$ are independently selected from hydrogen, hydroxyl, $C_1$-$C_6$ alkyl, and $C_6$-$C_{14}$ aryl, $R^1$ is selected from $C_1$-$C_6$ alkyl, $C_1$-$C_6$ alkoxy, hydroxyl, $C_3$-$C_8$ cycloalkyl, $C_6$-$C_{14}$ aryl $C_3$-$C_8$ cycloalkyl, $C_3$-$C_8$ cycloalkyl $C_1$-$C_6$ alkyl, $C_3$-$C_8$ dicycloalkyl $C_1$-$C_6$ alkyl, $C_7$-$C_{12}$ bicycloalkyl, $C_7$-$C_{12}$ bicycloalkyl $C_1$-$C_6$ alkyl, $C_7$-$C_{14}$ tricycloalkyl $C_1$-$C_6$ alkyl, $C_6$-$C_{14}$ aryl, $C_6$-$C_{14}$ aryl $C_1$-$C_6$ alkyl, $C_6$-$C_{14}$ diaryl $C_1$-$C_6$ alkyl, $C_6$-$C_{14}$ aryl $C_1$-$C_6$ alkoxy, heterocyclyl $C_1$-$C_6$ alkyl, heterocyclyl, 4-[[[4-[[[(2-amino $C_1$-$C_6$ alkyl) amino]-carbonyl]-$C_1$-$C_6$ alkyl]anilino]carbonyl] $C_1$-$C_6$ alkyl] $C_6$-$C_{14}$ aryl, and $C_6$-$C_{14}$ aryl $C_3$-$C_8$ cycloalkyl, wherein the aryl or heterocyclyl portion of $R^1$ is optionally substituted with one or more substituents selected from halo, amino, hydroxyl, carboxy, alkoxycarbonyl, aminocarbonyl, alkylaminocarbonyl, dialkylaminocarbonyl, $C_1$-$C_6$ alkyl, $C_2$-$C_6$ alkenyl, $C_2$-$C_6$ alkynyl, $C_1$-$C_6$ alkoxy, $C_6$-$C_{14}$ aryloxy, hydroxy $C_1$-$C_6$ alkyl, hydroxy $C_2$-$C_6$ alkenyl, hydroxy $C_2$-$C_6$ alkynyl, carboxy $C_1$-$C_6$ alkyl, carboxy $C_2$-$C_6$ alkenyl, carboxy $C_2$-$C_6$ alkynyl, aminocarbonyl $C_1$-$C_6$ alkyl, aminocarbonyl $C_2$-$C_6$ alkenyl, aminocarbonyl $C_2$-$C_6$ alkynyl, and any combination thereof; and the alkyl or cycloalkyl portion of $R^1$ is optionally substituted with one or more selected from halo, amino, alkyl, alkoxy, aryloxy, hydroxyalkyl, hydroxyalkenyl, hydroxyalkynyl, aminocarbonylalkoxy, and arylalkoxy, and any combination thereof $R^2$ is selected from $C_6$-$C_{12}$ aryl, $C_3$-$C_8$ cycloalkyl, heteroaryl, and metallocenyl, wherein the aryl group is optionally substituted from halo, trifluoromethyl, hydroxyalkyl, alkoxy, sulfonyloxy, carboxyalkyl, sulfonyloxyalkyl, arylcarbonyl, and any combination thereof, wherein the heteroaryl group is optionally substituted with one or more substituents selected from halo, trifluoromethyl, amino, alkyl, hydroxyalkyl, aryl, benzo, alkoxy, hydroxyl, carboxyl, sulfonyloxy, carboxyalkyl, sulfonyloxyalkyl, alkylcarbonyl, arylcarbonyl, and any combination thereof, $R^3$ and $R^4$ are independently selected from hydroxyl, amino, mercapto, ureido, $C_1$-$C_6$ alkyl carbonylamino, hydroxy $C_1$-$C_6$ alkyl, and hydrazinyl;

$R^5$ is selected from hydrogen, $C_1$-$C_3$ alkyl aminocarbonyl, di($C_1$-$C_3$ alkyl) aminocarbonyl, $C_1$-$C_3$ alkylthio $C_1$-$C_3$ alkyl, halo $C_1$-$C_3$ alkyl, hydrazinyl, amino $C_1$-$C_3$ alkyl, hydroxy $C_1$-$C_3$ alkyl, $C_3$-$C_6$ cycloalkylamino, hydroxylamino, and $C_2$-$C_3$ alkenyl; and $R^6$ is selected from hydrogen, $C_1$-$C_6$ alkyl, $C_2$-$C_6$ alkenyl, $C_2$-$C_6$ alkynyl, heteroaryl, and $C_1$-$C_6$ aminoalkyl;

or a pharmaceutically acceptable salt thereof.

In an embodiment, when $R^1$ is methyl, $R^3$ and $R^4$ are both hydroxyl, $R^6$ is hydrogen, and $R^5$ is methylaminocarbonyl, $R^2$ is not 2-pyridyl or phenyl.

In an embodiment, $R^6$ is hydrogen.

In certain embodiments, Y is N.

In certain embodiments, $R^5$ is selected from $C_1$-$C_3$ alkyl aminocarbonyl or di($C_1$-$C_3$ alkyl) aminocarbonyl.

In an embodiment, $R^3$ and $R^4$ are both hydroxyl.

In an embodiment, X is $NHR^1$. In a preferred embodiment, $R^1$ is $C_1$-$C_6$ alkyl.

In certain embodiments, $R^2$ is $C_6$-$C_{10}$ aryl, wherein the aryl group is substituted with one or more substituents selected from halo, trifluoromethyl, hydroxyalkyl, alkoxy, and any combination thereof.

In certain other embodiments, $R^2$ is heteroaryl, and the heteroaryl group is optionally substituted with one or more substituents selected from hydroxy, halo and alkyl.

In certain preferred embodiments, the compound is selected from:

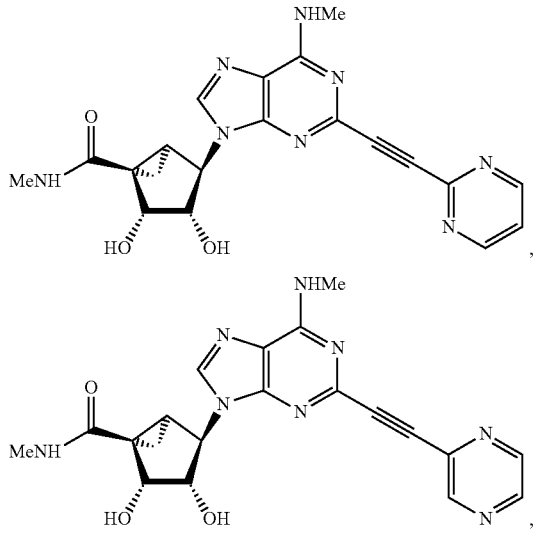

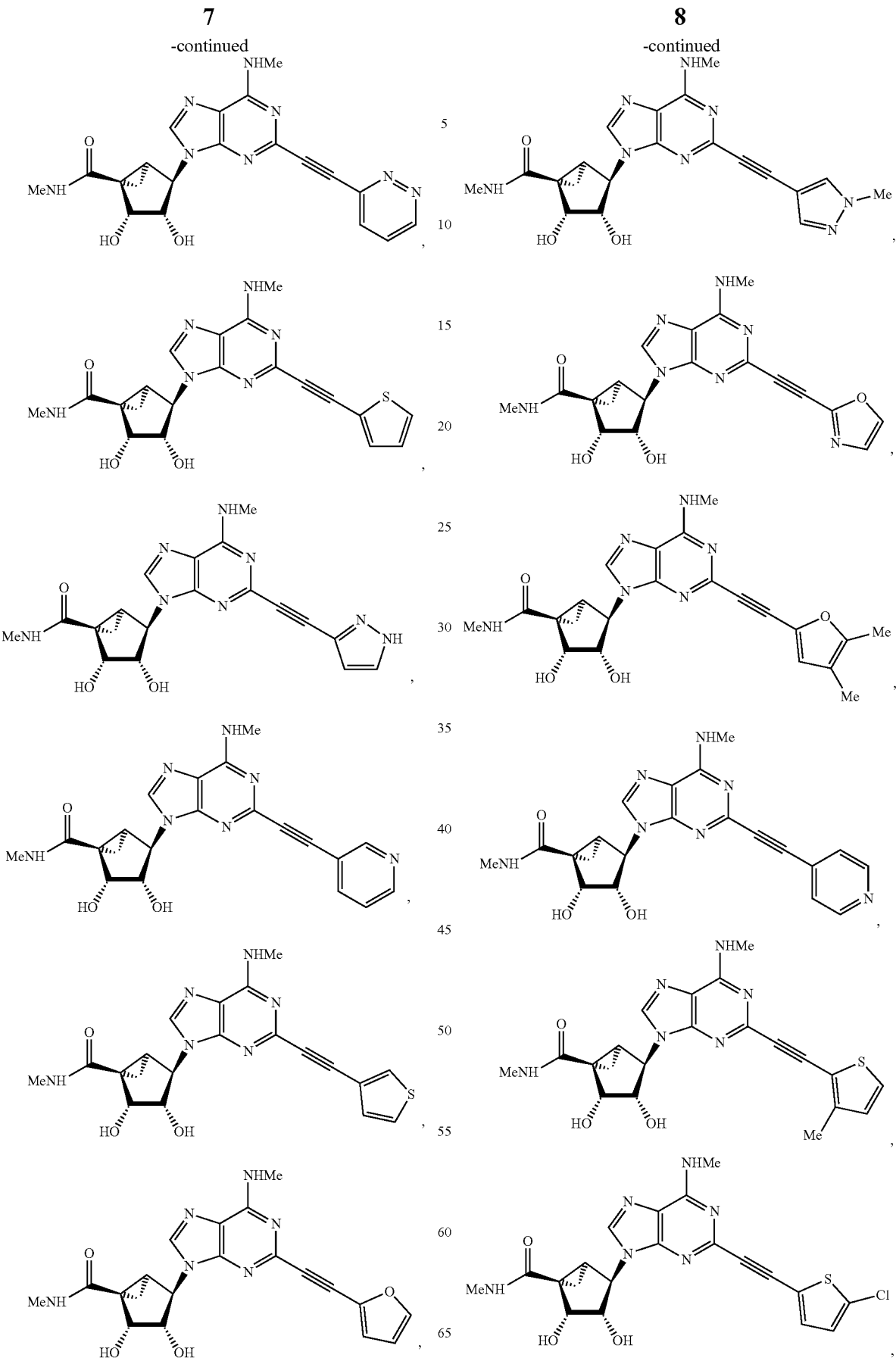

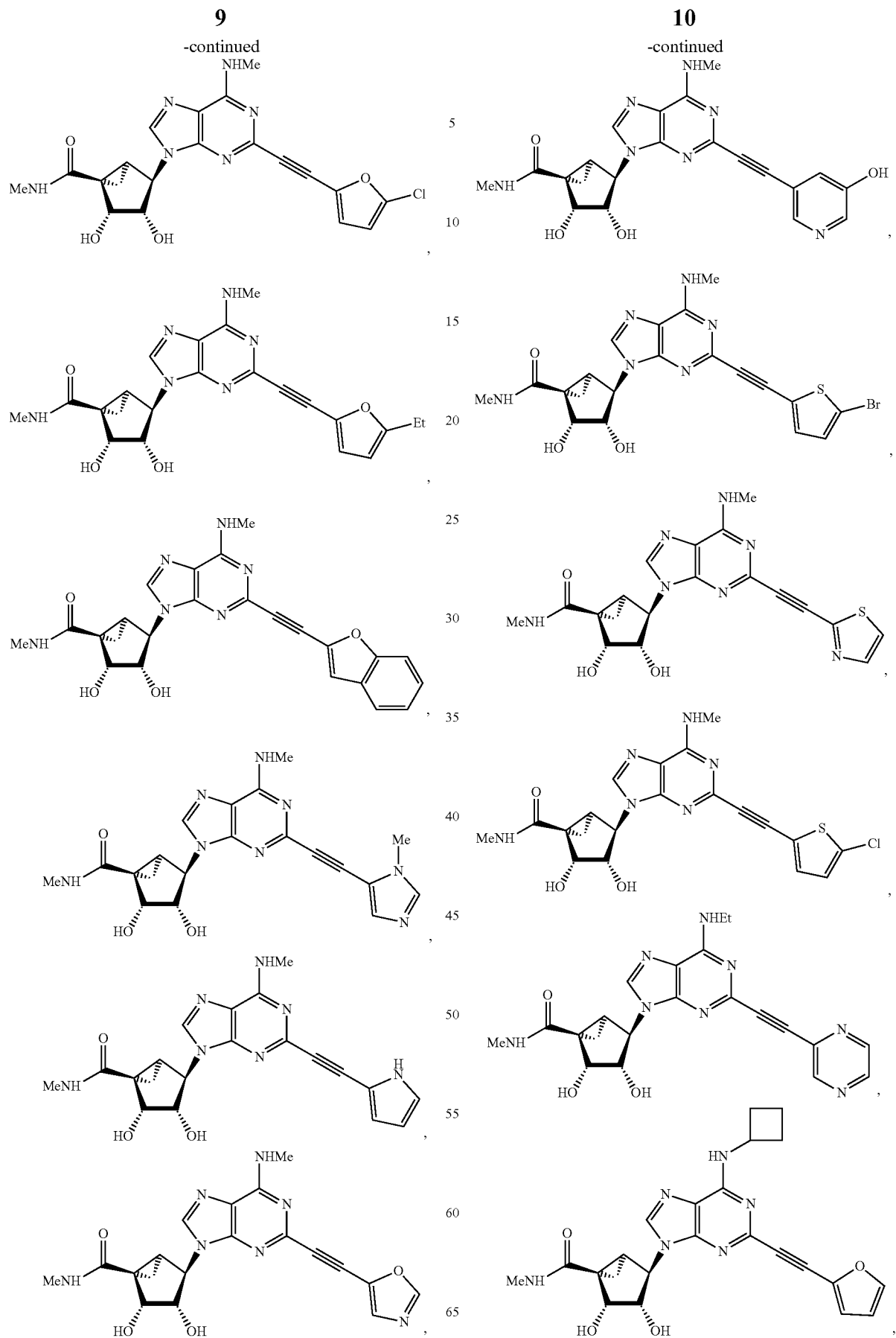

-continued
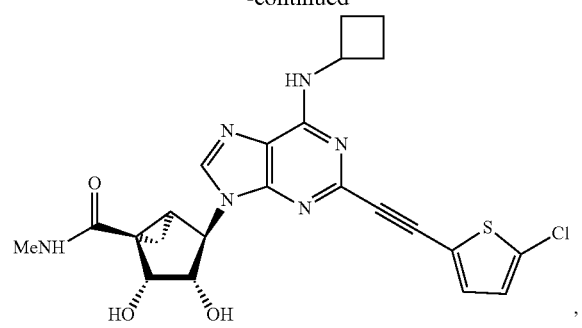
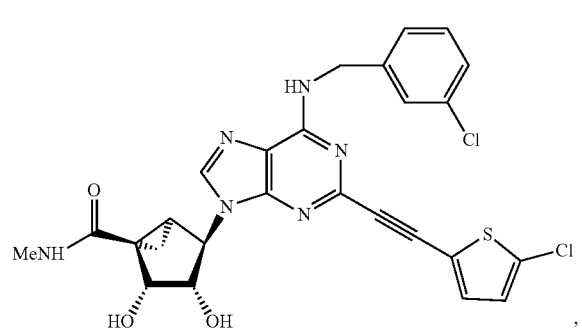
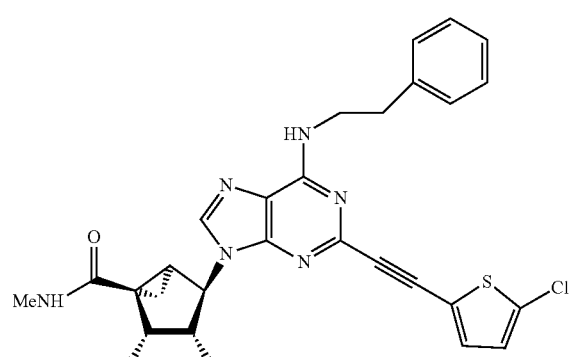
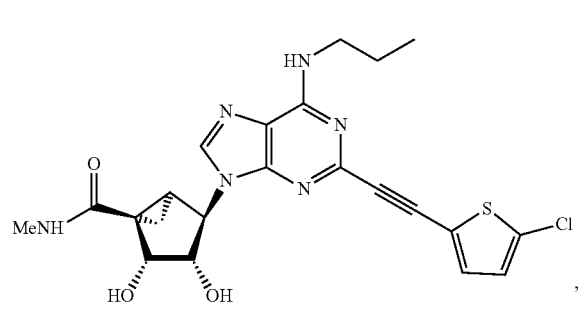
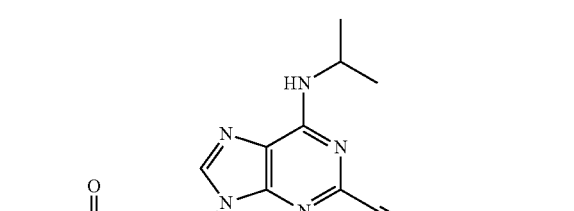
-continued
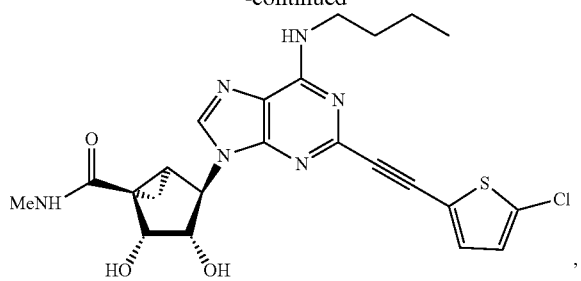
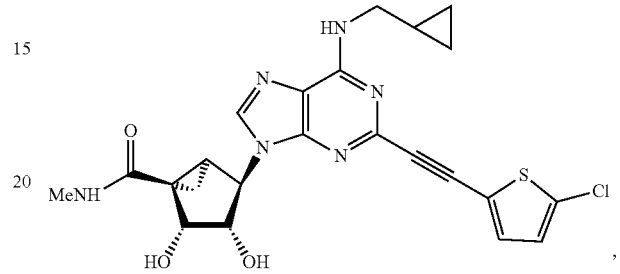
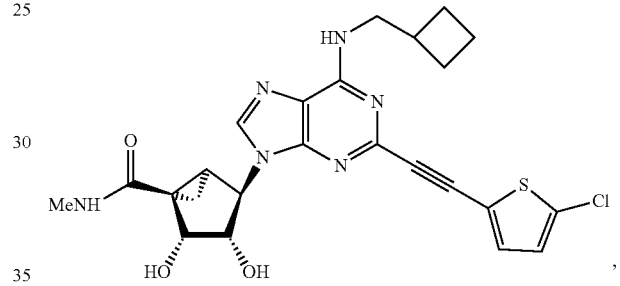
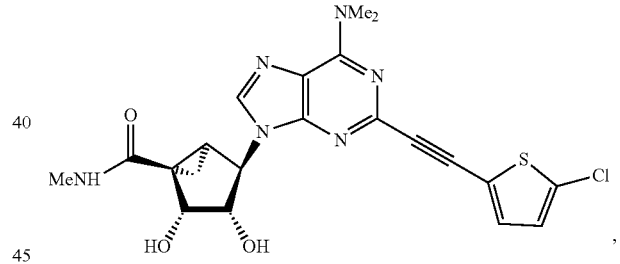
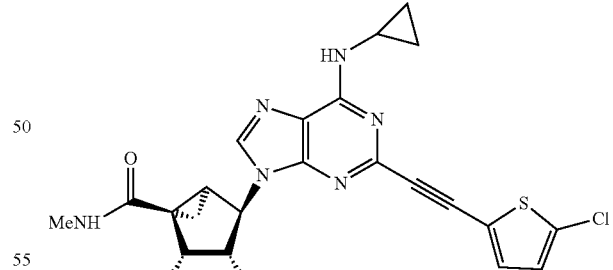
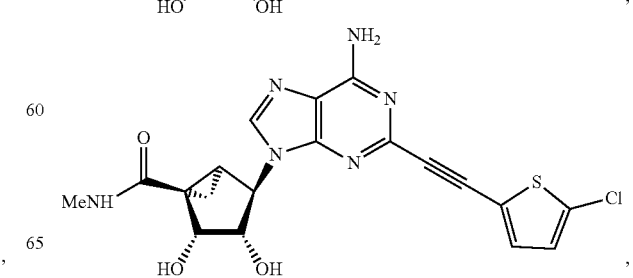

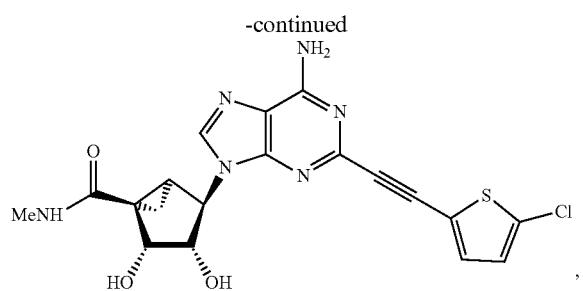
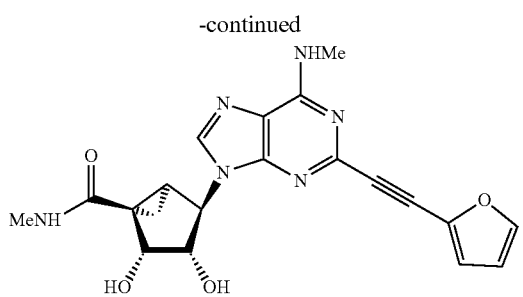
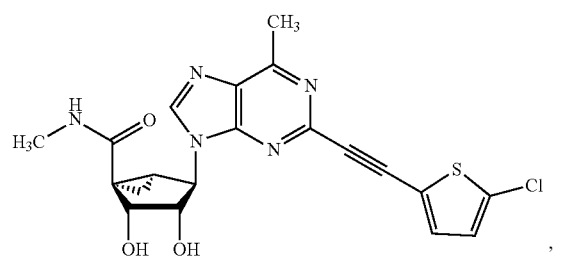
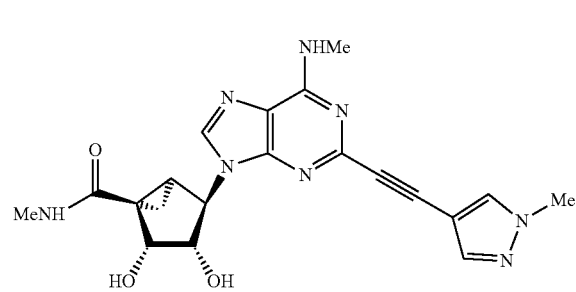
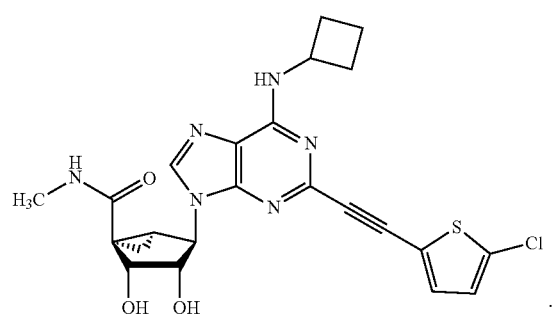
and
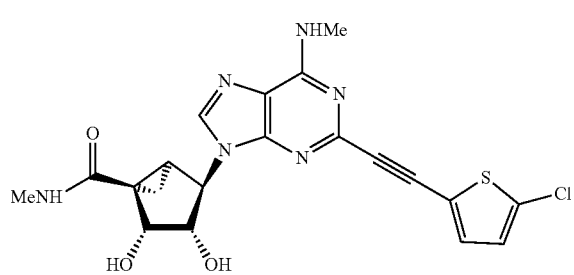
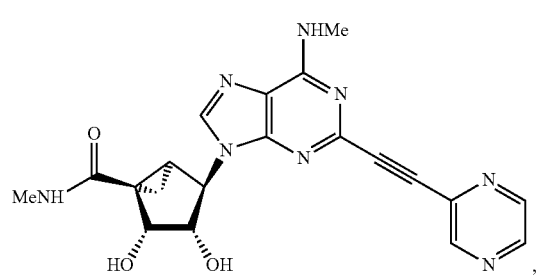
In certain more preferred embodiments, the compound is selected from:
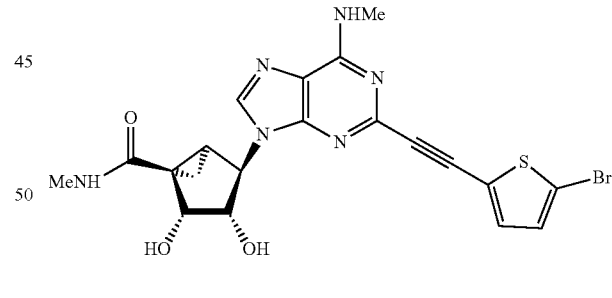
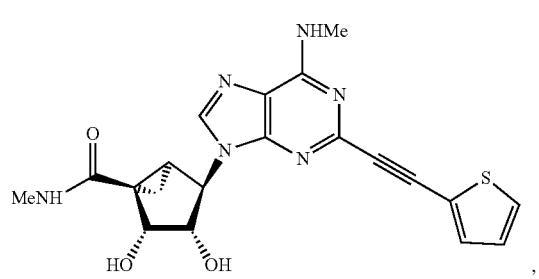
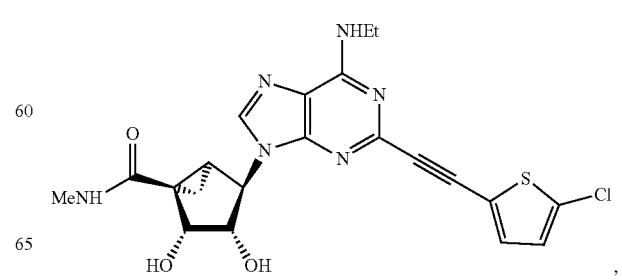

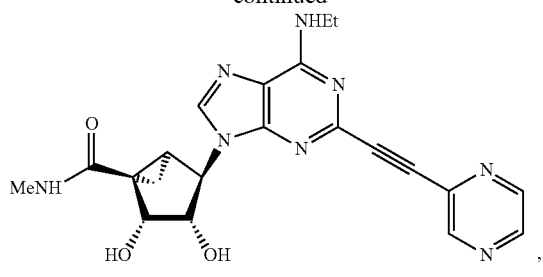

and

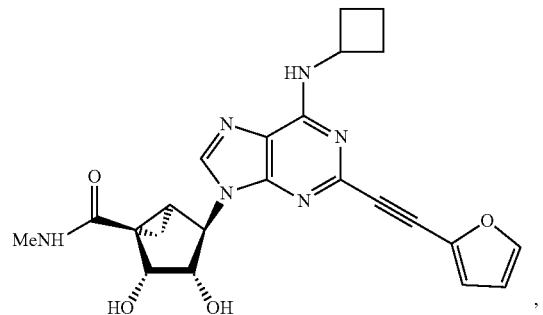

In a certain embodiment, the compound is:

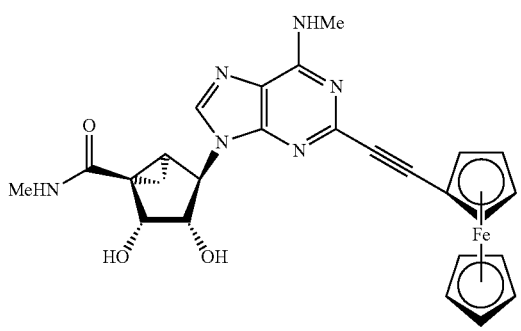

In certain preferred embodiments, the compound is selected from:

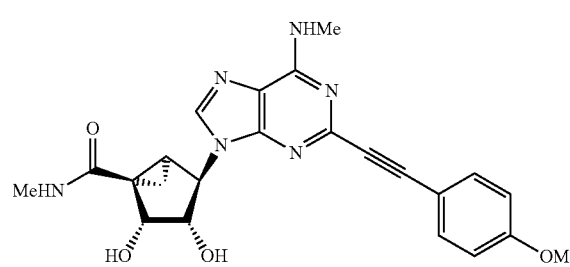

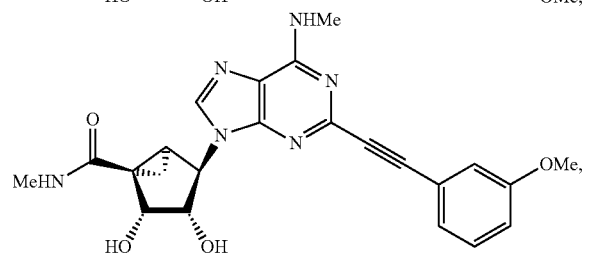

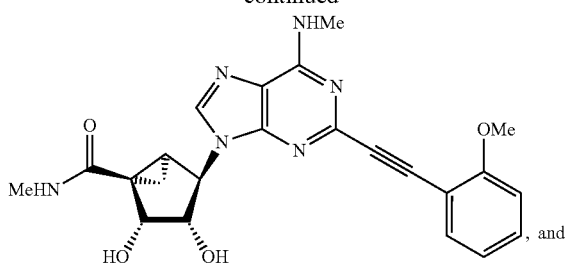, and

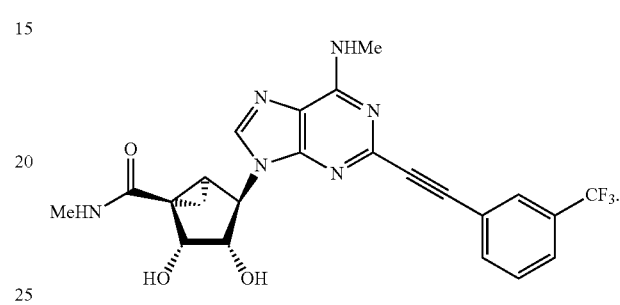

In certain embodiments, R¹ is $C_6$-$C_{14}$ aryl $C_3$-$C_8$ cycloalkyl, wherein the aryl group is optionally substituted with one or more substituents selected from $C_1$-$C_6$ alkyl, methyl, F, Cl, and Br.

In certain preferred embodiments, the compound is selected from:

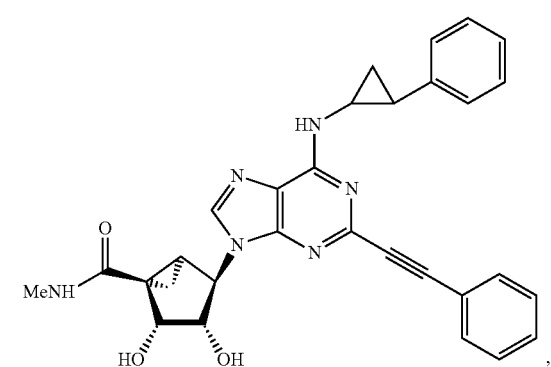

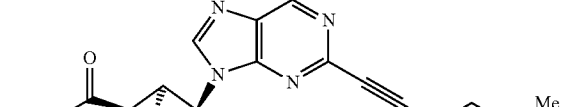

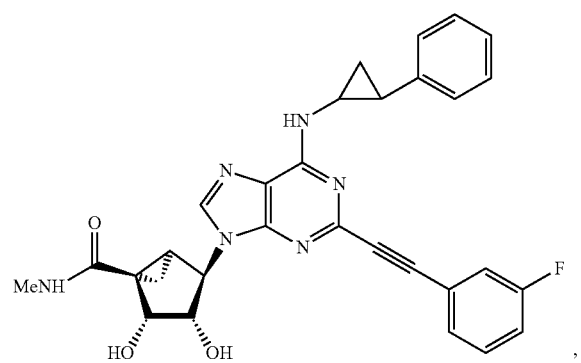
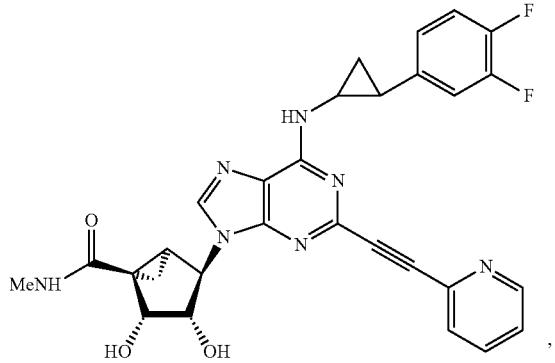
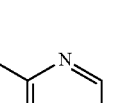
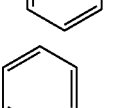
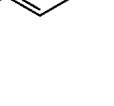
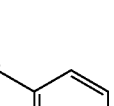
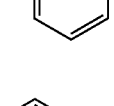
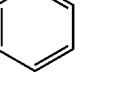
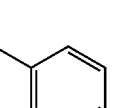
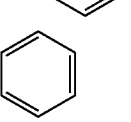
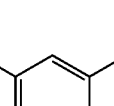
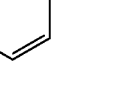
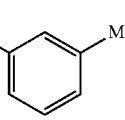

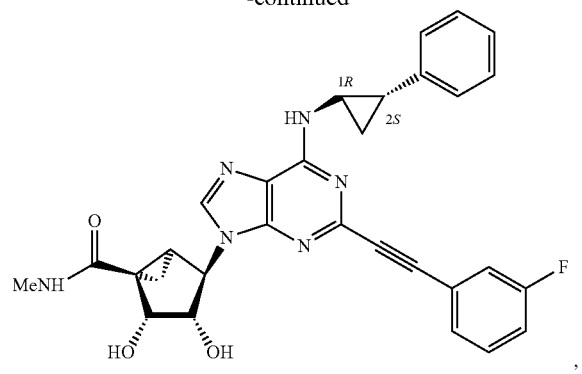
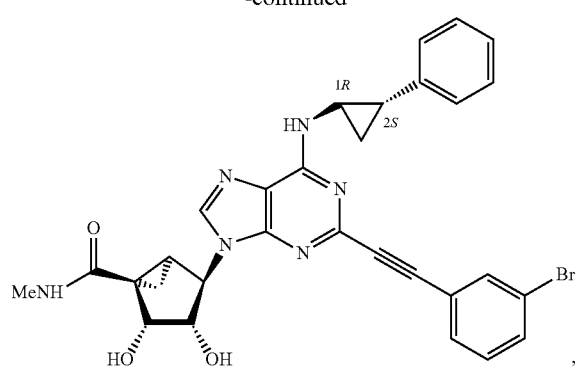
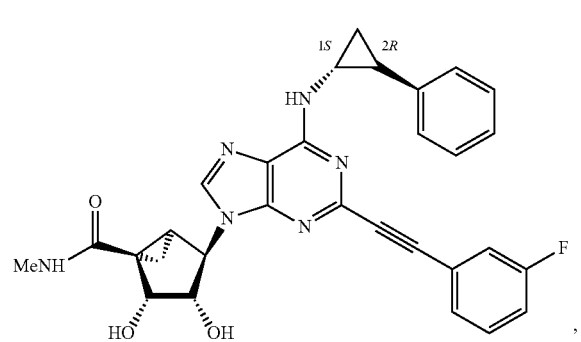
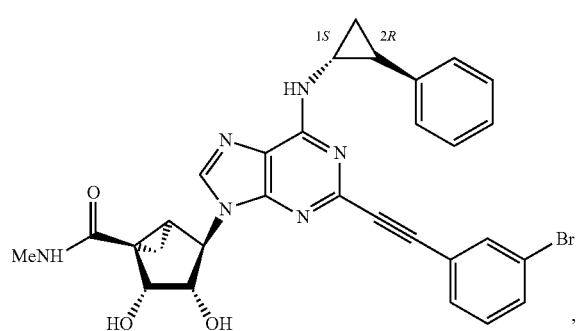
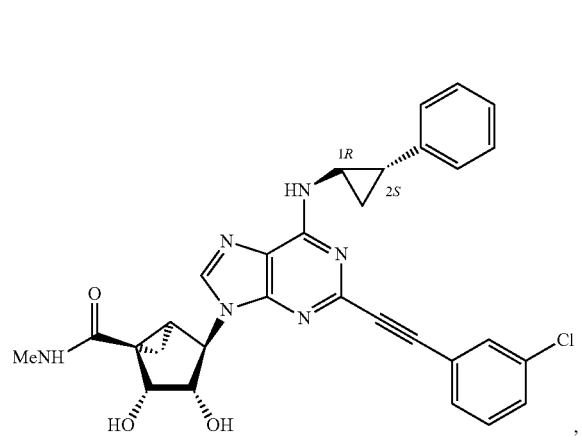
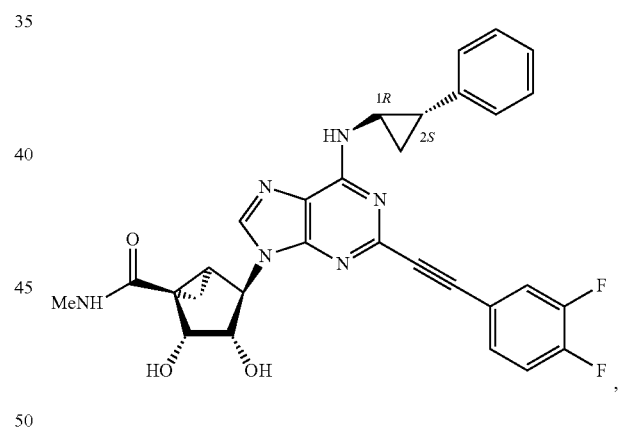
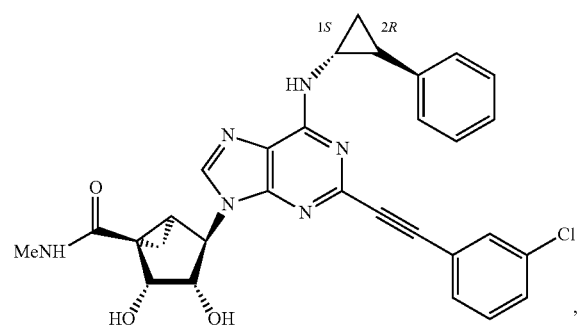
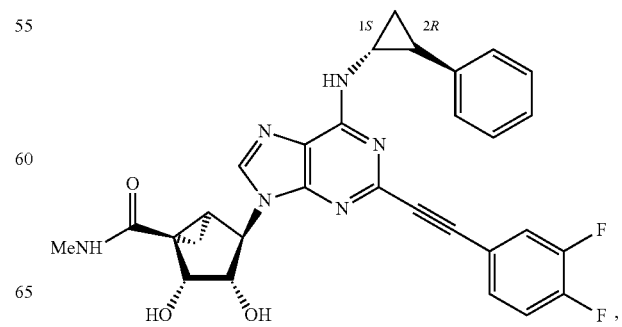

-continued

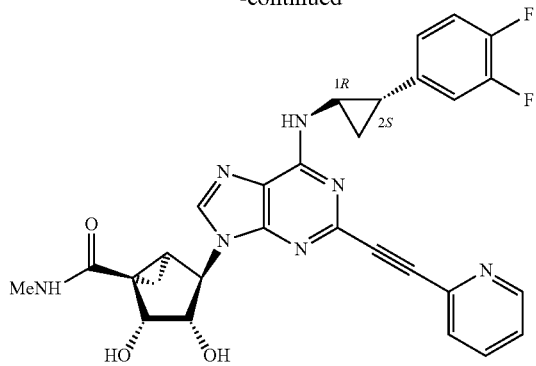

and

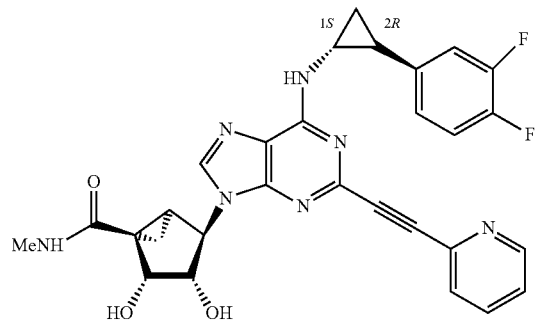

In certain embodiments, X is CH₃.
In a particular embodiment, the compound is:

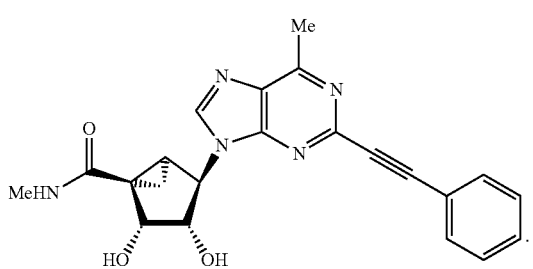

In certain embodiments, X is CH=C(Rᵃ)(Rᵇ).
In a particular embodiment, the compound is selected from:

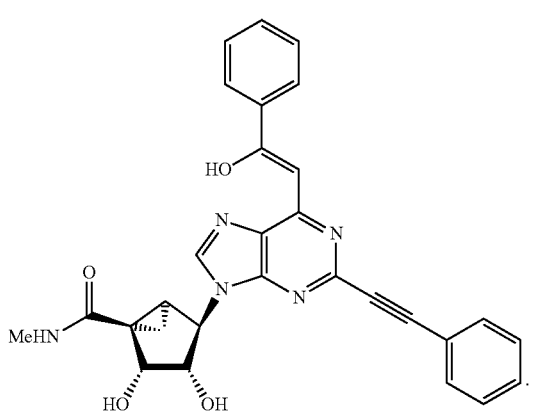

In certain embodiments, Y is CH.
In certain embodiments, $R^3$ and $R^4$ are both hydroxyl.
In certain embodiments, $R^5$ is selected from $C_1$-$C_3$ alkyl aminocarbonyl or di($C_1$-$C_3$ alkyl) aminocarbonyl.
In certain embodiments, X is NHR¹.
In certain embodiments, $R^1$ is $C_1$-$C_6$ alkyl.
In certain embodiments, $R^2$ is $C_6$-$C_{10}$ aryl, wherein the aryl group is substituted with one or more substituents selected from trifluoromethyl, hydroxyalkyl, alkoxy, and any combination thereof.
In certain other embodiments, $R^2$ is heteroaryl, and the heteroaryl group is optionally substituted with one or more substituents selected from halo, hydroxy, and alkyl.
In a particular embodiment, the compound is selected from:

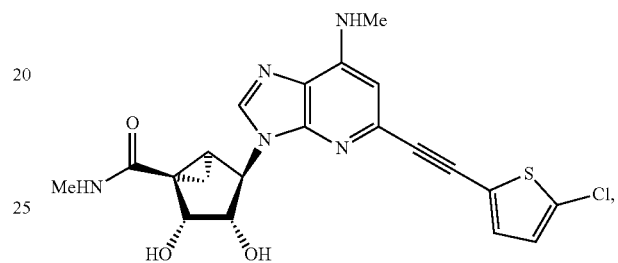

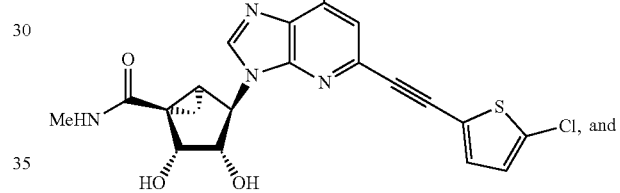

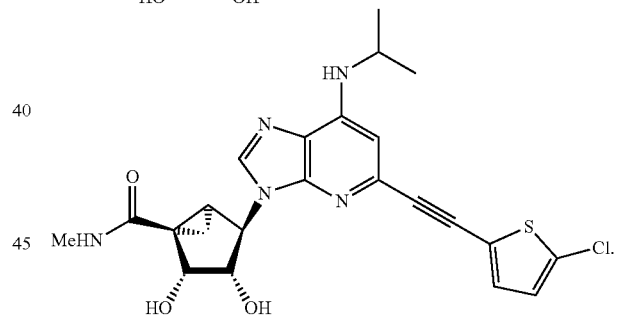

In another particular embodiment, the compound is:

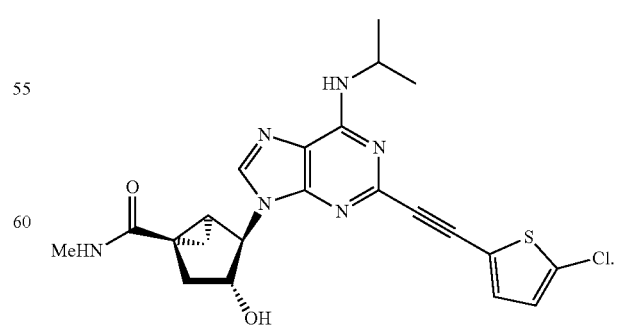

The invention also provides a compound of the formula (II):

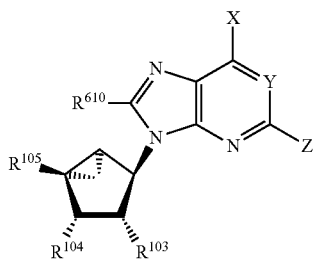

(II)

wherein X is selected from NHR$^{101}$, CH$_3$, and CH=C(R$^a$)(R$^b$) wherein R$^a$ and R$^b$ are independently selected from hydrogen, hydroxyl, C$_1$-C$_6$ alkyl, and C$_6$-C$_{14}$ aryl, Y is N or CH, R$^{101}$ is selected from C$_1$-C$_6$ alkyl, C$_1$-C$_6$ alkoxy, hydroxyl, C$_3$-C$_8$ cycloalkyl, C$_6$-C$_{14}$ aryl C$_3$-C$_8$ cycloalkyl, C$_3$-C$_8$ cycloalkyl C$_1$-C$_6$ alkyl, C$_3$-C$_8$ dicycloalkyl C$_1$-C$_6$ alkyl, C$_7$-C$_{12}$ bicycloalkyl, C$_7$-C$_{12}$ bicycloalkyl C$_1$-C$_6$ alkyl, C$_7$-C$_{14}$ tricycloalkyl C$_1$-C$_6$ alkyl, C$_6$-C$_{14}$ aryl, C$_6$-C$_{14}$ aryl C$_1$-C$_6$ alkyl, C$_6$-C$_{14}$ diaryl C$_1$-C$_6$ alkyl, C$_6$-C$_{14}$ aryl C$_1$-C$_6$ alkoxy, heterocyclyl C$_1$-C$_6$ alkyl, heterocyclyl, 4-[[[4-[[[(2-amino C$_1$-C$_6$ alkyl) amino]-carbonyl]-C$_1$-C$_6$ alkyl]anilino] carbonyl] C$_1$-C$_6$ alkyl] C$_6$-C$_{14}$ aryl, and C$_6$-C$_{14}$ aryl C$_3$-C$_8$ cycloalkyl, wherein the aryl or heterocyclyl portion of R$^1$ is optionally substituted with one or more substituents selected from halo, amino, hydroxyl, carboxy, alkoxycarbonyl, aminocarbonyl, alkylaminocarbonyl, dialkylaminocarbonyl, C$_1$-C$_6$ alkyl, C$_2$-C$_6$ alkenyl, C$_2$-C$_6$ alkynyl, C$_1$-C$_6$ alkoxy, C$_6$-C$_{14}$ aryloxy, hydroxy C$_1$-C$_6$ alkyl, hydroxy C$_2$-C$_6$ alkenyl, hydroxy C$_2$-C$_6$ alkynyl, carboxy C$_1$-C$_6$ alkyl, carboxy C$_2$-C$_6$ alkenyl, carboxy C$_2$-C$_6$ alkynyl, aminocarbonyl C$_1$-C$_6$ alkyl, aminocarbonyl C$_2$-C$_6$ alkenyl, aminocarbonyl C$_2$-C$_6$ alkynyl, and any combination thereof; and the alkyl or cycloalkyl portion of R$^{101}$ is optionally substituted with one or more substituents selected from halo, amino, alkyl, alkoxy, aryloxy, hydroxyalkyl, hydroxyalkenyl, hydroxyalkynyl, aminocarbonylalkoxy, and arylalkoxy, and any combination thereof, Z is halo, azido, or a group of the formula:

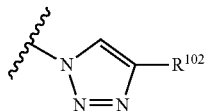

wherein R$^{102}$ is selected from C$_6$-C$_{12}$ aryl, C$_6$-C$_{12}$ aryl-C$_1$-C$_6$ alkyl, C$_3$-C$_8$ cycloalkyl, heteroaryl, and metallocenyl, wherein the aryl group is optionally substituted with one or more substituents selected from trifluoromethyl, hydroxyalkyl, alkoxy, sulfonyloxy, carboxyalkyl, sulfonyloxyalkyl, arylcarbonyl, and any combination thereof, wherein the heteroaryl group is optionally substituted with one or more substituents selected from halo, trifluoromethyl, amino, alkyl, hydroxyalkyl, aryl, alkoxy, hydroxyl, carboxyl, sulfonyloxy, carboxyalkyl, sulfonyloxyalkyl, alkylcarbonyl, arylcarbonyl, and any combination thereof, R$^{103}$ and R$^{104}$ are independently selected from hydrogen, hydroxyl, amino, mercapto, ureido, C$_1$-C$_6$ alkyl carbonylamino, hydroxy C$_1$-C$_6$ alkyl, and hydrazinyl;

R$^{105}$ is selected from hydrogen, C$_1$-C$_3$ alkyl aminocarbonyl, di(C$_1$-C$_3$ alkyl) aminocarbonyl, C$_1$-C$_3$ alkylthio C$_1$-C$_3$alkyl, halo C$_1$-C$_3$ alkyl, hydrazinyl, amino C$_1$-C$_3$ alkyl, hydroxy C$_1$-C$_3$ alkyl, C$_3$-C$_6$ cycloalkylamino, hydroxylamino, and C$_2$-C$_3$ alkenyl; and R$^{106}$ is selected from hydrogen, C$_1$-C$_6$ alkyl, C$_2$-C$_6$ alkenyl, C$_2$-C$_6$ alkynyl, heteroaryl, and C$_1$-C$_6$ aminoalkyl;

or a pharmaceutically acceptable salt thereof, with the proviso that, when R$^{103}$ and R$^{104}$ are both hydroxyl, R$^{105}$ is methylaminocarbonyl, R$^{106}$ is hydrogen, X is NHMe, and Y is CH, then Z is not iodo.

In an embodiment, R$^{106}$ is hydrogen.

In certain embodiments, Y is N.

In certain embodiments, R$^{105}$ is selected from C$_1$-C$_3$ alkyl aminocarbonyl or di(C$_1$-C$_3$ alkyl) aminocarbonyl.

In an embodiment, R$^{103}$ and R$^{104}$ are both hydroxyl.

In an embodiment, X is NHR$^{101}$. In a preferred embodiment, R$^{101}$ is C$_1$-C$_6$ alkyl.

In certain embodiments, Z is

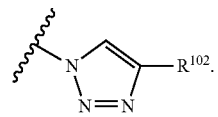

In certain embodiments, R$^{102}$ is C$_6$-C$_{10}$ aryl, wherein the aryl group is substituted with one or more substituents selected from trifluoromethyl, hydroxyalkyl, alkoxy, and any combination thereof.

In certain other embodiments, R$^{102}$ is heteroaryl, and the heteroaryl group is optionally substituted with one or more substituents selected from halo, hydroxy, and alkyl.

In certain preferred embodiments, the compound is selected from:

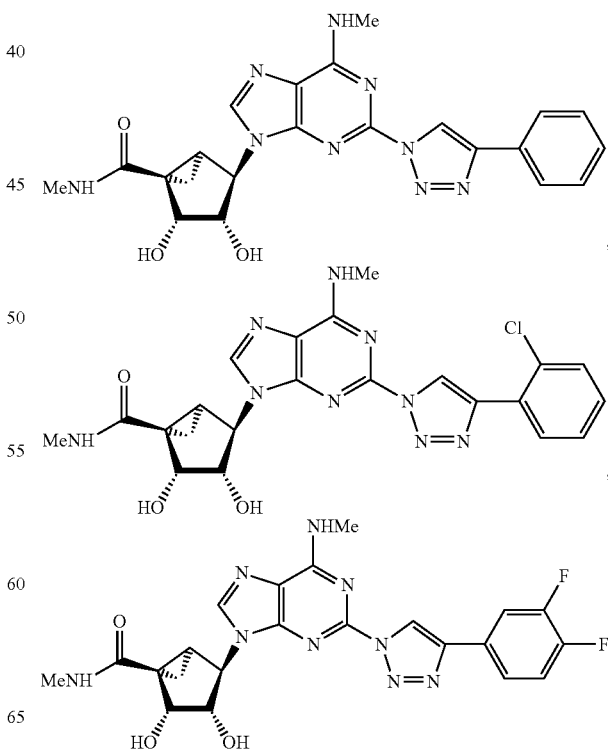

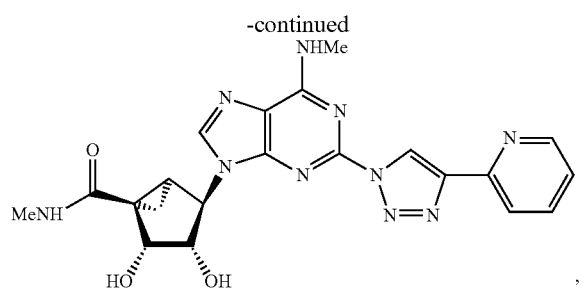
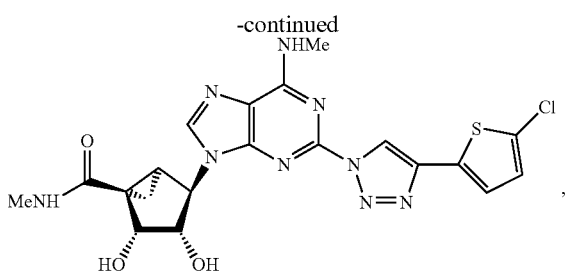
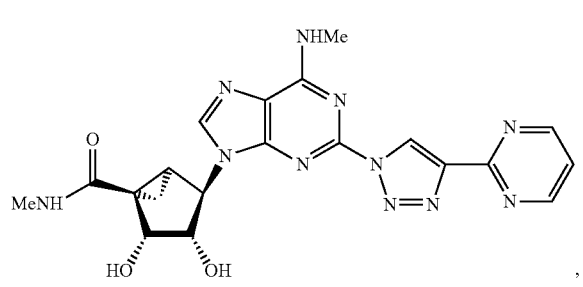
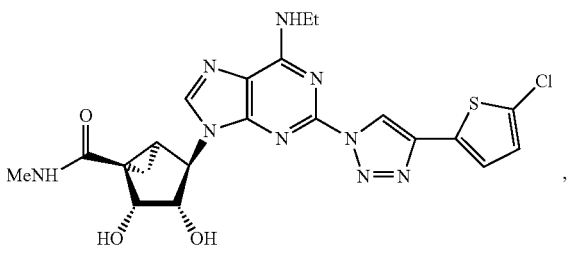
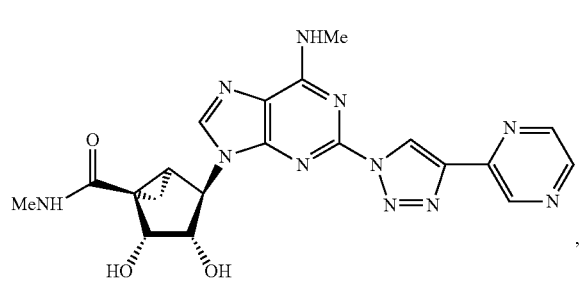
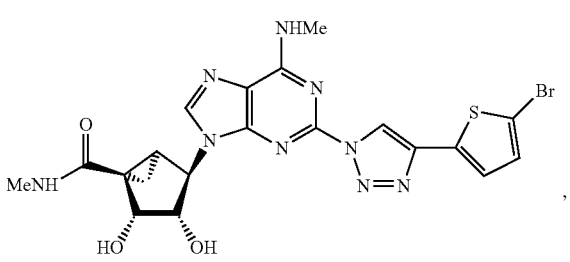
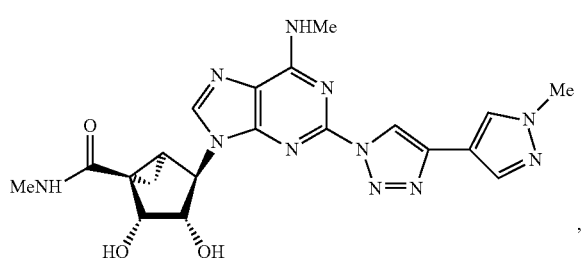
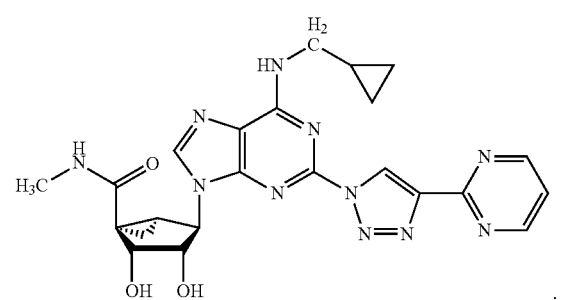
and
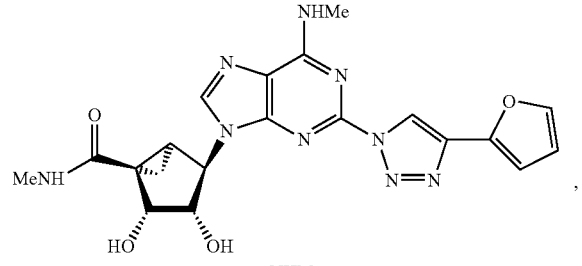
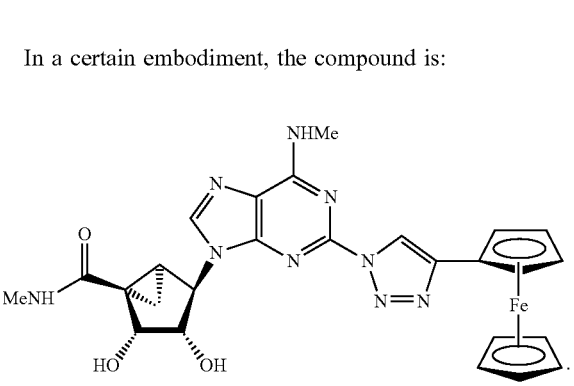
In a certain embodiment, the compound is:
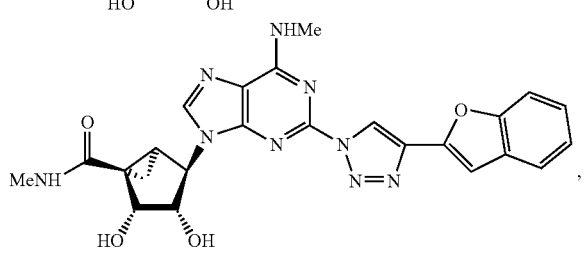
In certain preferred embodiments, the compound is selected from:

27

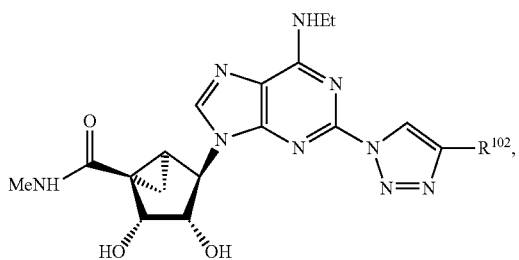

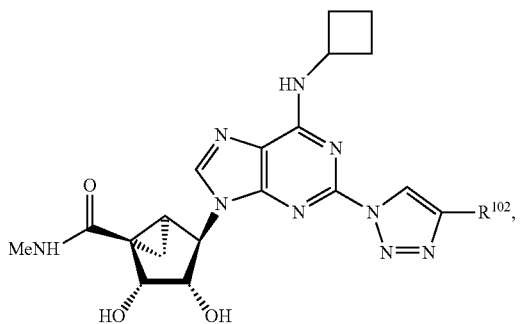

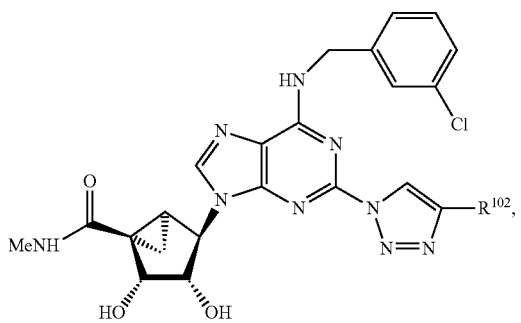

and

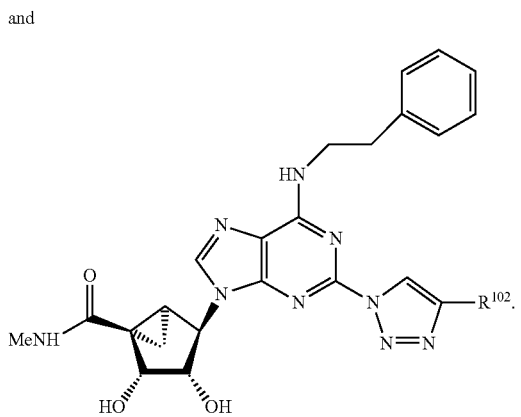

In certain of these embodiments, $R^{102}$ is $C_6$-$C_{10}$ aryl, wherein the aryl group is substituted with one or more substituents selected from trifluoromethyl, hydroxyalkyl, alkoxy, and any combination thereof.

In certain other embodiments, $R^{102}$ is heteroaryl, and the heteroaryl group is optionally substituted with one or more substituents selected from halo, hydroxy, and alkyl.

In certain preferred embodiments, the compound is selected from:

28

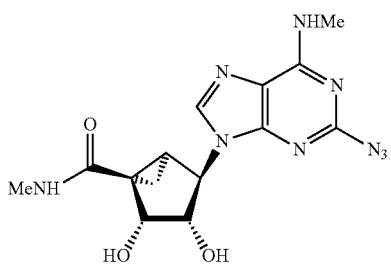

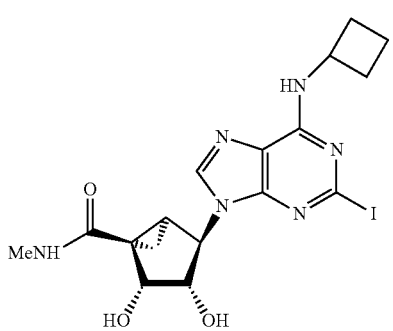

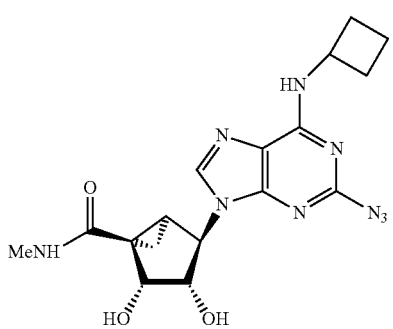

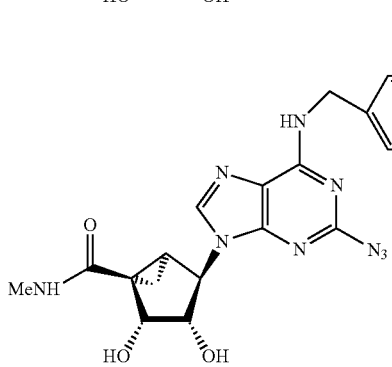

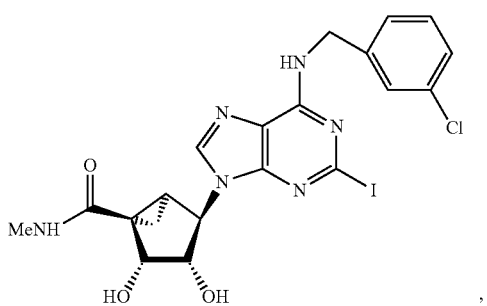

-continued

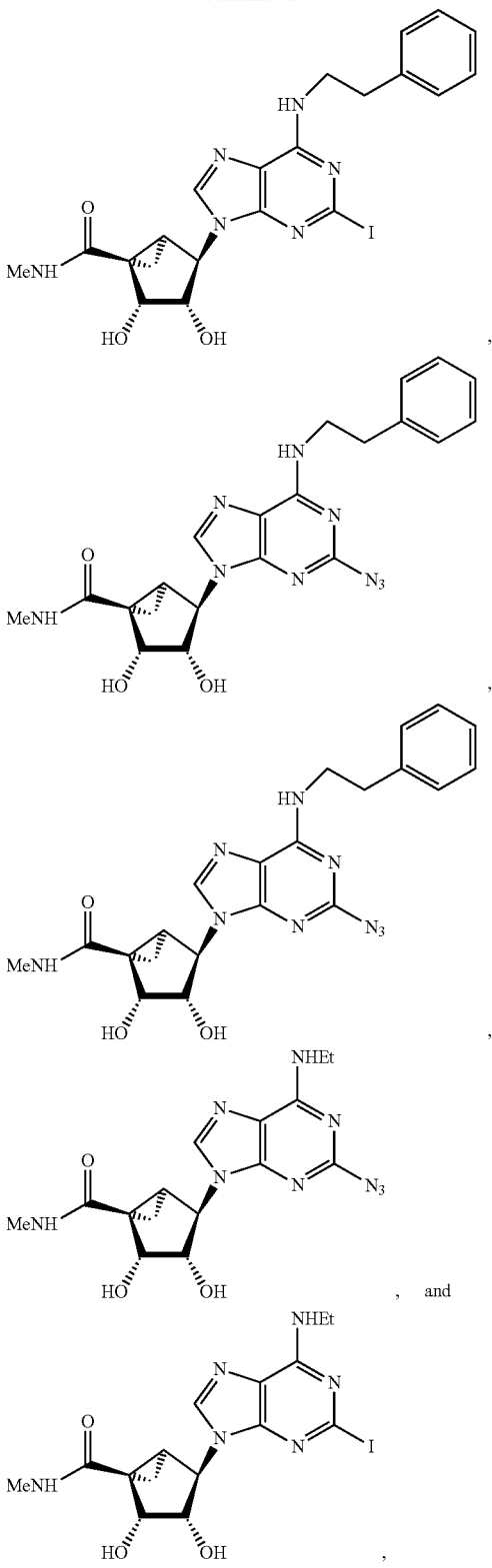

Referring now to terminology used generically herein, the term "alkyl" means a straight-chain or branched alkyl substituent containing from, for example, 1 to about 6 carbon atoms, preferably from 1 to about 4 carbon atoms, more preferably from 1 to 2 carbon atoms. Examples of such substituents include methyl, ethyl, propyl, isopropyl, n-butyl, sec-butyl, isobutyl, tert-butyl, pentyl, isoamyl, hexyl, and the like.

The term "cycloalkyl," as used herein, means a cyclic alkyl substituent containing from, for example, about 3 to about 8 carbon atoms, preferably from about 4 to about 7 carbon atoms, and more preferably from about 4 to about 6 carbon atoms. Examples of such substituents include cyclopropyl, cyclobutyl, cyclopentyl, cyclohexyl, cycloheptyl, cyclooctyl, and the like. The cyclic alkyl groups may be unsubstituted or further substituted with alkyl groups such as methyl groups, ethyl groups, and the like.

The term "heterocyclyl," as used herein, refers to a monocyclic or bicyclic 5- or 6-membered ring system containing one or more heteroatoms selected from the group consisting of O, N, S, and combinations thereof. The heterocyclyl group can be any suitable heterocyclyl group and can be an aliphatic heterocyclyl group, an aromatic heterocyclyl group, or a combination thereof. The heterocyclyl group can be a monocyclic heterocyclyl group or a bicyclic heterocyclyl group. Suitable heterocyclyl groups include morpholine, piperidine, tetrahydrofuryl, oxetanyl, pyrrolidinyl, and the like. Suitable bicyclic heterocyclyl groups include monocylic heterocyclyl rings fused to a $C_6$-$C_{10}$ aryl ring. When the heterocyclyl group is a bicyclic heterocyclyl group, both ring systems can be aliphatic or aromatic, or one ring system can be aromatic and the other ring system can be aliphatic as in, for example, dihydrobenzofuran. The term "heteroaryl" refers to a monocyclic or bicyclic 5- or 6-membered ring system as described herein, wherein the heteroaryl group is unsaturated and satisfies Hückel's rule. Non-limiting examples of suitable heteroaryl groups include furanyl, thiopheneyl, pyrrolyl, pyrazolyl, imidazolyl, 1,2,3-triazolyl, 1,2,4-triazolyl, isoxazolyl, oxazolyl, isothiazolyl, thiazolyl, 1,3,4-oxadiazol-2-yl, 1,2,4-oxadiazol-2-yl, 5-methyl-1,3,4-oxadiazole, 3-methyl-1,2,4-oxadiazole, pyridinyl, pyrimidinyl, pyrazinyl, pyridazinyl, triazinyl, benzofuranyl, benzothiopheneyl, indolyl, quinolinyl, isoquinolinyl, benzimidazolyl, benzoxazolinyl, benzothiazolinyl, and quinazolinyl. The heterocyclyl or heteroaryl group is optionally substituted with 1, 2, 3, 4, or 5 substituents as recited herein such as with alkyl groups such as methyl groups, ethyl groups, and the like, halo groups such as chloro, or hydroxyl groups, with aryl groups such as phenyl groups, naphthyl groups and the like, wherein the aryl groups can be further substituted with, for example halo, dihaloalkyl, trihaloalkyl, nitro, hydroxy, alkoxy, aryloxy, amino, substituted amino, alkylcarbonyl, alkoxycarbonyl, arylcarbonyl, aryloxycarbonyl, thio, alkylthio, arylthio, and the like, wherein the optional substituent can be present at any open position on the heterocyclyl or heteroaryl group, or with benzo groups, to form a group of, for example, benzofuran.

The term "alkylcarbonyl," as used herein, refers to an alkyl group linked to a carbonyl group and further linked to a molecule via the carbonyl group, e.g., alkyl-C(=O)—. The term "alkoxycarbonyl," as used herein, refers to an alkoxy group linked to a carbonyl group and further linked to a molecule via the carbonyl group, e.g., alkyl-O—C(=O)—.

The term "halo" or "halogen," as used herein, means a substituent selected from Group VIIA, such as, for example, fluorine, bromine, chlorine, and iodine.

The term "aryl" refers to an unsubstituted or substituted aromatic carbocyclic substituent, as commonly understood in the art, and the term "$C_6$-$C_{10}$ aryl" includes phenyl and naphthyl. It is understood that the term aryl applies to cyclic substituents that are planar and comprise 4n+2 π electrons, according to Hückel's Rule.

The term "metallocene" refers to a compound typically consisting of two cyclopentadienyl anions (Cp, which is $C_5H_5^-$) bound to a metal center (M) in the oxidation state II, with the resulting general formula $(C_5H_5)_2M$. The metal center can be Ti, V, Nb, Mo, or Fe. In a preferred embodiment, the metal center is Fe(II).

Whenever a range of the number of atoms in a structure is indicated (e.g., a $C_1$-$C_{12}$, $C_1$-$C_8$, $C_1$-$C_6$, $C_1$-$C_4$, or $C_2$-$C_{12}$, $C_2$-$C_8$, $C_2$-$C_6$, $C_2$-$C_4$ alkyl, alkenyl, alkynyl, etc.), it is specifically contemplated that any sub-range or individual number of carbon atoms falling within the indicated range also can be used. Thus, for instance, the recitation of a range of 1-8 carbon atoms (e.g., $C_1$-$C_8$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, alkylamino, etc.) referenced herein encompasses and specifically describes 1, 2, 3, 4, 5, 6, 7, 8, 9, 10, 11, and/or 12 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate). Similarly, the recitation of a range of 6-10 carbon atoms (e.g., $C_6$-$C_{10}$) as used with respect to any chemical group (e.g., aryl) referenced herein encompasses and specifically describes 6, 7, 8, 9, and/or 10 carbon atoms, as appropriate, as well as any sub-range thereof (e.g., 6-10 carbon atoms, 6-9 carbon atoms, 6-8 carbon atoms, 6-7 carbon atoms, 7-10 carbon atoms, 7-9 carbon atoms, 7-8 carbon atoms, 8-10 carbon atoms, and/or 8-9 carbon atoms, etc., as appropriate).

The phrase "pharmaceutically acceptable salt" is intended to include nontoxic salts synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, nonaqueous media such as ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, p. 1445, and *Journal of Pharmaceutical Science,* 66, 2-19 (1977).

Suitable bases include inorganic bases such as alkali and alkaline earth metal bases, e.g., those containing metallic cations such as sodium, potassium, magnesium, calcium and the like. Non-limiting examples of suitable bases include sodium hydroxide, potassium hydroxide, sodium carbonate, and potassium carbonate. Suitable acids include inorganic acids such as hydrochloric acid, hydrobromic acid, hydroiodic acid, sulfuric acid, phosphoric acid, and the like, and organic acids such as p-toluenesulfonic, methanesulfonic acid, benzenesulfonic acid, oxalic acid, p-bromophenylsulfonic acid, carbonic acid, succinic acid, citric acid, benzoic acid, acetic acid, maleic acid, tartaric acid, fatty acids, long chain fatty acids, and the like. Preferred pharmaceutically acceptable salts of inventive compounds having an acidic moiety include sodium and potassium salts. Preferred pharmaceutically acceptable salts of inventive compounds having a basic moiety (e.g., a dimethylaminoalkyl group) include hydrochloride and hydrobromide salts. The compounds of the present invention containing an acidic or basic moiety are useful in the form of the free base or acid or in the form of a pharmaceutically acceptable salt thereof.

It should be recognized that the particular counterion forming a part of any salt of this invention is usually not of a critical nature, so long as the salt as a whole is pharmacologically acceptable and as long as the counterion does not contribute undesired qualities to the salt as a whole.

It is further understood that the above compounds and salts may form solvates, or exist in a substantially uncomplexed form, such as the anhydrous form. As used herein, the term "solvate" refers to a molecular complex wherein the solvent molecule, such as the crystallizing solvent, is incorporated into the crystal lattice. When the solvent incorporated in the solvate is water, the molecular complex is called a hydrate. Pharmaceutically acceptable solvates include hydrates, alcoholates such as methanolates and ethanolates, acetonitrilates and the like. These compounds can also exist in polymorphic forms.

In any of the above embodiments, the compound or salt of formula (I) can have at least one asymmetric carbon atom. When the compound or salt has at least one asymmetric carbon atom, the compound or salt can exist in the racemic form, in the form of its pure optical isomers, or in the form of a mixture wherein one isomer is enriched relative to the other. In particular, in accordance with the present invention, when the inventive compounds have a single asymmetric carbon atom, the inventive compounds may exist as racemates, i.e., as mixtures of equal amounts of optical isomers, i.e., equal amounts of two enantiomers, or in the form of a single enantiomer. As used herein, "single enantiomer" is intended to include a compound that comprises more than 50% of a single enantiomer (i.e., enantiomeric excess up to 100% pure enantiomer).

When the compound or salt has more than one chiral center, the compound or salt can therefore exist as a mixture of diastereomers or in the form of a single diastereomer. As used herein, "single diastereomer" is intended to mean a compound that comprises more than 50% of a single diastereomer (i.e., diastereomeric excess to 100% pure diastereomer).

The present invention further provides a pharmaceutical composition comprising a compound as described above and a pharmaceutically acceptable carrier. The present invention provides a pharmaceutical composition comprising a pharmaceutically acceptable carrier and an effective amount, e.g., a therapeutically effective amount, including a prophylactically effective amount, of one or more of the aforesaid compounds, or salts thereof, of the present invention.

The pharmaceutically acceptable carrier can be any of those conventionally used and is limited only by chemico-physical considerations, such as solubility and lack of reactivity with the compound, and by the route of administration. It will be appreciated by one of skill in the art that, in addition to the following described pharmaceutical compositions; the compounds of the present invention can be formulated as inclusion complexes, such as cyclodextrin inclusion complexes, or liposomes.

The pharmaceutically acceptable carriers described herein, for example, vehicles, adjuvants, excipients, or diluents, are well known to those who are skilled in the art and are readily available to the public. It is preferred that the pharmaceutically acceptable carrier be one which is chemically inert to the active compounds and one which has no detrimental side effects or toxicity under the conditions of use.

The choice of carrier will be determined in part by the particular active agent, as well as by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, interperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

The compounds of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (3) mixtures thereof.

The parenteral formulations will typically contain from about 0.5 to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The compounds of the present invention may be made into injectable formulations. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238-250 (1982), and *ASHP Handbook on Injectable Drugs*, Toissel, 4th ed., pages 622-630 (1986).

Topical formulations, including those that are useful for transdermal drug release, are well-known to those of skill in the art and are suitable in the context of the invention for application to skin. Topically applied compositions are generally in the form of liquids, creams, pastes, lotions and gels. Topical administration includes application to the oral mucosa, which includes the oral cavity, oral epithelium, palate, gingival, and the nasal mucosa. In some embodiments, the composition contains at least one active component and a suitable vehicle or carrier. It may also contain other components, such as an anti-irritant. The carrier can be a liquid, solid or semi-solid. In embodiments, the composition is an aqueous solution. Alternatively, the composition can be a dispersion, emulsion, gel, lotion or cream vehicle for the various components. In one embodiment, the primary vehicle is water or a biocompatible solvent that is substantially neutral or that has been rendered substantially neutral. The liquid vehicle can include other materials, such as buffers, alcohols, glycerin, and mineral oils with various emulsifiers or dispersing agents as known in the art to obtain the desired pH, consistency and viscosity. It is possible that the compositions can be produced as solids, such as powders or granules. The solids can be applied directly or dissolved in water or a biocompatible solvent prior to use to form a solution that is substantially neutral or that has been rendered substantially neutral and that can then be applied to the target site. In embodiments of the invention, the vehicle for topical application to the skin can include water, buffered solutions, various alcohols, glycols such as glycerin, lipid materials such as fatty acids, mineral oils, phosphoglycerides, collagen, gelatin and silicone based materials.

Additionally, the compounds of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

Chemistry

Representative routes to the compounds of the invention, for example, those set forth in Tables 1 and 2, are described below. The synthetic methods depicted in Schemes 1-4 begin with 6-Chloro 5'-ethyl ester intermediate 52 which was prepared from L-ribose 51 as previously described (Paoletta, S. et al., *J. Med. Chem.*, 2013, 56: 5949-5963; Tosh, D. K. et al., *J. Med. Chem.* 2012, 55: 4847-4860; and Tosh, D. K. et al., *Med. Chem. Comm.*, 2013, 4: 619-630). 6-Chloro 5'-ethyl ester intermediate 52 was treated with MeNH$_2$.HCl in the presence of Et$_3$N in methanol and the resulting compound was treated with a 40% methylamine solution (aqueous) at room temperature to provide intermediate 53 for the N$^6$-methyl derivatives (Scheme 1). In the case of N$^6$-(2-phenylcyclopropyl) derivatives, 52 was sequentially treated with the appropriate 2-phenylcyclopropylamine to yield 55a-f followed by methylamine to provide 56a-f (Scheme 2). Then, intermediates 53 and 56 were subjected to Sonogashira coupling with the appropriate aryl- or cycloalkylacetylene in the presence of PdCl$_2$(Ph$_3$P)$_2$, CuI and triethylamine to give protected intermediates 54 and 57, respectively. Finally, hydrolysis of the isopropylidene protecting group afforded the nucleoside target compounds for biological testing.

Scheme 1. Synthesis of N$^6$-methyl derivatives.

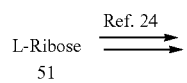

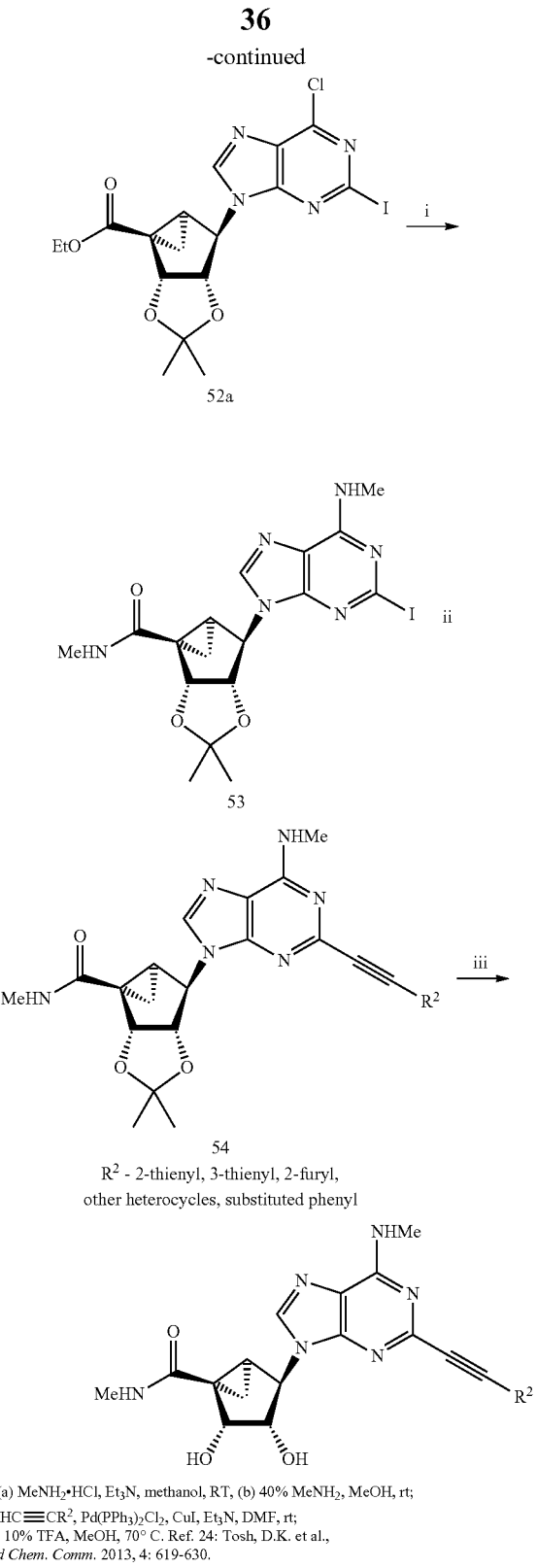

(i) (a) MeNH$_2$•HCl, Et$_3$N, methanol, RT, (b) 40% MeNH$_2$, MeOH, rt;
(ii) HC≡CR$^2$, Pd(PPh$_3$)$_2$Cl$_2$, CuI, Et$_3$N, DMF, rt;
(iii) 10% TFA, MeOH, 70° C. Ref. 24: Tosh, D.K. et al., *Med Chem. Comm.* 2013, 4: 619-630.

Scheme 2. Synthesis of N$^6$-phenylcyclopropyl derivatives.

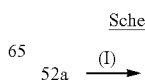

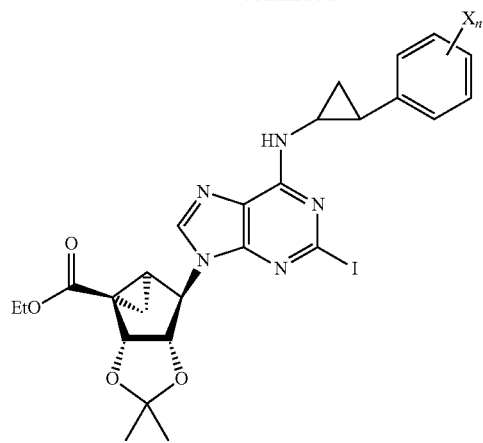

55a-f

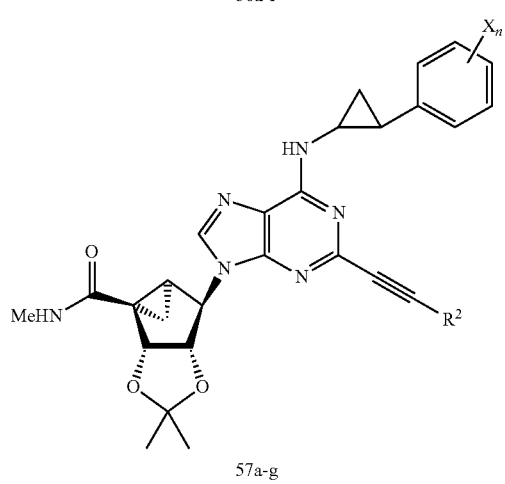

56a-f

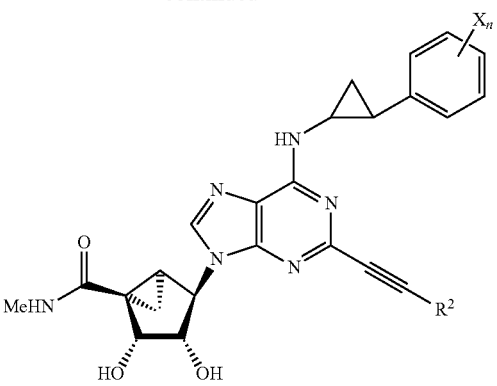

(i) X_n-penylcyclopropyl-H$_2$, Et$_3$N, MeOH, rt;
(ii) 40% MeNH$_2$, MeOH, rt;
(iii) HC≡CR$^2$, Pd(PPh$_3$)$_2$Cl$_2$, CuI, Et$_3$N, DMF, rt;
(iv) 10% TFA, MeOH, 70° C.

A synthesis of (N)-methanocarba purine 5'-methyluronamides of the invention containing 2-arylethynyl groups and 6-alkyl and styryl substituents is shown in Scheme 3. Sonogashira coupling of the 2-iodo derivative 52a with the appropriate arylacetylene in the presence of PdCl$_2$(Ph$_3$P)$_2$, CuI and triethylamine gave the doubly substituted intermediates 58. Upon attempted selective reaction of the 5'-ester with methylamine, it was found that the C6-alkynyl group also reacted with methylamine to give a styryl adduct 59. Upon attempted hydrolysis of the isopropylidene group of 59 with 10% TFA/water, styrenol derivatives 38, 40, and 42 were obtained along with a styrenol-truncated C6-methyl compound 39 and 41 in some of the cases. These side products (shown to have their own biological activities) were formed via an unanticipated rearrangement. Similarly the hydroxystyryl derivative 43 in the C2-chloro series was prepared by a route involving intermediates 52b, 60 and 61.

Scheme 3. Synthesis of C6-methyl and C6-styryl derivatives.

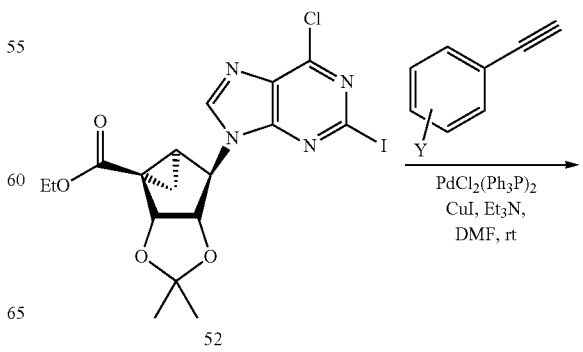

52

57a-g
R$^2$ = phenyl, 2-pyridyl
a X = H
b X = 3-Me
c X = 3-F
d X = 3-Cl
e X = 3-Br
f X = 3,4-diF
g X = 3,4-diF
n = 1-5

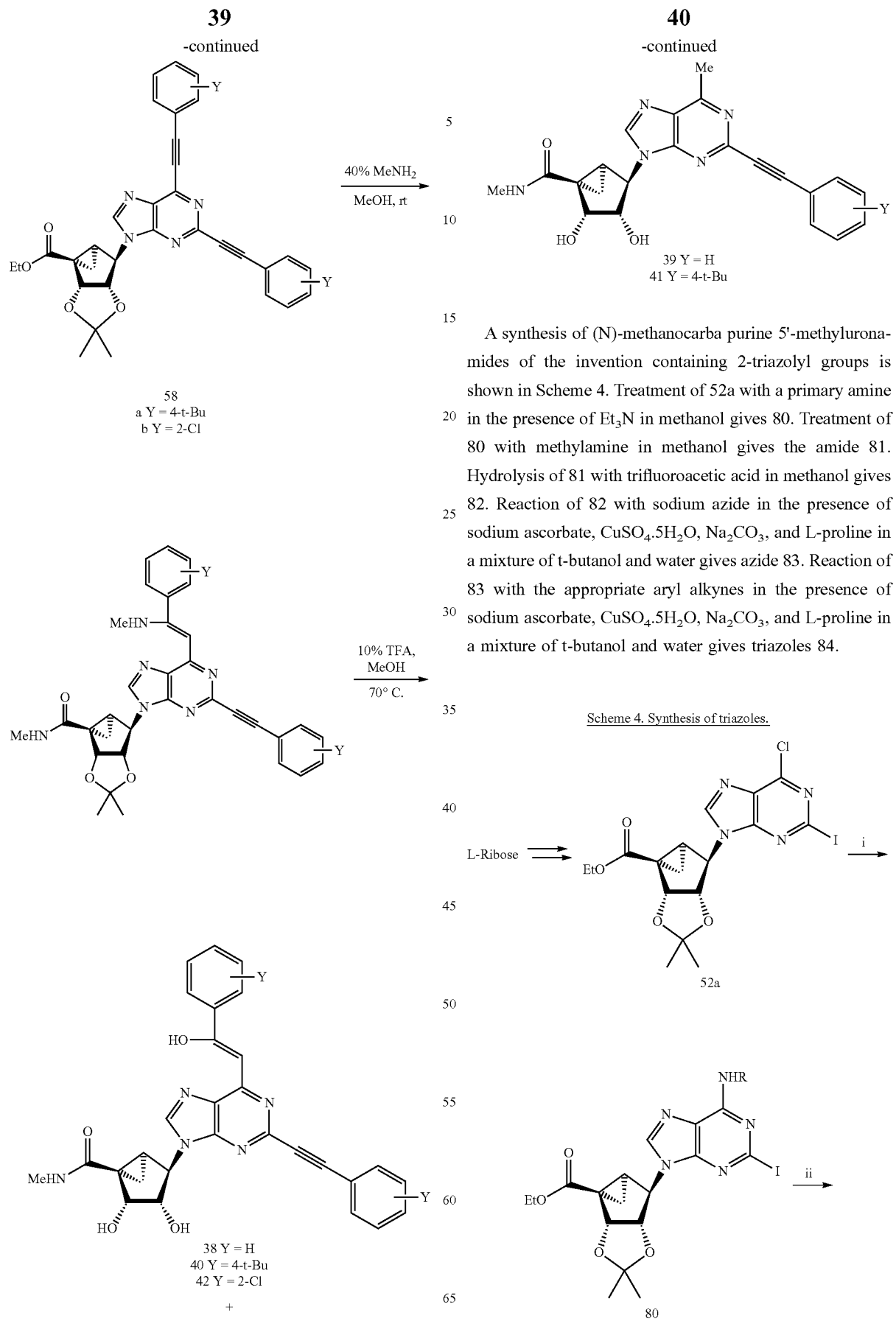

A synthesis of (N)-methanocarba purine 5'-methyluronamides of the invention containing 2-triazolyl groups is shown in Scheme 4. Treatment of 52a with a primary amine in the presence of Et₃N in methanol gives 80. Treatment of 80 with methylamine in methanol gives the amide 81. Hydrolysis of 81 with trifluoroacetic acid in methanol gives 82. Reaction of 82 with sodium azide in the presence of sodium ascorbate, CuSO₄.5H₂O, Na₂CO₃, and L-proline in a mixture of t-butanol and water gives azide 83. Reaction of 83 with the appropriate aryl alkynes in the presence of sodium ascorbate, CuSO₄.5H₂O, Na₂CO₃, and L-proline in a mixture of t-butanol and water gives triazoles 84.

-continued

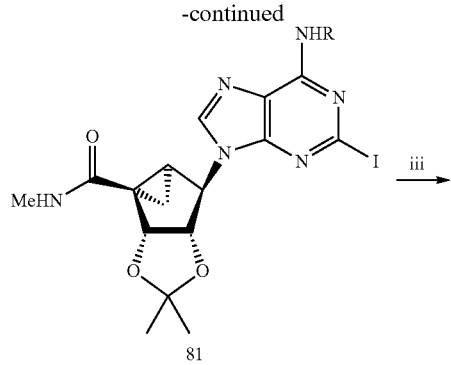
81

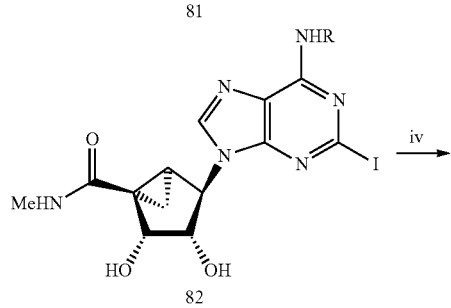
82

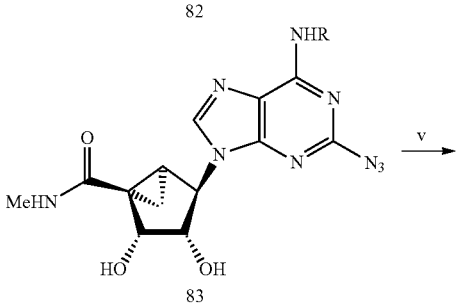
83

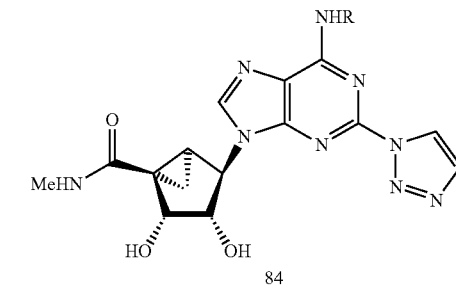
84

Scheme 5. Synthesis of deaza analogs.

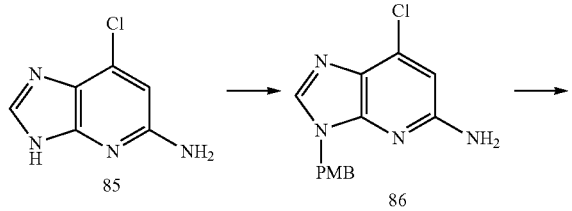

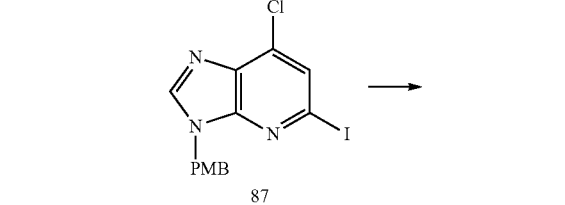
87

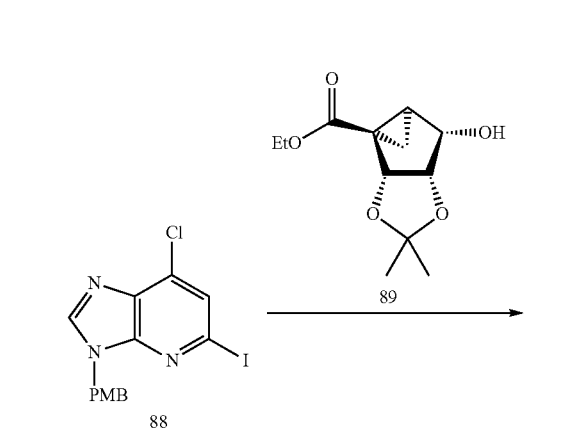

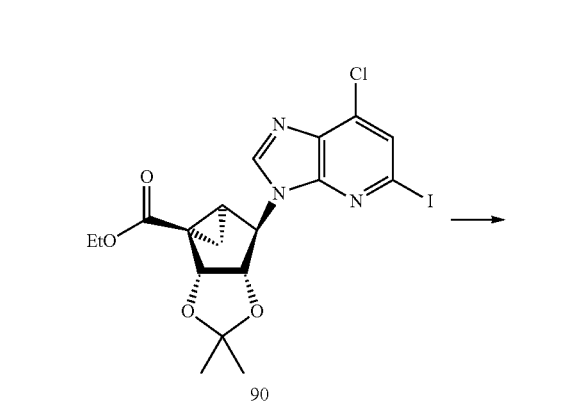
90

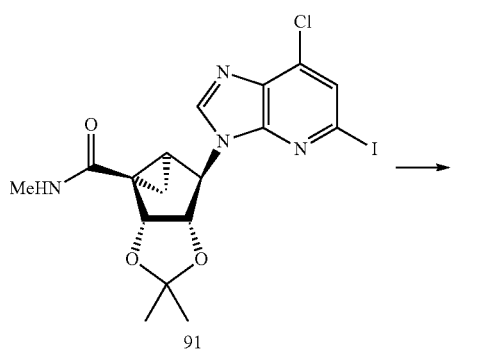
91

A synthesis of deaza analogs of (N)-methanocarba purine 5'-methyluronamides of the invention containing 2-triazolyl groups is shown in Scheme 5. 1-Deaza-6-chloro-2-iodopurine 88 was prepared from the corresponding amino compound 85 via a sequence of protection of the imidazo nitrogen with a p-methoxybenzyl group using p-methoxybenzyl chloride in DMF to give 86, reaction of 86 with isoamyl nitrite, methylene iodide, and cuprous iodide in THF to give 87, and deprotection of 87 with TFA gave 88. Reaction of 88 with 89 (derived from L-ribose) in the presence of triphenylphosphine and diisopropylazodicarboxylate in THF gave 90. The 5'-ethyl ester compound 90 was treated with aqueous methylamine to give amide 91. Treatment of 91 with MeNH$_2$HCl in the presence of diisopropylethylamine in isopropanol under microwave irradiation gave 92. Sonogashira coupling of 92 with 5-chloro-2-ethynylthiophene in the presence of PdCl$_2$(Ph$_3$P)$_2$, CuI, and Et3N in DMF gave 93, which was deprotected with TFA in methanol to give compound 127.

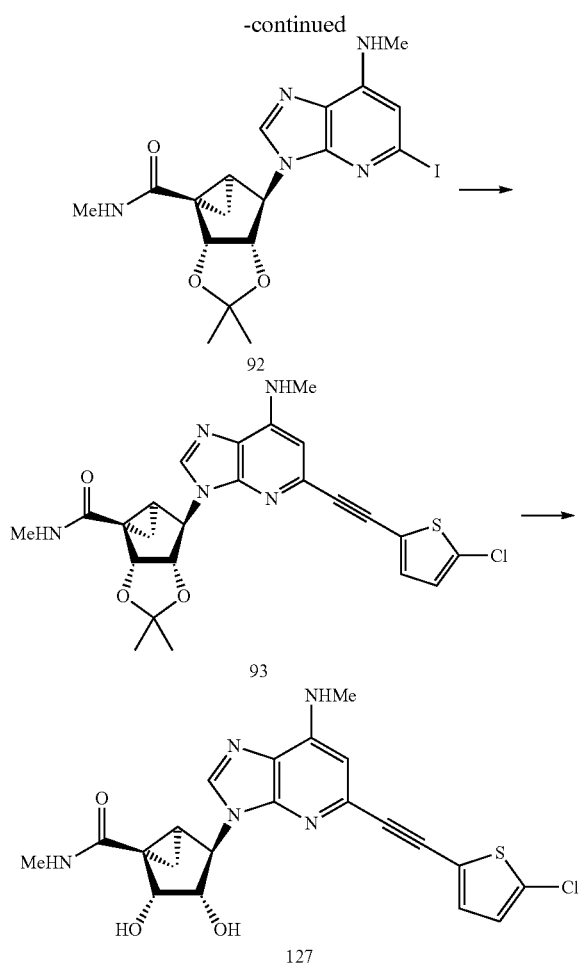

In certain embodiments, the invention provides a method of treating or preventing a disease, state or condition in a patient in need thereof comprising administering to the patient an effective amount of a compound of any one of embodiments of the invention or a pharmaceutically acceptable salt thereof, wherein the disease, state or condition is selected from the group consisting of neuropathic pain, vascular inflammation, arthritis, allergies, asthma, wound healing, stroke, cardiac failure, acute spinal cord injury, acute head injury or trauma, seizure, neonatal hypoxia, cerebral palsy, chronic hypoxia due to arteriovenous malformations and occlusive cerebral artery disease, ischemia and reperfusion injury in skeletal muscle, severe neurological disorders related to excitotoxicity, Parkinson's disease, Huntington's chorea, diseases of the CNS, cardiac disease, kidney disease, glaucoma, cancer, neuropathic pain, neuropathic pain associated with diabetes, transient ischemic attacks, myeloprotection, dry eye syndrome, osteoarthritis, rheumatoid arthritis, loss of skin pigmentation, inflammatory bowel disease, pulmonary inflammation, uveitis, and septic shock. In a preferred embodiment, the invention provides a method of treating or preventing neuropathic pain in a patient in need thereof. In another preferred embodiment, the invention provides a method of treating or preventing postoperative pain in a patient in need thereof.

In an embodiment, the compounds of the invention may also be used to treat pain associated with chemotherapy-induced peripheral neuropathy (CIPN) induced by one or more combinations comprising a chemotherapeutic drug as part of a treatment regimen. Non-limiting examples of suitable combinations include CHOPP (cyclophosphamide, doxorubicin, vincristine, prednisone, and procarbazine); CHOP (cyclophosphamide, doxorubicin, vincristine, and prednisone); COP (cyclophosphamide, vincristine, and prednisone); CAP-BOP (cyclophosphamide, doxorubicin, procarbazine, bleomycin, vincristine, and prednisone); m-BACOD (methotrexate, bleomycin, doxorubicin, cyclophosphamide, vincristine, dexamethasone, and leucovorin); ProMACE-MOPP (prednisone, methotrexate, doxorubicin, cyclophosphamide, etoposide, leucovorin, mechloethamine, vincristine, prednisone, and procarbazine); ProMACE-CytaBOM (prednisone, methotrexate, doxorubicin, cyclophosphamide, etoposide, leucovorin, cytarabine, bleomycin, and vincristine); MACOP-B (methotrexate, doxorubicin, cyclophosphamide, vincristine, prednisone, bleomycin, and leucovorin); MOPP (mechloethamine, vincristine, prednisone, and procarbazine); ABVD (adriamycin/doxorubicin, bleomycin, vinblastine, and dacarbazine); MOPP (mechloethamine, vincristine, prednisone and procarbazine) alternating with ABV (adriamycin/doxorubicin, bleomycin, and vinblastine); MOPP (mechloethamine, vincristine, prednisone, and procarbazine) alternating with ABVD (adriamycin/doxorubicin, bleomycin, vinblastine, and dacarbazine); ChIVPP (chlorambucil, vinblastine, procarbazine, and prednisone); IMVP-16 (ifosfamide, methotrexate, and etoposide); MIME (methyl-gag, ifosfamide, methotrexate, and etoposide); DHAP (dexamethasone, high-dose cytaribine, and cisplatin); ESHAP (etoposide, methylpredisolone, high-dose cytarabine, and cisplatin); CEPP(B) (cyclophosphamide, etoposide, procarbazine, prednisone, and bleomycin); CAMP (lomustine, mitoxantrone, cytarabine, and prednisone); CVP-1 (cyclophosphamide, vincristine, and prednisone), ESHOP (etoposide, methylpredisolone, high-dose cytarabine, vincristine and cisplatin); EPOCH (etoposide, vincristine, and doxorubicin for 96 hours with bolus doses of cyclophosphamide and oral prednisone), ICE (ifosfamide, cyclophosphamide, and etoposide), CEPP(B) (cyclophosphamide, etoposide, procarbazine, prednisone, and bleomycin), CHOP—B (cyclophosphamide, doxorubicin, vincristine, prednisone, and bleomycin), CEPP-B (cyclophosphamide, etoposide, procarbazine, and bleomycin), and P/DOCE (epirubicin or doxorubicin, vincristine, cyclophosphamide, and prednisone).

In an embodiment, a method of treating neuropathic pain in a subject, comprising administering to the subject a compound of the invention in conjunction with an analgesic, is provided. This embodiment is based on the discovery that the compound of the invention and analgesics exhibit a synergistic effect increasing the potency of the analgesics. In other words, the administration of these compounds exhibits synergistic effects that exceed the mere additive contribution of the individual components. As a result, synergistically effective amounts of the compound of the invention and analgesic taken together may be less than the effective amount of the compound of the invention or analgesic administered as monotherapies.

The method may involve administering to a subject a first amount of a compound of the invention in combination with a second amount of analgesic, wherein the first and second amount together comprise a pharmaceutically effective amount. Because of the above synergistic effect, the first amount, the second amount, or both may be less than effective amounts of each compound administered as monotherapies. Therapeutically effective amounts of the compound of the invention and analgesic are co-administered to the subject, i.e., are administered to the subject simultaneously or separately, in any given order and by the same or different routes of administration. It may be advantageous to initiate administration of the compound of the invention first, for example one or more days or weeks prior to initiation of administration of the analgesic. Moreover, additional drugs may be given in conjunction with the above combination therapy.

The method of this embodiment may be used to alleviate the symptoms of neuropathic pain regardless of the cause of the pain, for example, but not limited to, spinal cord injury, multiple sclerosis, stroke, diabetes, herpes zoster infection, HIV-related neuropathies, nutritional deficiencies, toxins, remote manifestations of malignancies, genetic, immune mediated disorders or physical trauma to a nerve trunk, cancer, chemotherapy, radiation injury or surgery (e.g., postoperative pain), vulvodynia, and burning mouth syndrome. In an embodiment, the neuropathic pain is associated with chronic use of opioids.

The analgesic administered in conjunction with the compound of the invention may be selected in relation to the particular condition being treated, and preferably has proven efficacy in the treatment of pain without significant potential for addiction. Currently known analgesics include, but are not limited to, opioids, morphinomimetics, antidepressants, antiepileptics, NMDA receptor antagonists, fatty acid amine hydrolyase inhibitors, anticonvulsives, non-steroidal anti-inflammatory drugs (NSAIDs), COX-2 inhibitors, NOS inhibitors, acetaminophen, and calcium channel subunit $\alpha_2\delta$ ligands.

Example opioids include any natural or synthetic opioid analgesic, such as morphine, fentanyl, codeine, thebaine, diacetylmorphine (heroin), dihydrocodeine, hydrocodone, hydromorphone, nicomorphine, oxycodone, oxymorphone, alphamethylfentanyl, alfentanil, sufentanil, remifentanil, carfentanyl, ohmefentanyl, nocaine, pethidine (meperidine), ketobemidone, MPPP, allylprodine, prodine, PEPAP, propoxyphene, dextropropoxyphene, dextromoramide, bezitramide, piritramide, methadone, dipipanone, levoalphacetylmethadol (LAAM), loperamide, diphenoxylate, pentazocine, phenazocine, buprenorphine, etorphine, butorphanol, nalbuphine, levorphanol, levomethorphan, dezocine, lefetamine, tilidine, tramadol, propoxyphene, and oxycodone. As intended herein, an opioid also encompasses any natural or synthetic narcotic antagonist such as nalmefene, naloxone or naltrexone as well as any natural or synthetic mixed opioid agonist/antagonist such as nalbuphine, butorphanol, buprenorphine and pentazocine.

Example non-steroidal anti-inflammatory drugs (NSAIDs) include aspirine, ibuprofen, acetaminophen, naproxen, fenoprofen, ketoprofen, flurbiprofen, oxaprozin, indomethacin, sulindac, etodolac, ketorolac, diclofenac, nabumetone, piroxicam, meloxicam, tenoxicam, droxicam, lornoxicam, isoxicam, mefenamic acid, meclofenamic acid, flufenamic acid, tolfenamic acid, celecoxib, rofecoxib, valdecoxib, parecoxib, lumiracoxib, etoricoxib, firocoxib, nimesulide, and licofelone. Example antidepressants include tricyclic antidepressants such as: amitriptyline, amitriptylinoxide, butriptyline, clomipramine, demexiptiline, desipraminc, dibenzepin, dimetacrine, dosulepin, doxepin, imipramine, imipraminoxide, lofepramine, melitracen, metapramine, nitroxazepine, nortriptyline, noxiptiline, pipofezine, propizepine, protriptyline, and quinupramine; amineptine, norepinephrine, iprindole, opipramol, tianeptine, trimipramine, carbamezapine, and flupirtine.

It is contemplated that a compound of the invention will be especially suited to the treatment of pain when co-administered with an opioid, a tricyclic antidepressant, or an analgesic believed to bind the calcium channel subunit $\alpha_2\delta$, i.e. a calcium channel subunit $\alpha_2\delta$ ligand. Examples of such ligands include GABA analogs, such as gabapentin (2-[1-(aminomethyl)cyclohexyl]acetic acid) and pregabalin ((S)-3-(aminomethyl)-5-methylhexanoic acid).

The relative amounts of the compounds may be selected to provide for synergistic pain relief. For example, a suitable ratio of a compound of the invention to gabapentin may be in the range of from about 0.1 part by weight of the compound to from about 3 to about 30 parts by weight of the gabapentin. A suitable ratio of a compound of the invention to morphine may be in the range of from about 0.1 part by weight of the compound to from about 1 to about 5 parts by weight of the morphine. While these ratios are calculated with respect to the free compounds (non-salt forms), it should be understood that the equivalent ratios can also readily be determined for pharmaceutically acceptable salts or prodrugs of the compounds by using a ratio of the molecular weights of the salts.

In some cases, co-administration of the compound of the invention and analgesic is achieved by formulating the compounds together in a combination composition. Accordingly, in a third aspect, a combination composition for treating neuropathic pain is provided.

The analgesic administered in the combination composition may be selected in relation to the particular condition being treated, and preferably has proven efficacy in the treatment of pain without significant potential for addiction. Currently known analgesics include, but are not limited to, opioids, morphinomimetics, antidepressants, antiepileptics, NMDA receptor antagonists, fatty acid amine hydrolyase inhibitors, anticonvulsives, non-steroidal anti-inflammatory drugs (NSAIDs), COX-2 inhibitors, NOS inhibitors, calcium channel subunit $\alpha_2\delta$ ligands, sodium channel antagonists, and cannabinoids.

In some cases, the combination composition comprises a first pharmaceutically acceptable composition containing a first amount of a compound of the invention, and a second pharmaceutically acceptable composition comprising a second amount of an analgesic, wherein the first and second amounts taken together comprise a pharmaceutically effective amount. The first amount, the second amount, or both may be less than effective amounts of each compound administered as monotherapies.

In other cases, the combination composition is a pharmaceutically acceptable composition comprising a first amount of a compound of the invention and a second amount of an analgesic, wherein the first and second amounts taken together comprise a pharmaceutically effective amount. The first amount, the second amount, or both may be less than effective amounts of each compound administered as monotherapies.

In an embodiment, the invention provides a method of reducing opioid antinociceptive tolerance and/or hypersensitivity in a subject receiving opiate therapy for acute/severe and chronic neuropathic (malignant and non malignant) pain comprising administering to the subject an amount of a compound of the invention sufficient to reduce opioid antinociceptive tolerance. The opioid may be morphine, oxycodone, or fentanyl. The subject may be a human or a non-human mammal. The nociceptive pain may be chronic pain or acute pain. The nociceptive pain may be the result of an injury, such as a penetration wound, a burn, frostbite or a fracture. The nociceptive pain may be the result of a disease, such as diabetes (e.g., diabetic neuropathy), post-surgical pain, bone cancer pain, breast cancer pain, traumatic pain, spinal nerve injuries, multiple sclerosis, arthritis, an autoimmune disease, or an infection.

The opiate and compound of the invention may be delivered at the same time, and may be co-formulated or not co-formulated. Alternatively, the opiate and the compound of the invention may be delivered at distinct times, such as where the opioid is delivered before the compound of the invention, or after the compound of the invention. The opiate and compound of the invention may be delivered in alternating administrations. The compound of the invention and/or the opiate may be delivered over a period of one week, two weeks, three weeks, four weeks, one month, two months, three months, four months, five months, six months, seven months, eight months, nine months, ten months, eleven months, one year, two years or three years. The opiate and/or the compound of the invention may be delivered by continuous infusion, such as by an implanted pump.

In another embodiment, there is provided a method of preventing or treating opioid dependence (i.e., withdrawal in a subject receiving opiates comprising administering to the subject an amount of a compound of the invention sufficient to treat one or more symptons of opioid withdrawal. The opioid may be morphine, oxycodone, fentanyl, cocaine herion, or opium. The subject may be is a human or a non-human mammal. The patient may have received treatment for pain, such as chronic or acute pain. The acute pain may be the result of an injury, such as a penetration wound, a burn, frostbite or a fracture. The chronic pain is the result of a disease, such as arthritis, an autoimmune disease, or an infection.

The compound of the invention may be delivered prior to initiating withdrawal or after initiating withdrawal. The compound of the invention may be co-administered with a decreasing dosage of opiate. The compound of the invention may be delivered prior to beginning opiate therapy. The compound of the invention may be delivered for a period of time after the opiate is no longer administered to the subject. The compound of the invention may be delivered over a period of one week, two weeks, three weeks, four weeks, one month, two months, three months, four months, five months, or six months after the opiate is no longer administered to the subject. The opiate and/or the compound of the invention may be delivered by continuous infusion, such as by an implanted pump.

The subject may be an abuser of illegal or illegally obtained opiate. The one or more symptoms may comprise agitation, anxiety, muscle ache, increased tearing, insomnia, runny nose, sweating, and yawning, while late symptoms of withdrawal include abdominal cramping, diarrhea, dilated pupils, goose bumps, nausea and/or vomiting. The method may further comprise subjecting the subject to a drug treatment program, such as methadone treatment or buprenorphine treatment.

Adenosine has been implicated in mediating unwanted side effects of chronic opioid administration such as dependence and reward. For example, chronic administration of opioids has been reported to decrease the extracellular levels of adenosine and its signaling at $A_1AR$ in the brainstem, a phenomenon linked to dependence/addiction; thus, $A_1AR$ agonists or AdK inhibitors attenuate behavioral evidence of naloxone-induced opioid withdrawal, whereas $A_1AR$ antagonists exacerbated opioid withdrawal effect Other addictive drugs such as amphetamine and cocaine, like opioids, are known to modulate adenosine levels in the CNS, which contribute to the pathophysiology of addiction-related disorders; of note, glia activation in the CNS plays a role in their rewarding and dependence aspects. However, the existing literature and scientific focus in this context has been on $A_1AR$ and the $A_{2A}R$ signaling; nothing is known about the $A_3AR$'s contribution. It has been reported that $A_3AR$ agonists such as IB-MECA block opioid dependence (naloxone-precipitated withdrawal in morphine-dependent rats, U.S. patent application Ser. No. 14/496,030). It has been demonstrated that $A_3AR$ agonists, such as MRS5980, block opioid-induced hypersensitivity and analgesic tolerance. These findings are quite significant as they establish the contribution of an adenosine to $A_3AR$ system in neurobiological pathways associated with drug of abuse substances while raising the intriguing possibility that targeting the $A_3AR$ axis may produce far-reaching opportunities to address critical issues associated with drugs of abuse.

In other embodiments, the compound of the invention is administered in conjunction with agents such as TNF-α inhibitors, IL-1β inhibitors, p38 kinase inhibitors, ERK inhibitors, JNK inhibitors, modulators of transcription factors such as NF-κB, agents that modulate glial cell function, agents that block expression and/or activity of adenosine kinase, recombinant ectonucleotidases, ENT inhibitors, and the like. Non-limiting examples of p38 kinase inhibitors include PH-797804, BIRB 796, VX-702, SB 239063, SB202190, SCIO 469, and BMS 582949. An example of an ERK inhibitor is sorafenib. An example of a JNK inhibitor is AM-111. Non-limiting examples of NF-κB modulators include disulfiram, olmesartan, dithiocarbamates, and anatabine.

The compounds or salts thereof can be used in any suitable dose. Suitable doses and dosage regimens can be determined by conventional range finding techniques. Generally treatment is initiated with smaller dosages, which are less than the optimum dose. Thereafter, the dosage is increased by small increments until optimum effect under the circumstances is reached. For convenience, the total daily dosage may be divided and administered in portions during the day if desired. In proper doses and with suitable administration of certain compounds, the present invention provides for a wide range of responses. Typically the dosages range from about 0.001 to about 1000 mg/kg body weight of the animal being treated/day. For example, in embodiments, the compounds or salts may be administered from about 100 mg/kg to about 300 mg/kg, from about 120 mg/kg to about 280 mg/kg, from about 140 mg/kg to about 260 mg/kg, from about 150 mg/kg to about 250 mg/kg, from about 160 mg/kg to about 240 mg/kg, of subject body weight per day, one or more times a day, to obtain the desired therapeutic effect.

The following examples further illustrate the invention but, of course, should not be construed as in any way limiting its scope.

Example 1

This example illustrates some of the biological properties of compounds in accordance with an embodiment of the invention.

[$^3$H]R—N$^6$-Phenylisopropyladenosine (40, [$^3$H]R-PIA, 63 Ci/mmol), [$^3$H](2-[p-(2-carboxyethyl)phenyl-ethylamino]-5'-N-ethylcarboxamido-adenosine) (41, [$^3$H]CGS21680, 40.5 Ci/mmol) and [$^{125}$I]N$^6$-(4-amino-3-iodobenzyl)adenosine-5'-N-methyluronamide (42, [$^{125}$I]I-AB-MECA, 2200 Ci/mmol) were purchased from Perkin-Elmer Life and Analytical Science (Boston, Mass.). Test compounds were prepared as 5 mM stock solutions in DMSO and stored frozen. Pharmacological standards 1b ($A_3AR$ agonist), adenosine-5'-N-ethylcarboxamide (43, NECA, nonselective AR agonist) and 2-chloro-$N^6$-cyclopentyladenosine (44, CCPA, $A_1AR$ agonist) were purchased from Tocris R&D Systems (Minneapolis, Minn.).

Cell Culture and Membrane Preparation—

CHO cells stably expressing the recombinant $hA_1$ and $hA_3ARs$ and HEK293 cells stably expressing the $hA_{2A}AR$ were cultured in Dulbecco's modified Eagle medium (DMEM) and F12 (1:1) supplemented with 10% fetal bovine serum, 100 units/mL penicillin, 100 μg/mL streptomycin, and 2 μmol/mL glutamine. In addition, 800 μg/mL geneticin was added to the $A_2A$ media, while 500 μg/mL hygromycin was added to the $A_1$ and $A_3$ media. After harvesting, cells were homogenized and suspended in PBS. Cells were then centrifuged at 240 g for 5 min, and the pellet was resuspended in 50 mM Tris-HCl buffer (pH 7.5) containing 10 mM $MgCl_2$. The suspension was homogenized and was then ultra-centrifuged at 14,330 g for 30 min at 4° C. The resultant pellets were resuspended in Tris buffer, incubated with adenosine deaminase (3 units/mL) for 30 min at 37° C. The suspension was homogenized with an electric homogenizer for 10 sec, pipetted into 1 mL vials and then stored at −80° C. until the binding experiments. The protein concentration was measured using the BCA Protein Assay Kit from Pierce Biotechnology, Inc. (Rockford, Ill.).[27]

Binding Assays:

Into each tube in the binding assay was added 50 μL of increasing concentrations of the test ligand in Tris-HCl buffer (50 mM, pH 7.5) containing 10 mM $MgCl_2$, 50 μL of the appropriate agonist radioligand, and finally 100 μL of membrane suspension. For the $A_1AR$ (22 μg of protein/tube) the radioligand used was [$^3H$]40 (final concentration of 3.5 nM). For the $A_{2A}AR$ (20 μg/tube) the radioligand used was [$^3H$]41 (10 nM). For the $A_3AR$ (21 μg/tube) the radioligand used was [$^{125}I$]42 (0.34 nM). Nonspecific binding was determined using a final concentration of 10 μM 43 diluted with the buffer. The mixtures were incubated at 25° C. for 60 min in a shaking water bath. Binding reactions were terminated by filtration through Brandel GF/B filters under a reduced pressure using a M-24 cell harvester (Brandel, Gaithersburg, Md.). Filters were washed three times with 3 mL of 50 mM ice-cold Tris-HCl buffer (pH 7.5). Filters for $A_1$ and $A_{2A}AR$ binding were placed in scintillation vials containing 5 mL of Hydrofluor scintillation buffer and counted using a Perkin Elmer Liquid Scintillation Analyzer (Tri-Carb 2810TR). Filters for $A_3AR$ binding were counted using a Packard Cobra II γ-counter. The $K_i$ values were determined using GraphPad Prism for all assays.

Similar competition binding assays were conducted using HEK293 cell membranes expressing mARs using [$^{125}I$]42 to label $A_1$ or $A_3ARs$ and [$^3H$]41 to label $A_{2A}ARs$. $IC_{50}$ values were converted to $K_i$ values as described.[28] Nonspecific binding was determined in the presence of 100 μM 43.

The results are set forth in Tables 1-5.

Table 1. Structures and binding affinities of AR agonists and two reference compounds (400, 401).

TABLE 1

Structures and binding affinities of AR agonists and two reference compounds (400, 401).

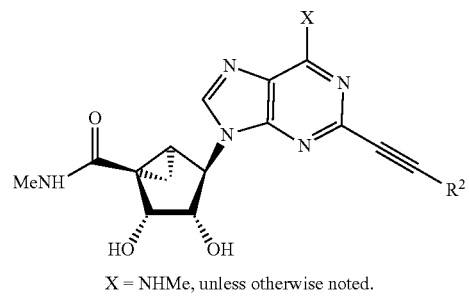

X = NHMe, unless otherwise noted.

| Cmpd# | $R^2$ | $hA_1AR$ % inhibition or $K_i$ (nM) | $hA_{2A}AR^c$ % inhibition or $K_i$ (nM) | $hA_3AR$ % inhibition or $K_i$ (nM) | $mA_3AR$ % inhibition or $K_i$ (nM) |
|---|---|---|---|---|---|
| 400[b] | phenyl | (18% ± 8%) | (14% ± 7%) | 0.85 ± 0.22 | |
| 401[b] | 2-pyridyl | (13% ± 8%) | (13% ± 4%) | 1.01 ± 0.36 | |
| 402 | phenyl, X = H | 28 ± 4% | 1200 | 1.51 ± 0.41 | |
| 11 | 4-OCH$_3$-phenyl | 10 ± 5% | 24 ± 8% | 0.63 ± 0.07 | |

TABLE 1-continued

Structures and binding affinities of AR agonists and two reference compounds (400, 401).

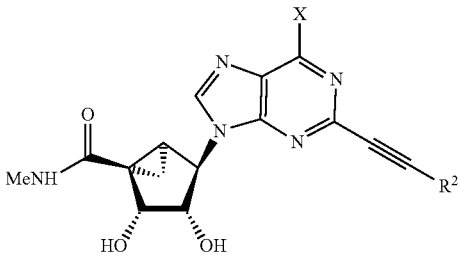

X = NHMe, unless otherwise noted.

| Cmpd# | R² | hA₁AR % inhibition or $K_i$ (nM) | hA₂ₐAR[c] % inhibition or $K_i$ (nM) | hA₃AR % inhibition or $K_i$ (nM) | mA₃AR % inhibition or $K_i$ (nM) |
|---|---|---|---|---|---|
| 12 | 3-OCH₃-phenyl | 8 ± 4% | 26 ± 5% | 0.91 ± 0.07 | |
| 13 | 2-OCH₃-phenyl | 12 ± 7% | 20 ± 7% | 0.77 ± 0.17 | |
| 14 | 3-CF₃-phenyl | 10 ± 9% | 12 ± 6% | 3.39 ± 0.65 | |
| 31 | 4-(CH₂OH)-phenyl | 16 ± 6% | 11 ± 7% | 2.16 ± 0.39 | |
| 300 | 4-pyridyl | 15 ± 3% | 2 ± 2% | 2.07 ± 0.16 | |
| 15 | 3-pyridyl | 16 ± 10% | 12 ± 6% | 2.15 ± 0.38 | |
| 6 | 2-pyrimidinyl | 25 ± 10% | 27 ± 5% | 1.97 ± 0.27 | 65 ± 6 |
| 7 | pyrazinyl | 37 ± 6%, 57% ± 2% (m) | 25 ± 9%, 12% ± 5% (m) | 1.76 ± 0.22 | 68 ± 5 |
| 10 | pyridazinyl | 11 ± 3% | 13 ± 8% | 3.53 ± 0.99 | 112 ± 10 |

TABLE 1-continued

Structures and binding affinities of AR agonists and two reference compounds (400, 401).

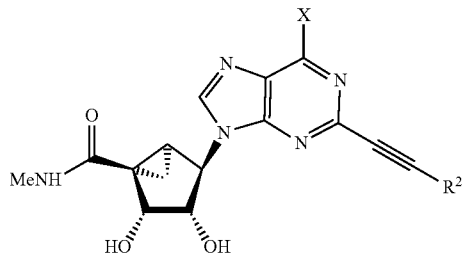

X = NHMe, unless otherwise noted.

| Cmpd# | R² | hA₁AR % inhibition or $K_i$ (nM) | hA$_{2A}$AR$^c$ % inhibition or $K_i$ (nM) | hA₃AR % inhibition or $K_i$ (nM) | mA₃AR % inhibition or $K_i$ (nM) |
|---|---|---|---|---|---|
| 9 | pyrazol-3-yl (NH) | 30 ± 2% | 19 ± 2% | 2.23 ± 0.18 | 50 ± 2 |
| 18 | 1-methylpyrazol-4-yl | 35 ± 7%, 72% ± 6% (m) | 12 ± 6%, 16% ± 2% (m) | 2.34 ± 0.29 | 126 ± 30 |
| 17 | 2-furyl | 30 ± 1%, 59% ± 2% (m) | 18 ± 9%, 17% ± 1% (m) | 0.62 ± 0.06 | 54 ± 11 |
| 29 | 4,5-dimethylfuran-2-yl | 15 ± 6% | 21 ± 3% | 1.45 ± 0.20 | |
| 34 | 5-ethylfuran-2-yl | 18 ± 9% | 4 ± 4% | 1.50 ± 0.28 | |
| 33 | benzofuran-2-yl | 13 ± 3% | 18 ± 3% | 1.62 ± 0.23 | |
| 8 | 2-thienyl | 25 ± 5%, 47% ± 2% (m) | 20 ± 6%, 3% ± 3% (m) | 0.57 ± 0.10 | 43 ± 2 |
| 16 | 3-thienyl | 11 ± 6% | 3 ± 2% | 0.52 ± 0.04 | |
| 32 | 5-chlorothien-2-yl | 6 ± 1%, 38% ± 2% (m) | 24 ± 13%, 7% ± 13% (m) | 0.70 ± 0.11 | 36.1 ± 4.7 |
| 100 | 5-bromothien-2-yl | 18 ± 5% | 19 ± 3%, 10% ± 3% (m) | 0.44 ± 0.12 | |

TABLE 1-continued

Structures and binding affinities of AR agonists and two reference compounds (400, 401).

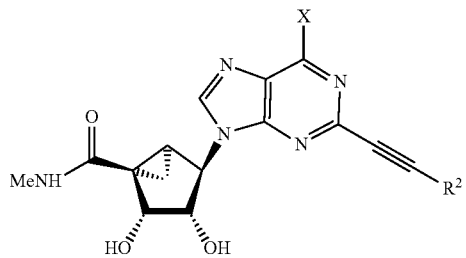

X = NHMe, unless otherwise noted.

| Cmpd# | R² | hA₁AR % inhibition or $K_i$ (nM) | hA$_{2A}$AR[c] % inhibition or $K_i$ (nM) | hA₃AR % inhibition or $K_i$ (nM) | mA₃AR % inhibition or $K_i$ (nM) |
|---|---|---|---|---|---|
| 101 | thiazol-2-yl | 30% | | 1.80 | |
| 37 | ferrocenyl | 25 ± 2%, 45% ± 2% (m) | 47 ± 2%, 4% ± 2% (m) | 2.68 ± 0.44 | 5.46 ± 0.67 |
| 19 | cyclohexyl | 15 ± 5% | 45 ± 6% | 1.68 ± 0.60 | 40.9 ± 1.9 |
| 20 | cyclopropyl | 38 ± 6% | 15 ± 10% | 1.15 ± 0.18 | |
| MRS5698 | 3,4-difluorophenyl, X = 3-chlorobenzyl | 6 ± 4% | 41 ± 10% | 3.49 ± 1.84 | |

[b]Compounds 6 and 7 were reported earlier (as compounds 9 and 10 in Tosh et al., *J. Med. Chem.*, 2012, 55: 4847-4860).

[c]Human, with mouse data denoted by (m)

TABLE 2

Structures and binding affinities of N⁶-phenylcyclopropyl (N)-methanocarba $A_3AR$ agonists

| Compd | R² | X | Stereochem of N⁶ group | $hA_1AR$ % inhibition or $K_i$ (nM) | $hA_{2A}AR$ % inhibition or $K_i$ (nM) | $hA_3AR$ % inhibition or $K_i$ (nM) |
|---|---|---|---|---|---|---|
| 21 | Ph | H | (±)-trans | 2 ± 1% | 43 ± 8% | 6.16 ± 0.22 |
| 22 | Ph | 3-Me | (±)-trans | 8 ± 4% | 53 ± 6% | 17.6 ± 1.3 |
| 23 | Ph | 3-F | (±)-trans | 18 ± 10% | 1% | 16.5 ± 1.9 |
| 24 | Ph | 3-Cl | (±)-trans | 6 ± 3% | 39 ± 5% | 11.2 ± 4.2 |
| 25 | Ph | 3-Br | (±)-trans | 17 ± 4% | 32 ± 18% | 14.5 ± 1.0 |
| 26 | Ph | 3,4-diF | (±)-trans | 11 ± 6% | 0% | 20.2 ± 2.1 |
| 26A | Ph | 3,4-diF | 1R, 2S | | | |
| 27 | 2-pyridyl | 3,4-diF | 1R, 2S | 19 ± 8% | 25 ± 5% | 8.18 ± 2.22 |

TABLE 3

Structures and binding affinities of N⁶-methyl and N⁶-hydroxystyryl compounds

| Cmp | | $hA_1AR$ % inhibition or $K_i$ (nM) | $hA_{2A}AR$ % inhibition or $K_i$ (nM) | $hA_3AR$ % inhibition or $K_i$ (nM) | $mA_3AR$ % inhibition or $K_i$ (nM) |
|---|---|---|---|---|---|
| 40 | | 16 ± 5% | 16 ± 7% | 78.5 ± 19.8 | 136 ± 9 |

TABLE 3-continued

Structures and binding affinities of $N^6$-methyl and $N^6$-hydroxystyryl compounds

| Cmp | | hA$_1$AR % inhibition or K$_i$ (nM) | hA$_{2A}$AR % inhibition or K$_i$ (nM) | hA$_3$AR % inhibition or K$_i$ (nM) | mA$_3$AR % inhibition or K$_i$ (nM) |
|---|---|---|---|---|---|
| 41 | 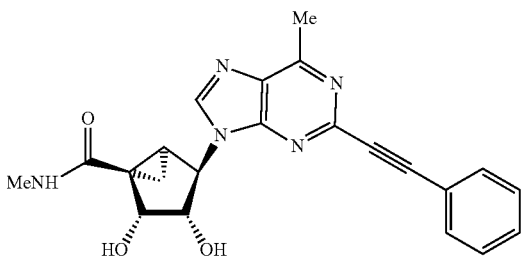 | 15 ± 6% | 34 ± 7% | 6.01 ± 1.60 | 158 ± 10 |

TABLE 4

Structures and binding affinities of $N^2$-triazolyl compounds

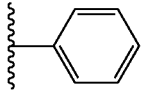 [SMILES: *c1ccccc1]

| Cmpd | R$^1$ | R$^2$ | hA$_1$AR % inhibition or K$_i$ (nM) | hA$_{2A}$AR % inhibition | A$_3$AR$^a$ % inhibition or K$_i$ (nM) |
|---|---|---|---|---|---|
| 100 | CH$_3$ | phenyl | 18 ± 4% | 35 ± 8% | 0.96 ± 0.07 |
| 101 | CH$_3$ | 2-chlorophenyl | 20 ± 5% | 31 ± 6% | 0.95 ± 0.50 |
| 102 | CH$_3$ | 3,4-difluorophenyl | 9 ± 4% | 39 ± 4% | 1.06 ± 0.10 |
| 103 | CH$_3$ | 2-pyridyl | 29 ± 7% | 26 ± 2% | 1.84 ± 0.38 |
| 104 | CH$_3$ | 2-pyrimidyl | 14 ± 7% | 27 ± 3% | 3.48 ± 0.97 |

TABLE 4-continued
Structures and binding affinities of N²-triazolyl compounds
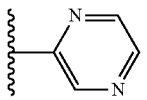
| Cmpd | R¹ | R² | hA$_1$AR % inhibition or K$_i$ (nM) | hA$_{2A}$AR % inhibition | A$_3$AR[a] % inhibition or K$_i$ (nM) |
|---|---|---|---|---|---|
| 105 | CH$_3$ | 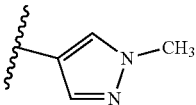 [SMILES: *c1cnn(C)c1] | 25 ± 10% | 8 ± 3% | 2.21 ± 0.34 |
| 106 | CH$_3$ | 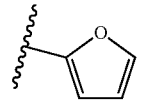 | 2 ± 2% | 1 ± 1% | 2.16 ± 0.32 |
| 107 | CH$_3$ | 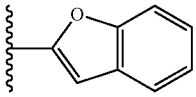 [SMILES: *c1cc2ccccc2o1] | 43 ± 2% | 51 ± 1% | 0.96 ± 0.09 |
| 108 | CH$_3$ | 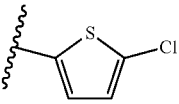 [SMILES: *c1ccc(Cl)s1] | 12 ± 7% | 40 ± 6% | 1.25 ± 0.27 |
| 109 | CH$_3$ | 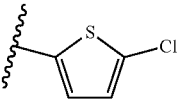 [SMILES: *c1ccc(Cl)s1] | 27 ± 8% | 34 ± 5% | 0.73 ± 0.10 |
| 110 | C$_2$H$_5$ | 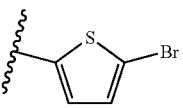 [SMILES: *c1ccc(Br)s1] | 15 ± 11% | 32 ± 5% | 1.22 ± 0.26 |
| 111 | CH$_3$ | 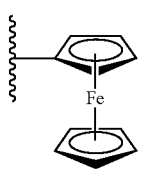 | 33 ± 7% | 7 ± 6% | 0.58 ± 0.17 |
| 112 | CH$_3$ | 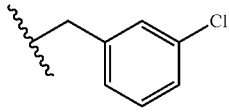 [SMILES: *Cc1cccc(Cl)c1] | 23 ± 3% | 54 ± 2% | 3.09 ± 0.21 |
| 120 | 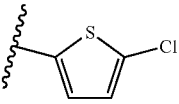 [SMILES: *c1ccc(Cl)s1] | 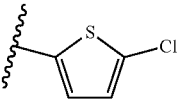 [SMILES: *c1ccc(Cl)s1] | 65% | | 11.7 |

TABLE 4-continued

Structures and binding affinities of N²-triazolyl compounds

| Cmpd | R¹ | R² | hA₁AR % inhibition or $K_i$ (nM) | hA₂ₐAR % inhibition | A₃AR[a] % inhibition or $K_i$ (nM) |
|---|---|---|---|---|---|
| 121 | phenethyl | 5-chlorothien-2-yl | 58% | | 6.66 ± 2.07 |
| 125 | cyclobutylmethyl | 5-chlorothien-2-yl | 77% | | 7.13 |

[a] Binding in membranes prepared from CHO or HEK293 (A₂ₐ only) cells stably expressing one of three hAR subtypes. The binding affinity for hA₁, A₂ₐ and A₃ARs was expressed as $K_i$ values (n = 3-4), measured using agonist radioligands [³H]N⁶—R-phenylisopropyladenosine 65, [³H]2-[p-(2-carboxyethyl)phenyl-ethylamino]-5'-N-ethylcarboxamido-adenosine 66, or [¹²⁵I]N⁶-(4-amino-3-iodobenzyl)adenosine-5'-N-methyl-uronamide 67, respectively. A percent in italics refers to inhibition of binding at 10 μM. Nonspecific binding was determined using 68 (10 μM at hARs, 100 μM at mARs).

TABLE 5

Structures and binding affinities of N²-azido and N²-iodo compounds

| Cmpd | R¹ | R² | hA₁AR % inhibition or $K_i$ (nM) | hA₂ₐAR % inhibition | A₃AR[a] % inhibition or $K_i$ (nM) |
|---|---|---|---|---|---|
| 113 | CH₃ | N₃ | 77 ± 1% | 1 ± 1% | 0.54 ± 0.10 |
| 114 | CH₃ | I | | | 1.91 ± 0.85 |
| 115 | cyclobutylmethyl | N₃ | 100% | 46% | 0.85 ± 0.10 |
| 116 | 3-chlorophenethyl | I | 2000 | >10,000 | 3.6 |

TABLE 5-continued

Structures and binding affinities of N²-azido and N²-iodo compounds

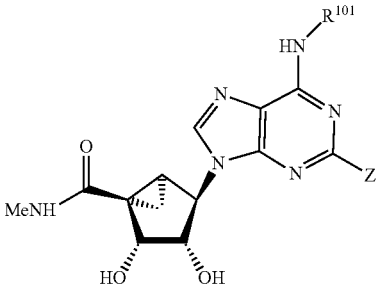

| Cmpd | R¹ | R² | hA$_1$AR % inhibition or K$_i$ (nM) | hA$_{2A}$AR % inhibition | A$_3$AR$^a$ % inhibition or K$_i$ (nM) |
|---|---|---|---|---|---|
| 117 | (phenylpropyl) | N$_3$ | 93% | 71%, 1110 | 0.85 ± 0.10 |
| 118 | (cyclobutyl) | I | 93% | >10,000 | 1.53 ± 0.45 |
| 119 | (phenylpropyl) | I | 68% | 42% | 0.91 ± 0.14 |
| 122 | CH$_3$CH$_2$ | I | 1910 ± 300 | 11 ± 7% | 1.22 ± 0.21 |
| 123 | CH$_3$CH$_2$ | N$_3$ | 707 ± 152 | 11 ± 6% | 0.60 ± 0.08 |
| 124 | (3-chlorobenzyl) | N$_3$ | | 2770 | 1.08 ± 0.75 |

Example 2

This example demonstrates a method of preparing compounds in accordance with an embodiment of the invention.

(1S,2R,3S,4R,5S)-2,3-Dihydroxy-N-methyl-4-(6-(methylamino)-2-(pyrimidin-2-ylethynyl)-9H-purin-9-yl)bicyclo[3.1.0]hexane-1-carboxamide (6)

PdCl$_2$(PPh$_3$)$_2$ (6.08 mg, 0.02 mmol), CuI (1.0 mg, 0.005 mmol), 2-ethynylpyrimidine (27.1 mg, 0.26 mmol) and triethylamine (0.06 mL, 0.43 mmol) were added to a solution of compound 53 (21 mg, 0.04 mmol) in anhydrous DMF (1 mL), and the mixture stirred at room temperature overnight. Solvent was evaporated under vacuum, and the residue was roughly purified on flash silica gel column chromatography. The resulting compound was dissolved in MeOH (2 mL) and 10% trifluoroacetic acid (2 mL) and heated at 70° C. for 5 h. Solvent was evaporated under vacuum, and the residue was purified on flash silica gel column chromatography (CH$_2$Cl$_2$:MeOH=25:1) to give the compound 6 (12.2 mg, 67%) as syrup. $^1$H NMR (CD$_3$OD, 400 MHz) δ 8.86 (d, J=5.2 Hz, 2H), 8.14 (s, 1H), 7.53 (t, J=5.2 Hz, 1H), 5.17 (d, J=6.8 Hz, 1H), 4.92 (s, 1H), 4.6 (d, J=6.4 Hz, 1H), 3.14 (br s, 3H), 2.86 (s, 3H), 2.11-2.07 (m, 1H), 1.84 (t, J=5.2 Hz, 1H), 1.42-1.39 (m, 1H). HRMS calculated for C$_{20}$H$_{21}$N$_8$O$_3$ (M+H)$^+$: 421.1737; found 421.1732.

(1S,2R,3S,4R,5S)-2,3-Dihydroxy-N-methyl-4-(6-(methylamino)-2-(pyrazin-2-ylethynyl)-9H-purin-9-yl)bicyclo[3.1.0]hexane-1-carboxamide (7)

Compound 7 (65%) was prepared from compound 53 following the same method for compound 6. $^1$H NMR (CD$_3$OD, 400 MHz) δ 8.92 (s, 1H), 8.69 (d, J=2.4 Hz, 1H), 8.64 (d, J=2.4 Hz, 1H), 8.14 (s, 1H), 5.12 (d, J=5.2 Hz, 1H), 4.89 (s, 1H), 4.05 (d, J=6.4 Hz, 1H), 3.15 (br s, 3H), 2.85 (s, 3H), 2.12-2.08 (m, 1H), 1.86 (t, J=5.2 Hz, 1H), 1.42-1.40 (m, 1H). HRMS calculated for C$_{20}$H$_{21}$N$_8$O$_3$ (M+H)$^+$: 421.1737; found 421.1725.

(1S,2R,3S,4R,5S)-2,3-Dihydroxy-N-methyl-4-(6-(methylamino)-2-(thiophen-2-ylethynyl)-9H-purin-9-yl)bicyclo[3.1.0]hexane-1-carboxamide (8)

Compound 8 (61%) was prepared from compound 53 following the same method for compound 6. $^1$H NMR (CD$_3$OD, 400 MHz) δ 8.10 (s, 1H), 7.57 (dd, J$_1$=1.2, J$_2$=4.0 Hz, 1H), 7.50 (dd, J$_1$=1.2, J$_2$=4.0 Hz, 1H), 7.13 (dd, J$_1$=1.6, J$_2$=3.6 Hz, 1H), 5.05 (d, J=6.4 Hz, 1H), 4.88 (s, 1H), 4.02 (d, J=6.4 Hz, 1H), 3.14 (br s, 3H), 2.86 (s, 3H), 2.13-2.09 (m, 1H), 1.88 (t, J=5.2 Hz, 1H), 1.41-1.39 (m, 1H). HRMS calculated for $C_{20}H_{21}N_6O_3S$ (M+H)$^+$: 425.1396; found 425.1388.

(1S,2R,3S,4R,5S)-4-(2-((1H-Pyrazol-3-yl)ethynyl)-6-(methylamino)-9H-purin-9-yl)-2,3-dihydroxy-N-methylbicyclo[3.1.0]hexane-1-carboxamide (9)

Compound 9 (64%) was prepared from compound 53 following the same method for compound 6. $^1$H NMR (CD$_3$OD, 400 MHz) δ 8.10 (s, 1H), 7.73 (s, 1H), 6.66 (s, 1H), 5.12 (d, J=6.8 Hz, 1H), 4.87 (s, 1H), 4.04 (d, J=6.8 Hz, 1H), 3.13 (br s, 3H), 2.85 (s, 3H), 2.10-2.07 (m, 1H), 1.85 (t, J=4.8 Hz, 1H), 1.41-1.38 (m, 1H). HRMS calculated for $C_{19}H_{21}N_8O_3$ (M+H)$^+$: 409.1737; found 409.1731.

(1S,2R,3S,4R,5S)-2,3-Dihydroxy-N-methyl-4-(6-(methylamino)-2-(pyridazin-3-ylethynyl)-9H-purin-9-yl)bicyclo[3.1.0]hexane-1-carboxamide (10)

Compound 10 (65%) was prepared from compound 53 following the same method for compound 6. $^1$H NMR (CD$_3$OD, 400 MHz) δ 9.23 (d, J=3.2 Hz, 1H), 8.15 (s, 1H), 8.03 (d, J=6.8 Hz, 1H), 7.83-7.81 (m, 1H), 5.14 (d, J=5.2 Hz, 1H), 4.90 (s, 1H), 4.07 (d, J=5.2 Hz, 1H), 3.15 (br s, 3H), 2.84 (s, 3H), 2.11-2.08 (m, 1H), 1.86 (t, J=4.8 Hz, 1H), 1.42-1.39 (m, 1H). HRMS calculated for $C_{20}H_{21}N_8O_3$ (M+H)$^+$: 421.1737; found 421.1734.

(1S,2R,3S,4R,5S)-2,3-Dihydroxy-4-(2-((4-methoxyphenyl)ethynyl)-6-(methylamino)-9H-purin-9-yl)-N-methylbicyclo[3.1.0]hexane-1-carboxamide (11)

Compound 11 (68%) was prepared from compound 53 following the same method for compound 6. $^1$H NMR (CD$_3$OD, 400 MHz) δ 8.08 (s, 1H), 7.60 (d, J=9.2 Hz, 1H), 7.01 (d, J=9.2 Hz, 1H), 5.05 (d, J=5.2 Hz, 1H), 4.91 (s, 1H), 4.02 (d, J=6.0 Hz, 1H), 3.86 (s, 3H), 3.15 (br s, 3H), 2.85 (s, 3H), 2.13-2.09 (m, 1H), 1.88 (t, J=5.2 Hz, 1H), 1.41-1.39 (m, 1H). HRMS calculated for $C_{23}H_{25}N_6O_4$ (M+H)$^+$: 449.1937; found 449.1944.

(1S,2R,3S,4R,5S)-2,3-Dihydroxy-4-(2-((3-methoxyphenyl)ethynyl)-6-(methylamino)-9H-purin-9-yl)-N-methylbicyclo[3.1.0]hexane-1-carboxamide (12)

Compound 12 (69%) was prepared from compound 53 following the same method for compound 6. $^1$H NMR (CD$_3$OD, 400 MHz) δ 8.10 (s, 1H), 7.35 (t, J=6.0 Hz, 1H), 7.24-7.21 (m, 2H), 7.02 (d, J=8.4 Hz, 1H), 5.06 (d, J=6.8 Hz, 1H), 4.92 (s, 1H), 4.02 (d, J=6.4 Hz, 1H), 3.85 (s, 3H), 3.15 (br s, 3H), 2.84 (s, 3H), 2.13-2.09 (m, 1H), 1.88 (t, J=4.4 Hz, 1H), 1.41-1.38 (m, 1H). HRMS calculated for $C_{23}H_{25}N_6O_4$ (M+H)$^+$: 449.1937; found 449.1944.

(1S,2R,3S,4R,5S)-2,3-Dihydroxy-4-(2-((2-methoxyphenyl)ethynyl)-6-(methylamino)-9H-purin-9-yl)-N-methylbicyclo[3.1.0]hexane-1-carboxamide (13)

Compound 13 (69%) was prepared from compound 53 following the same method for compound 6. $^1$H NMR (CD$_3$OD, 600 MHz) δ 8.10 (s, 1H), 7.59 (d, J=6.0 Hz, 1H), 7.45 (t, J=7.2 Hz, 1H), 7.10 (d, J=8.4 Hz, 1H), 7.01 (t, J=7.2 Hz, 1H), 5.15 (d, J=6.0 Hz, 1H), 4.90 (s, 1H), 4.04 (d, J=6.0 Hz, 1H), 3.96 (s, 3H), 3.15 (br s, 3H), 2.82 (s, 3H), 2.09-2.07 (m, 1H), 1.86 (t, J=4.8 Hz, 1H), 1.43-1.41 (m, 1H). HRMS calculated for $C_{23}H_{25}N_6O_4$ (M+H)$^+$: 449.1937; found 449.1932.

(1 S,2S,3R,4R,5S)-2,3-Dihydroxy-N-methyl-4-(6-(methylamino)-2-((3-(trifluoromethyl)phenyl)ethynyl)-9H-purin-9-yl)bicyclo[3.1.0]hexane-1-carboxamide (14)

Compound 14 (70%) was prepared from compound 53 following the same method for compound 6. $^1$H NMR (CD$_3$OD, 400 MHz) δ 8.14 (s, 1H), 7.97 (s, 1H), 7.92 (d, J=7.6 Hz, 1H), 7.78 (d, J=7.6 Hz, 1H), 7.68 (t, J=8.0 Hz, 1H), 5.08 (d, J=4.8 Hz, 1H), 4.90 (s, 1H), 4.04 (d, J=5.2 Hz, 1H), 3.15 (br s, 3H), 2.84 (s, 3H), 2.13-2.10 (m, 1H), 1.88 (t, J=5.2 Hz, 1H), 1.42-1.39 (m, 1H).

HRMS calculated for $C_{23}H_{22}N_6O_3F_3$ (M+H)$^+$: 487.1705; found 487.1716.

(1S,2R,3S,4R,5S)-2,3-Dihydroxy-N-methyl-4-(6-(methylamino)-2-(pyridin-3-ylethynyl)-9H-purin-9-yl)bicyclo[3.1.0]hexane-1-carboxamide (15)

Compound 15 (60%) was prepared from compound 53 following the same method for compound 6. $^1$H NMR (CD$_3$OD, 400 MHz) δ 8.87 (s, 1H), 8.64 (s, 1H), 8.18 (d, J=6.4 Hz, 1H), 8.15 (s, 1H), 7.61-7.58 (m, 1H), 5.05 (d, J=5.2 Hz, 1H), 4.90 (s, 1H), 4.02 (d, J=5.2 Hz, 1H), 3.13 (br s, 3H), 2.82 (s, 3H), 2.11-2.09 (m, 1H), 1.87 (t, J=4.0 Hz, 1H), 1.40-1.37 (m, 1H). HRMS calculated for $C_{21}H_{22}N_7O_3$ (M+H)$^+$: 420.1784; found 420.1785.

(1 S,2R,3S,4R,5S)-2,3-Dihydroxy-N-methyl-4-(6-(methylamino)-2-(thiophen-3-ylethynyl)-9H-purin-9-yl)bicyclo[3.1.0]hexane-1-carboxamide (16)

Compound 16 (59%) was prepared from compound 53 following the same method for compound 6. $^1$H NMR (CD$_3$OD, 400 MHz) δ 8.13 (s, 1H), 7.88 (dd, J=1.2, J$_2$=2.0 Hz, 1H), 7.54 (dd, J$_1$=2.0, J$_2$=3.2 Hz, 1H), 7.33 (dd, J$_1$=1.2, J$_2$=4.0 Hz, 1H), 5.07 (d, J=5.2 Hz, 1H), 4.89 (s, 1H), 4.04 (d, J=5.2 Hz, 1H), 3.15 (br s, 3H), 2.85 (s, 3H), 2.13-2.09 (m, 1H), 1.87 (t, J=4.8 Hz, 1H), 1.42-1.39 (m, 1H). HRMS calculated for $C_{20}H_{21}N_6O_3S$ (M+H)$^+$: 425.1396; found 425.1403.

(1S,2R,3S,4R,5S)-4-(2-(Furan-2-ylethynyl)-6-(methylamino)-9H-purin-9-yl)-2,3-dihydroxy-N-methylbicyclo[3.1.0]hexane-1-carboxamide (17)

Compound 17 (58%) was prepared from compound 53 following the same method for compound 6. $^1$H NMR (CD$_3$OD, 400 MHz) δ 8.16 (s, 1H), 7.66 (d, J=1.2 Hz, 1H), 6.95 (d, J=2.8 Hz, 1H), 6.58 (dd, J$_1$=1.6, J$_2$=2.0 Hz, 1H), 5.07 (d, J=5.2 Hz, 1H), 4.89 (s, 1H), 4.03 (d, J=6.4 Hz, 1H), 3.14 (br s, 3H) 2.87 (s, 3H), 2.11-2.09 (m, 1H), 1.86 (t, J=4.8 Hz, 1H), 1.41-1.40 (m, 1H). HRMS calculated for $C_{20}H_{21}N_6O_4$ (M+H)$^+$: 409.1624; found 409.1611.

(1S,2R,3S,4R,5S)-2,3-Dihydroxy-N-methyl-4-(2-((1-methyl-1H-pyrazol-4-yl)ethynyl)-6-(methylamino)-9H-purin-9-yl)bicyclo[3.1.0]hexane-1-carboxamide (18)

Compound 18 (63%) was prepared from compound 53 following the same method for compound 6. $^1$H NMR (CD$_3$OD, 400 MHz) δ 8.08 (s, 1H), 7.98 (s, 1H), 7.75 (s, 1H), 5.05 (d, J=5.6 Hz, 1H), 4.88 (s, 1H), 4.02 (d, J=6.4 Hz, 1H), 3.94 (s, 3H), 3.13 (br s, 3H), 2.86 (d, J=4.4 Hz, 1H), 2.12-2.08 (m, 1H), 1.87 (t, J=4.8 Hz, 1H), 1.41-1.37 (m, 1H). HRMS calculated for $C_{20}H_{23}N_8O_3$ (M+H)$^+$: 423.1888; found 423.1888.

(1S,2R,3S,4R,5S)-4-(2-(Cyclohexylethynyl)-6-(methylamino)-9H-purin-9-yl)-2,3-dihydroxy-N-methylbicyclo[3.1.0]hexane-1-carboxamide (19)

Compound 7 (71%) was prepared from compound 53 following the same method for compound 6. $^1$H NMR (CD$_3$OD, 400 MHz) δ 8.06 (s, 1H), 4.98 (d, J=6.8 Hz, 1H), 4.85 (s, 1H), 3.95 (d, J=6.4 Hz, 1H), 3.11 (br s, 3H) 2.86 (s, 3H), 2.86-2.62 (m, 1H), 2.11-2.08 (m, 1H), 1.99-1.96 (m, 2H), 1.89 (t, J=4.8 Hz, 1H), 1.84-1.80 (m, 2H), 1.63-1.58 (m, 3H), 1.43-1.39 (m, 4H). HRMS calculated for $C_{22}H_{29}N_6O_3$ (M+H)$^+$: 425.2301; found 425.2308.

(1S,2R,3S,4R,5S)-4-(2-(Cyclopropylethynyl)-6-(methylamino)-9H-purin-9-yl)-2,3-dihydroxy-N-methylbicyclo[3.1.0]hexane-1-carboxamide (20)

Compound 7 (68%) was prepared from compound 53 following the same method for compound 6. $^1$H NMR (CD$_3$OD, 400 MHz) δ 8.06 (s, 1H), 5.02 (d, J=6.0 Hz, 1H), 4.83 (s, 1H), 3.97 (d, J=6.4 Hz, 1H), 3.10 (br s, 3H), 2.88 (s, 3H), 2.10-2.07 (m, 1H), 1.86 (t, J=4.8 Hz, 1H), 1.59-1.52 (m, 1H), 1.40-1.37 (m, 1H), 1.00-0.98 (m, 2H), 0.94-0.86 (m, 2H). HRMS calculated for $C_{19}H_{23}N_6O_3$ $(M+H)^+$: 383.1832; found 383.1838.

(1S,2R,3S,4R,5S)-4-(2-((4,5-Dimethylfuran-2-yl)ethynyl)-6-(methylamino)-9H-purin-9-yl)-2,3-dihydroxy-N-methylbicyclo[3.1.0]hexane-1-carboxamide (29)

Compound 29 (63%) was prepared from compound 53 following the same method for compound 37. $^1$H NMR (CD$_3$OD, 400 MHz) δ 8.09 (s, 1H), 6.69 (s, 1H), 5.06 (d, J=6.4 Hz, 1H), 4.85 (s, 1H), 4.01 (d, J=6.4 Hz, 1H), 3.12 (br s, 3H), 2.87 (s, 3H), 2.26 (s, 3H), 2.12-2.08 (m, 1H), 1.99 (s, 3H), 1.85 (t, J=4.8 Hz, 1H), 1.40-1.38 (m, 1H). HRMS calculated for $C_{22}H_{25}N_6O_4$ $(M+H)^+$: 437.1932; found 437.1934.

(1S,2R,3S,4R,5S)-2,3-Dihydroxy-N-methyl-4-(6-(methylamino)-2-(pyridin-4-ylethynyl)-9H-purin-9-yl)bicyclo[3.1.0] hexane-1-carboxamide (30)

Compound 30 (63%) was prepared from compound 53 following the same method for compound 6. $^1$H NMR (CD$_3$OD, 400 MHz) δ 8.63 (d, J=6.0 Hz, 2H), 8.14 (s, 1H), 7.65 (d, J=6.0 Hz, 1H), 5.06 (d, J=6.0 Hz, 1H), 4.90 (s, 1H), 4.03 (d, J=6.8 Hz, 1H), 3.14 (br s, 3H), 2.13-2.10 (m, 1H), 1.88 (d, J=4.8 Hz, 1H), 1.42-1.40 (m, 1H). HRMS calculated for $C_{21}H_{22}N_7O_3$ $(M+H)^+$: 420.1784; found 420.1786.

(1S,2R,3S,4R,5S)-2,3-Dihydroxy-4-(2-((4-(hydroxymethyl)phenyl)ethynyl)-6-(methylamino)-9H-purin-9-yl)-N-methylbicyclo[3.1.0]hexane-1-carboxamide (31)

Compound 31 (66%) was prepared from compound 53 following the same method for compound 6. $^1$H NMR (CD$_3$OD, 400 MHz) δ 8.13 (s, 1H), 7.63 (d, J=8.0 Hz, 2H), 7.43 (d, J=8.0 Hz, 2H), 5.06 (d, J=6.4 Hz, 1H), 4.89 (s, 1H), 4.67 (s, 2H), 4.02 (d, J=6.4 Hz, 1H), 3.15 (br s, 3H), 2.84 (s, 3H), 2.13-2.09 (m, 1H), 1.88 (d, J=4.8 Hz, 1H), 1.41-1.39 (m, 1H). HRMS calculated for $C_{23}H_{25}N_6O_4$ $(M+H)^+$: 449.1937; found 449.1942.

(1S,2R,3S,4R,5S)-4-(2-((5-Chlorothiophen-2-yl)ethynyl)-6-(methylamino)-9H-purin-9-yl)-2,3-dihydroxy-N-methylbicyclo[3.1.0]hexane-1-carboxamide (32)

Compound 32 (59%) was prepared from compound 53 following the same method for compound 6. $^1$H NMR (CD$_3$OD, 400 MHz) δ 8.11 (s, 1H), 7.31 (d, J=4.0 Hz, 1H), 7.03 (d, J=4.0 Hz, 1H), 5.04 (d, J=7.2 Hz, 1H), 4.86 (s, 1H), 4.01 (d, J=6.8 Hz, 1H), 3.13 (br s, 3H), 2.86 (s, 3H), 2.12-2.09 (m, 1H), 1.88 (d, J=4.8 Hz, 1H), 1.41-1.38 (m, 1H). HRMS calculated for $C_{20}H_{20}N_6O_3SCl$ $(M+H)^+$: 459.1006; found 459.1005.

(1S,2R,3S,4R,5S)-4-(2-(Benzofuran-2-ylethynyl)-6-(methylamino)-9H-purin-9-yl)-2,3-dihydroxy-N-methylbicyclo[3.1.0]hexane-1-carboxamide (33)

Compound 33 (62%) was prepared from compound 53 following the same method for compound 6. $^1$H NMR (CD$_3$OD, 400 MHz) δ 8.12 (s, 1H), 7.67 (d, J=7.6 Hz, 1H), 7.5 (d, J=7.6 Hz, 1H), 7.43 (t, J=6.0 Hz, 1H), 7.33-7.31 (m, 2H), 5.11 (d, J=5.2 Hz, 1H), 4.89 (s, 1H), 4.04 (d, J=6.4 Hz, 1H), 3.15 (br s, 3H), 2.89 (s, 3H), 2.13-2.10 (m, 1H), 1.87 (t, J=4.8 Hz, 1H), 1.42-1.39 (m, 1H). HRMS calculated for $C_{24}H_{23}N_6O_4$ $(M+H)^+$: 459.1775; found 459.1777.

(1S,2R,3S,4R,5S)-4-(2-((5-Ethylfuran-2-yl)ethynyl)-6-(methylamino)-9H-purin-9-yl)-2,3-dihydroxy-N-methylbicyclo[3.1.0]hexane-1-carboxamide (34)

Compound 34 (53%) was prepared from compound 53 following the same method for compound 6. $^1$H NMR (CD$_3$OD, 400 MHz) δ 8.11 (s, 1H), 6.82 (d, J=7.2 Hz, 1H), 6.18 (d, J=7.6 Hz, 1H), 5.08 (d, J=6.4 Hz, 1H), 4.93 (s, 1H), 4.02 (d, J=6.4 Hz, 1H), 3.14 (br s, 3H), 2.75-2.69 (m, 2H), 2.11-2.08 (m, 1H), 1.86 (t, J=5.2 Hz, 1H), 1.41-1.38 (m, 1H), 1.29 (t, J=7.6 Hz, 3H). HRMS calculated for $C_{22}H_{25}N_6O_4$ $(M+H)^+$: 437.1932; found 437.1932.

(1S,2R,3S,4R,5S)-4-(2-((5-Bromothiophen-2-yl)ethynyl0-6-(methylamino)-9H-purin-9-yl)-2,3-dihydroxy-N-methylbicyclo[3.1.0]hexane-1-carboxamide (100)

Compound 100 (48%) was prepared from compound 53 following the same method for compound 6. $^1$H NMR (CD$_3$OD, 400 MHz) δ 8.10 (s, 1H), 7.28 (d, J=4.0 Hz, 1H), 7.15 (d, J=4.0 Hz, 1H), 5.05 (d, J=5.2 Hz, 1H), 4.91 (s, 1H), 4.02 (d, J=5.6 Hz, 1H), 3.14 (br s, 3H), 2.86 (s, 3H), 2.12-2.09 (m, 1H), 1.88 (t, J=4.8 Hz, 1H), 1.41-1.37 (m, 1H). HRMS calculated for $C_{20}H_{20}N_6O_3SBr$ $(M+H)^+$; 503.0495; found 503.0498.

(1 S,2S,3R,4R,5S)-2,3-dihydroxy-N-methyl-4-(6-(methylamino)-2-(thiazol-2-ylethynyl)-9H-purin-9-yl)bicyclo[3.1.0]hexane-1-carboxamide (101)

Compound 101 (64%) was prepared from compound 53 following the same method for compound 6. $^1$H NMR (CD$_3$OD, 400 MHz) δ 8.18 (s, 1H), 7.97 (d, J=3.2 Hz, 1H), 7.82 (d, J=3.2 Hz, 1H), 5.12 (d, J=5.2 Hz, 1H), 4.90 (s, 1H), 4.04 (d, J=6.4 Hz, 1H), 3.14 (br s, 3H), 2.86 (s, 3H), 2.11-2.07 (m, 1H), 1.86 (t, J=4.8 Hz, 1H), 1.42-1.38 (m, 1H). HRMS calculated for $C_{19}H_{20}N_7O_3S$ $(M+H)^+$; 426.1343; found 426.1342.

(1S,2R,3S,4R,5S)-4-(2-((1H-Pyrrol-2-yl)ethynyl)-6-(methylamino)-9H-purin-9-yl)-2,3-dihydroxy-N-methylbicyclo[3.1.0]hexane-1-carboxamide (35)

(1S,2R,3S,4R,5S)-2,3-Dihydroxy-4-(2-((5-hydroxypyridin-3-yl)ethynyl)-6-(methylamino)-9H-purin-9-yl)-N-methylbicyclo[3.1.0]hexane-1-carboxamide (36)

(1S,2R,3S,4R,5S)-4-(2-((Ferrocen-yl)ethynyl)-6-(methylamino)-9H-purin-9-yl)-2,3-dihydroxy-N-methylbicyclo[3.1.0]hexane-1-carboxamide (37)

A solution of compound 53 (31 mg, 0.06 mmol) in methanol (3 mL) and 10% trifluoromethane sulfonic acid (2 mL) was heated at 70° C. for 5 h. Solvent was evaporated under vacuum, and the residue was purified on flash silica gel column chromatography (CH$_2$Cl$_2$:MeOH=25:1) to give the isopropylidene-deblocked derivative (27 mg, 95%) as syrup. PdCl$_2$(PPh$_3$)$_2$ (8.5 mg, 0.012 mmol), CuI (1.1 mg, 0.006 mmol), ethynylferrocene (76.6 mg, 0.36 mmol) and triethylamine (0.08 mL, 0.6 mmol) were added to a solution of the obtained compound (27 mg, 0.06 mmol) in anhydrous DMF (1.2 mL), and the mixture stirred at room temperature overnight. Solvent was evaporated under vacuum, and the residue was purified on flash silica gel column chromatography (CH$_2$Cl$_2$:MeOH=30:1) to give the compound 37 (29 mg, 86%) as light yellow syrup. $^1$H NMR (CD$_3$OD, 400 MHz) δ 8.10 (s, 1H), 5.01 (d, J=6.4 Hz, 1H), 4.89 (s, 1H), 4.63 (s, 2H), 4.40 (s, 2H), 4.31 (s, 6H), 4.01 (d, J=6.4 Hz, 1H), 3.15 (br s, 3H), 2.88 (s, 3H), 2.13-2.10 (m, 1H), 1.91 (t, J=4.8 Hz, 1H), 1.42-1.38 (m, 1H). HRMS calculated for $C_{26}H_{27}N_6O_3Fe$ $(M+H)^+$: 527.1489; found 527.1489.

Ethyl (3aS,3bS,4aS,5R,5aR)-5-(2-iodo-6-((2-phenylcyclopropyl)amino)-9H-purin-9-yl)-2,2-dimethyltetrahydrocyclopropa[3,4]cyclopenta[1,2-d][1,3]dioxole-3b(3aH)-carboxylate (55a)

2-phenylcyclopropan-1-amine (152 mg, 0.90 mmol) and triethylamine (0.35 mL, 1.8 mmol) were added to a solution of compound 52 (91 mg, 0.18 mmol) in anhydrous methanol (3 mL) and the mixture stirred at room temperature overnight. Solvent was evaporated under vacuum, and the residue was purified on flash silica gel column chromatography (hexane:ethylacetate=1:1) to give the compound 55a (82 mg, 76%) as syrup.
$^1$H NMR (CD$_3$OD, 400 MHz) δ 7.96 (s, 1H), 7.36-7.28 (m, 3H), 7.19 (t, J=7.2 Hz, 2H), 5.84 (d, J=6.4 Hz, 1H), 4.9

(s, 1H), 4.81 (d, J=6.4 Hz, 1H), 4.31-4.27 (m, 2H), 2.72-2.67 (m, 1H), 2.26-2.22 (m, 1H), 2.17-2.13 (m, 1H), 1.65-1.61 (m, 1H), 1.53-1.48 (m, 4H), 1.36-1.33 (m, 3H), 1.27 (s, 3H), 0.85-0.84 (m, 1H). HRMS calculated for $C_{26}H_{29}N_5O_4I$ (M+H)$^+$: 602.1264; found 602.1282.

Ethyl (3aS,3bS,4aS,5R,5aR)-5-(2-iodo-6-((2-(m-tolyl)cyclopropyl)amino)-9H-purin-9-yl)-2,2-dimethyltetrahydrocyclopropa[3,4]cyclopenta[1,2-d][1,3]dioxole-3b(3aH)-carboxylate (55b)

Compound 55b (73%) was prepared from compound 52 following the same method for compound 55a. $^1$H NMR (CD$_3$OD, 400 MHz) δ 7.96 (s, 1H), 7.24 (s, 1H), 7.19-7.12 (m, 2H), 7.02 (d, J=7.2 Hz, 1H), 5.84 (d, J=7.2 Hz, 1H), 4.95 (s, 1H), 4.82 (d, J=6.8 Hz, 1H), 4.31-4.27 (m, 2H), 2.36 (s, 3H), 2.26-2.22 (m, 1H), 2.16-2.05 (m, 1H), 1.65-1.62 (m, 1H), 1.53-1.50 (m, 4H), 1.36-1.33 (m, 4H), 1.29-1.23 (m, 4H). HRMS calculated for $C_{27}H_{31}N_5O_4I$ (M+H)$^+$: 616.1415; found 616.1413.

Ethyl (3aS,3bS,4aS,5R,5aR)-5-(6-((2-(3-fluorophenyl)cyclopropyl)amino)-2-iodo-9H-purin-9-yl)-2,2-dimethyltetrahydrocyclopropa[3,4]cyclopenta[1,2-d][1,3]dioxole-3b(3aH)-carboxylate (55c)

Compound 55c (70%) was prepared from compound 52 following the same method for compound 55a. $^1$H NMR (CD$_3$OD, 400 MHz) δ 7.97 (s, 1H), 7.33-7.28 (m, 1H), 7.19-7.18 (m, 2H), 6.95-6.90 (m, 1H), 5.84 (d, J=6.8 Hz, 1H), 4.95 (s, 1H), 4.83-4.82 (m, 1H), 4.29-4.26 (m, 2H), 3.01 (br s, 1H), 2.26-2.22 (m, 1H), 2.18-2.12 (m, 1H), 1.65-1.62 (m, 1H), 1.53-1.49 (m, 4H), 1.42-1.32 (m, 4H), 1.31-1.23 (m, 4H). HRMS calculated for $C_{26}H_{28}N_5O_4IF$ (M+H)$^+$: 620.1170; found 620.1184.

Ethyl (3aS,3bS,4aS,5R,5aR)-5-(6-((2-(3-chlorophenyl)cyclopropyl)amino)-2-iodo-9H-purin-9-yl)-2,2-dimethyltetrahydrocyclopropa[3,4]cyclopenta[1,2-d] [1,3] dioxole-3b (3aH)-carboxylate (55d)

Compound 55d (79%) was prepared from compound 52 following the same method for compound 55a. $^1$H NMR (CD$_3$OD, 400 MHz) δ 7.96 (s, 1H), 7.43 (s, 1H), 7.30-7.19 (m, 3H), 5.84 (d, J=6.4 Hz, 1H), 4.95 (s, 1H), 4.83-4.80 (m, 1H), 4.34-4.33 (m, 2H), 2.98 (br s, 1H), 2.26-2.21 (m, 1H), 2.15-2.11 (m, 1H), 1.65-1.61 (m, 1H), 1.53-1.48 (m, 4H), 1.41-1.35 (m, 5H), 1.29 (s, 3H). HRMS calculated for $C_{26}H_{28}N_5O_4ICl$ (M+H)$^+$: 636.087; found 636.087.

Ethyl (3aS,3bS,4aS,5R,5aR)-5-(6-((2-(3-bromophenyl)cyclopropyl)amino)-2-iodo-9H-purin-9-yl)-2,2-dimethyltetrahydrocyclopropa[3,4]cyclopenta[1,2-d] [1,3]dioxole-3b (3aH)-carboxylate (55e)

Compound 55e (82%) was prepared from compound 52 following the same method for compound 55a. $^1$H NMR (CD$_3$OD, 400 MHz) δ 7.97 (s, 1H), 7.62 (s, 1H), 7.36 (d, J=7.6 Hz, 2H), 7.22 (d, J=7.6 Hz, 1H), 5.84 (d, J=7.2 Hz, 1H), 4.95 (s, 1H), 4.83-4.82 (m, 1H), 4.34-4.25 (m, 2H), 3.03 (br s, 1H), 2.26-2.22 (m, 1H), 2.13-2.11 (m, 1H), 1.65-1.62 (m, 1H), 1.53-1.50 (m, 4H), 1.40-1.33 (m, 5H), 1.28 (s, 3H). HRMS calculated for $C_{26}H_{28}N_5O_4IBr$ (M+H)$^+$: 680.0364; found 680.0362.

Ethyl (3aS,3bS,4aS,5R,5aR)-5-(6-((2-(3,4-difluorophenyl)cyclopropyl)amino)-2-iodo-9H-purin-9-yl)-2,2-dimethyltetrahydrocyclopropa[3,4]cyclopenta[1,2-d] [1,3]dioxole-3b(3aH)-carboxylate (55f)

Compound 55f (73%) was prepared from compound 52 following the same method for compound 55a. $^1$H NMR (CD$_3$OD, 400 MHz) δ 7.97 (s, 1H), 7.41 (s, 1H), 7.21-7.16 (m, 2H), 5.84 (d, J=7.2 Hz, 1H), 4.96 (s, 1H), 4.84-4.80 (m, 1H), 4.34-4.31 (m, 2H), 2.92 (br s, 1H), 2.26-2.21 (m, 1H), 2.15-2.06 (m, 1H), 1.65-1.62 (m, 1H), 1.53-1.50 (m, 4H), 1.41-1.32 (m, 5H), 1.29 s, 3H). HRMS calculated for $C_{26}H_{27}N_5O_4IF_2$ (M+H)$^+$: 638.1116; found 638.1100.

(3aS,3bS,4aS,5R,5aR)-5-(2-Iodo-6-((2-phenylcyclopropyl)amino)-9H-purin-9-yl)-N,2,2-trimethyltetrahydrocyclopropa[3,4]cyclopenta[1,2-d][1,3]dioxole-3b(3aH)-carboxamide (56 a)

Methylamine solution (40% aqueous, 2 mL) was added to a solution of compound 55a (40 mg, 0.066 mmol) in methanol (2 mL) and the mixture stirred at room temperature overnight. Solvent was evaporated under vacuum, and the residue was purified on flash silica gel column chromatography (CH$_2$Cl$_2$:MeOH=40:1) to give the compound 56a (28 mg, 71%) as a syrup. $^1$H NMR (CD$_3$OD, 400 MHz) δ 7.98 (s, 1H), 7.41-7.36 (m, 2H), 7.30 (t, J=7.2 Hz, 1H), 7.19 (t, J=7.2 Hz, 1H), 5.73 (d, J=6.8 Hz, 1H), 4.94 (s, 1H), 4.85-4.84 (m, 1H), 3.03 (br s, 1H), 2.91 (s, 3H), 2.15-2.11 (m, 2H), 1.54-1.50 (m, 4H), 1.41-1.36 (m, 2H), 1.35-1.26 (m, 4H). HRMS calculated for $C_{25}H_{28}N_6O_3I$ (M+H)$^+$: 587.1268; found 587.1287.

(3aS,3bS,4aS,5R,5aR)-5-(2-Iodo-6-((2-(m-tolyl)cyclopropyl)amino)-9H-purin-9-yl)-N,2,2-trimethyltetrahydrocyclopropa[3,4]cyclopenta[1,2-d][1,3] dioxole-3b(3 aH)-carboxamide (56b)

Compound 56b (65%) was prepared from compound 55b following the same method for compound 56a. $^1$H NMR (CD$_3$OD, 400 MHz) δ 7.98 (s, 1H), 7.25 (s, 1H), 7.18-7.11 (m, 2H), 7.00 (d, J=7.2 Hz, 1H), 5.73 (d, J=7.2 Hz, 1H), 4.94 (s, 1H), 4.84-4.83 (m, 1H), 3.07 (br s, 1H), 2.90 (d, J=1.6 Hz, 1H), 2.36 (s, H), 2.15-2.10 (m, 2H), 1.54-1.50 (m, 4H), 1.41-1.32 (m, 2H), 1.30-1.28 (m, 4H). HRMS calculated for $C_{25}H_{28}N_6O_3I$ (M+H)$^+$: 601.1419; found 601.1418.

(3aS,3bS,4aS,5R,5aR)-5-(6-((2-(3-Fluorophenyl)cyclopropyl)amino)-2-iodo-9H-purin-9-yl)-N,2,2-trimethyltetrahydrocyclopropa[3,4]cyclopenta[1,2-d][1,3]dioxole-3b (3aH)-carboxamide (56c)

Compound 56c (73%) was prepared from compound 55c following the same method for compound 56a. $^1$H NMR (CD$_3$OD, 400 MHz) δ 7.98 (s, 1H), 7.33-7.27 (m, 1H), 7.21-7.17 (m, 2H), 6.94-6.89 (m, 1H), 5.73 (d, J=7.2 Hz, 1H), 4.94 (s, 1H), 4.86-4.84 (m, 1H), 3.01 (br s, 1H), 2.90 (d, J=2.0 Hz, 3H), 2.16-2.11 (m, 2H), 1.54-1.50 (m, 4H), 1.41-1.34 (m, 3H), 1.29 (s, 3H). HRMS calculated for $C_{25}H_{27}N_6O_3IF$ (M+H)$^+$: 605.1168; found 605.1169.

(3aS,3bS,4aS,5R,5aR)-5-(6-((2-(3-Chlorophenyl)cyclopropyl)amino)-2-iodo-9H-purin-9-yl)-N,2,2-trimethyltetrahydrocyclopropa[3,4]cyclopenta[1,2-d][1,3]dioxole-3b (3aH)-carboxamide (56d)

Compound 56d (76%) was prepared from compound 55d following the same method for compound 56a. $^1$H NMR (CD$_3$OD, 400 MHz) δ 7.98 (s, 1H), 7.45 (s, 1H), 7.29-7.18 (m, 3H), 5.72 (d, J=7.2 Hz, 1H), 4.94 (s, 1H), 4.87-4.83 (m, 1H), 3.01 (br s, 1H), 2.90 (s, 3H), 2.15-2.11 (m, 2H), 1.54-1.50 (m, 4H), 1.41-1.37 (m, 3H), 1.31 (s, 3H). HRMS calculated for $C_{25}H_{27}N_6O_3ICl$ (M+H)$^+$: 621.0870; found 621.0872.

(3aS,3bS,4aS,5R,5aR)-5-(6-((2-(3-Bromophenyl)cyclopropyl)amino)-2-iodo-9H-purin-9-yl)-N,2,2-trimethyltetrahydrocyclopropa[3,4]cyclopenta[1,2-d] [1,3]dioxole-3b (3aH)-carboxamide (56e)

Compound 56e (65%) was prepared from compound 55e following the same method for compound 56a. $^1$H NMR (CD$_3$OD, 400 MHz) δ 7.98 (s, 1H), 7.61 (s, 1H), 7.36-7.34 (m, 2H), 7.22 (t, J=7.8 Hz, 1H), 5.72 (d, J=7.2 Hz, 1H), 4.94 (s, 1H), 4.85-4.83 (m, 1H), 2.96 (br s, 1H), 2.90 (s, 3H), 2.14-2.12 (m, 2H), 1.54-1.50 (m, 4H), 1.41-1.34 (m, 3H), 1.29 (s, 3H). HRMS calculated for $C_{25}H_{27}N_6O_3IBr$ (M+H)$^+$: 665.0373; found 665.0366.

(3aS,3bS,4aS,5R,5aR)-5-(6-((2-(3,4-Difluorophenyl)cyclopropyl)amino)-2-iodo-9H-purin-9-yl)-N,2,2-trimethyltetrahydrocyclopropa[3,4]cyclopenta[1,2-d][1,3]dioxole-3b(3aH)-carboxamide (56f)

Compound 56f (65%) was prepared from compound 55f following the same method for compound 56a. $^1$H NMR (CD$_3$OD, 400 MHz) δ 7.99 (s, 1H), 7.41 (s, 1H), 7.20-7.16 (m, 2H), 5.73 (d, J=7.2 Hz, 1H), 4.94 (s, 1H), 4.84 (d, J=7.2 Hz, 1H), 2.90 (s, 3H), 2.17-2.10 (m, 2H), 1.54-1.50 (m, 4H), 1.41-1.33 (m, 3H), 1.30 (s, 3H). HRMS calculated for C$_{25}$H$_{26}$N$_6$O$_3$IF$_2$ (M+H)$^+$: 623.1119; found 623.1100.

(3aS,3bS,4aS,5R, 5aR)—N,2,2-Trimethyl-5-(6-((2-phenylcyclopropyl)amino)-2-(phenylethynyl)-9H-purin-9-yl)tetrahydrocyclopropa[3,4]cyclopenta[1,2-d][1,3]dioxole-3b(3aH)-carboxamide (57a)

PdCl$_2$(PPh$_3$)$_2$ (3.8 mg, 0.005 mmol), CuI (1.0 mg, 0.005 mmol), phenylacetylene (18 μL, 0.16 mmol) and triethylamine (40 μL, 0.6 mmol) were added to a solution of compound 56a (27 mg, 0.06 mmol) in anhydrous DMF (1.0 mL), and the mixture stirred at room temperature overnight. Solvent was evaporated under vacuum, and the residue was purified by flash silica gel column chromatography (CH$_2$Cl$_2$:MeOH=35:1) to give the compound 57a (12 mg, 77%) as a syrup. $^1$H NMR (CD$_3$OD, 400 MHz) δ 8.01 (s, 1H), 7.70-7.68 (m, 2H), 7.49-7.45 (m, 4H), 7.36-7.35 (m, 2H), 7.31-7.25 (m, 2H), 5.81 (d, J=7.2 Hz, 1H), 5.04 (s, 1H), 2.80 (s, 3H), 2.24-2.14 (m, 2H), 1.57-1.54 (m, 4H), 1.44-1.41 (m, 2H), 1.38-1.27 (m, 4H). HRMS calculated for C$_{33}$H$_{33}$N$_6$O$_3$ (M+H)$^+$: 561.2614; found 561.2615.

(3aS,3bS,4aS,5R,5aR)-5-(6-((2-(3-Chlorophenyl)cyclopropyl)amino)-2-(phenylethynyl)-9H-purin-9-yl)-N,2,2-trimethyltetrahydrocyclopropa[3,4]cyclopenta[1,2-d][1,3]dioxole-3b(3aH)-carboxamide (57d)

Compound 57d (80%) was prepared from compound 56d following the same method for compound 57a. $^1$H NMR (CD$_3$OD, 400 MHz) δ 8.02 (s, 1H), 7.76-7.65 (m, 2H), 7.67-7.44 (m, 4H), 7.32-7.18 (m, 3H), 5.80 (d, J=7.2 Hz, 1H), 5.05 (s, 1H), 3.19 (br s, 1H), 2.78 (s, 3H), 2.29-2.13 (m, 2H), 1.61-1.54 (m, 4H), 1.44-1.37 (m, 3H), 1.31 (s, 3H). HRMS calculated for C$_{33}$H$_{32}$N$_6$O$_3$Cl (M+H)$^+$: 595.2224; found 595.2227.

(3aS,3bS,4aS,5R,5aR)-5-(6-((2-(3-Bromophenyl)cyclopropyl)amino)-2-(phenylethynyl)-9H-purin-9-yl)-N,2,2-trimethyltetrahydrocyclopropa[3,4]cyclopenta[1,2-d][1,3]dioxole-3b(3aH)-carboxamide (57e)

Compound 57e (78%) was prepared from compound 56e following the same method for compound 57a. $^1$H NMR (CD$_3$OD, 400 MHz) δ 8.17 (s, 1H), 7.70-7.67 (m, 2H), 7.54 (s, 1H), 7.46-7.44 (m, 3H), 7.36-7.33 (m, 2H), 7.22-7.17 (m, 1H), 5.81 (d, J=7.2 Hz, 1H), 5.04 (s, 1H), 3.20 (br s, 1H), 2.78 (s, 3H), 2.21-2.14 (m, 2H), 1.57-1.46 (m, 4H), 1.46-1.36 (m, 3H), 1.31 (s, 1H). HRMS calculated for C$_{33}$H$_{32}$N$_6$O$_3$Br (M+H)$^+$: 639.1719; found 639.1730.

(3aS,3bS,4aS,5R,5aR)-5-(6-((2-(3,4-Difluorophenyl)cyclopropyl)amino)-2-(phenylethynyl)-9H-purin-9-yl)-N,2,2-trimethyltetrahydrocyclopropa[3,4]cyclopenta[1,2-d][1,3]dioxole-3b(3aH)-carboxamide (57f)

Compound 57f (80%) was prepared from compound 56f following the same method for compound 57a. $^1$H NMR (CD$_3$OD, 400 MHz) δ 8.17 (s, 1H), 7.70-7.68 (m, 2H), 7.53-7.47 (m, 4H), 7.18-7.13 (m, 2H), 5.81 (d, J=7.2 Hz, 1H), 5.05 (s, 1H), 3.10 (br s, 1H), 2.79 (s, 3H), 2.21-2.16 (m, 2H), 1.59-1.53 (m, 4H), 1.45-1.36 (m, 3H), 1.31 (s, 3H). HRMS calculated for C$_{33}$H$_{31}$N$_6$O$_3$F$_2$ (M+H)$^+$: 597.2420; found 597.2420.

(1S,2R,3S,4R,5S)-2,3-Dihydroxy-N-methyl-4-(6-((2-phenylcyclopropyl)amino)-2-(phenylethynyl)-9H-purin-9-yl)bicyclo[3.1.0]hexane-1-carboxamide (21)

A solution of compound 57a (10 mg, 0.017 mmol) in methanol (2 mL) and 10% trifluoromethane sulfonic acid (2 mL) was heated at 70° C. for 5 h. Solvent was evaporated under vacuum, and the residue was purified on flash silica gel column chromatography (CH$_2$Cl$_2$:MeOH=25:1) to give the compound 21 (8 mg, 87%) as syrup. $^1$H NMR (CD$_3$OD, 400 MHz) δ 8.13 (s, 1H), 7.65-7.63 (m, 2H), 7.46 (d, J=1.6 Hz, 3H), 7.36 (d, J=7.6 Hz, 2H), 7.30-7.19 (m, 3H), 5.07 (d, J=6.0 Hz, 1H), 4.9 (s, 1H), 4.03 (d, J=6.8 Hz, 1H), 3.19 (br s, 1H), 2.85 (s, 3H), 2.25-2.20 (m, 1H), 2.13-2.10 (m, 1H), 1.88 (t, J=4.8 Hz, 1H), 1.45-1.39 (m, 2H), 1.37-1.28 (m, 1H). HRMS calculated for C$_{30}$H$_{29}$N$_6$O$_3$ (M+H)$^+$: 521.2301; found 521.2303.

(1S,2R,3S,4R,5S)-2,3-Dihydroxy-N-methyl-4-(2-(phenylethynyl)-6-((2-(m-tolyl)cyclopropyl)amino)-9H-purin-9-yl)bicyclo[3.1.0]hexane-1-carboxamide (22)

PdCl$_2$(PPh$_3$)$_2$ (5.9 mg, 0.008 mmol), CuI (1.0 mg, 0.005 mmol), 2-(m-tolyl)cyclopropan-1-amine (27 μL, 0.25 mmol) and triethylamine (60 μL, 0.43 mmol) were added to a solution of compound 56b (25.2 mg, 0.041 mmol) in anhydrous DMF (1 mL), and the mixture stirred at room temperature overnight. Solvent was evaporated under vacuum, and the residue was roughly purified on flash silica gel column chromatography. The resulting compound was dissolved in MeOH (2 mL) and 10% trifluoroacetic acid (2 mL) and heated at 70° C. for 5 h. Solvent was evaporated under vacuum, and the residue was purified on flash silica gel column chromatography (CH$_2$Cl$_2$:MeOH=25:1) to give the compound 6 (6.82 mg, 31%) as syrup. $^1$H NMR (CD$_3$OD, 400 MHz) δ 8.12 (s, 1H), 7.64-7.62 (m, 2H), 7.47-7.44 (m, 3H), 7.17-7.14 (m, 3H), 7.01 (d, J=6.8 Hz, 1H), 5.07 (d, J=6.8 Hz, 1H), 4.90 (s, 1H), 4.03 (d, J=6.8 Hz, 1H), 3.20 (br s, 1H), 2.84 (s, 3H), 2.30 (s, 3H), 2.21-2.16 (m, 1H), 2.13-2.10 (m, 1H), 1.88 (t, J=4.8 Hz, 1H), 1.43-1.38 (m, 2H), 1.32-1.28 (m, 1H). HRMS calculated for C$_{31}$H$_{31}$N$_6$O$_3$ (M+H)$^+$: 535.2458; found 535.2462.

(1S,2R,3S,4R,5S)-4-(6-((2-(3-Fluorophenyl)cyclopropyl)amino)-2-(phenylethynyl)-9H-purin-9-yl)-2,3-dihydroxy-N-methylbicyclo[3.1.0]hexane-1-carboxamide (23)

Compound 23 (62%) was prepared from compound 56c following the same method for compound 22. $^1$H NMR (CD$_3$OD, 400 MHz) δ 8.13 (s, 1H), 7.68-7.62 (m, 2H), 7.46-7.44 (m, 3H), 7.31-7.26 (m, 1H), 7.18-7.16 (m, 2H), 6.95-6.90 (m, 1H), 5.06 (d, J=5.2 Hz, 1H), 4.90 (s, 1H), 4.03 (d, J=6.0 Hz, 1H), 3.15 (br s, 1H), 2.26-2.21 (m, 1H), 2.14-2.10 (m, 1H), 1.88 (t, J=4.8 Hz, 1H), 1.47-1.39 (m, 3H). HRMS calculated for C$_{30}$H$_{28}$N$_6$O$_3$F (M+H)$^+$: 539.2207; found 539.2214.

(1S,2R,3S,4R,5S)-4-(6-((2-(3-Chlorophenyl)cyclopropyl)amino)-2-(phenylethynyl)-9H-purin-9-yl)-2,3-dihydroxy-N-methylbicyclo[3.1.0]hexane-1-carboxamide (24)

A solution of compound 57d (34 mg, 0.057 mmol) in methanol (2 mL) and 10% trifluoromethane sulfonic acid (2 mL) was heated at 70° C. for 5 h. Solvent was evaporated under vacuum, and the residue was purified on flash silica gel column chromatography (CH$_2$Cl$_2$:MeOH=30:1) to give the compound 24 (11 mg, 31%) as syrup, which upon further elution with (CH$_2$Cl$_2$:MeOH=15:1) gave the compound 28 (6 mg, 25%) as a syrup. Data for compound 24: $^1$H NMR (CD$_3$OD, 400 MHz) δ 8.12 (s, 1H), 7.78 (d, J=4.0 Hz, 1H), 7.64-7.62 (m, 2H), 7.46-7.41 (m, 3H), 7.31-7.19 (m, 3H), 5.06 (d, J=6.4 Hz, 1H), 4.90 (s, 1H), 4.03 (d, J=6.8 Hz, 1H), 3.15 (br s, 1H), 2.84 (d, J=4.4 Hz, 3H), 2.21-2.19 (m, 1H), 2.13-2.10 (m, 1H), 1.88 (t, J=4.8 Hz, 1H), 1.44-1.39. HRMS calculated for $C_{30}H_{28}N_6O_3C_1$ (M+H)$^+$: 555.1911; found 555.1921. Data for compound 28: $^1$H NMR (CD$_3$OD, 400 MHz) δ 8.19 (s, 1H), 7.65-7.63 (m, 2H), 7.46-7.44 (m, 3H), 5.08 (d, J=5.6 Hz, 1H), 4.90 (s, 1H), 4.04 (d, J=6.4 Hz, 1H), 2.84 (s, 3H), 2.14-2.10 (m, 1H), 1.88 (t, J=4.8 Hz, 1H), 1.42-1.40 (m, 1H). HRMS calculated for $C_{21}H_{21}N_6O_3$ (M+H)$^+$: 405.1675; found 405.1668.

(1S,2R,3S,4R,5S)-4-(6-((2-(3-Bromophenyl)cyclopropyl)amino)-2-(phenylethynyl)-9H-purin-9-yl)-2,3-dihydroxy-N-methylbicyclo[3.1.0]hexane-1-carboxamide (25)

Compound 25 (66%) was prepared from compound 57e following the same method for compound 21. $^1$H NMR (CD$_3$OD, 400 MHz) δ 8.12 (s, 1H), 7.64-7.62 (m, 2H), 7.55 (s, 1H), 7.45-7.43 (m, 3H), 7.34 (d, J=7.6 Hz, 2H), 7.19 (t, J=8.0 Hz, 1H), 5.05 (d, J=6.4 Hz, 1H), 4.89 (s, 1H), 4.02 (d, J=6.8 Hz, 1H), 3.18 (br s, 1H), 2.84 (s, 3H), 2.20-2.21 (m, 1H), 2.13-2.10 (m, 1H), 1.88 (t, J=4.8 Hz, 1H), 1.45-1.38 (m, 3H). HRMS calculated for $C_{30}H_{28}N_6O_3Br$ (M+H)$^+$: 599.1401; found 599.1403.

(1S,2R,3S,4R,5S)-4-(6-((2-(3,4-Difluorophenyl)cyclopropyl)amino)-2-(phenylethynyl)-9H-purin-9-yl)-2,3-dihydroxy-N-methylbicyclo[3.1.0]hexane-1-carboxamide (26)

Compound 26 (59%) was prepared from compound 57f following the same method for compound 21. $^1$H NMR (CD$_3$OD, 400 MHz) δ 8.16 (s, 1H), 7.66-7.64 (m, 2H), 7.47-7.45 (m, 4H), 7.18-7.13 (m, 2H), 5.07 (d, J=5.2 Hz, 1H), 4.91 (s, 1H), 4.04 (d, J=6.8 Hz, 1H), 3.14 (br s, 1H), 2.22-2.18 (m, 1H), 2.13-2.10 (m, 1H), 1.89 (t, J=4.8 Hz, 1H), 1.43-1.37 (m, 3H). HRMS calculated for $C_{30}H_{27}N_6O_3F_2$ (M+H)$^+$: 557.2107; found 557.2109.

(1S,2R,3S,4R,5S)-4-(6-((2-(3,4-Difluorophenyl)cyclopropyl)amino)-2-(pyridin-2-ylethynyl)-9H-purin-9-yl)-2,3-dihydroxy-N-methylbicyclo[3.1.0]hexane-1-carboxamide (27)

Compound 27 (64%) was prepared from compound 56f following the same method for compound 22. $^1$H NMR (CD$_3$OD, 400 MHz) δ 8.64 (s, 1H), 8.17 (s, 1H), 7.95 (t, J=8.0 Hz, 1H), 7.76 (d, J=8.0 Hz, 1H), 7.53-7.41 (m, 2H), 7.19-7.14 (m, 2H), 5.16 (d, J=6.4 Hz, 1H), 4.91 (s, 1H), 4.06 (d, J=6.8 Hz, 1H), 3.18 (s, 1H), 2.83 (s, 3H), 2.18-2.15 (m, 1H), 2.10-2.07 (m, 1H), 1.85 (t, J=4.8 Hz, 1H), 1.42-1.36 (m, 2H), 1.19-1.04 (m, 1H). HRMS calculated for $C_{29}H_{26}N_7O_3F_2$(M+H)$^+$: 558.2065; found 558.2046.

Ethyl (3aS,3bS,4aS,5R,5aR)-5-(2,6-bis(phenylethynyl)-9H-purin-9-yl)-2,2-dimethyl tetrahydrocyclopropa[3,4]cyclopenta[1,2-d][1,3]dioxole-3b(3aH)-carboxylate (58a)

PdCl$_2$(PPh$_3$)$_2$ (14 mg, 0.02 mmol), CuI (1.9 mg, 0.01 mmol), phenylacetylene (66 L, 0.16 mmol) and triethylamine (0.14 mL, 1.0 mmol) were added to a solution of compound 52a (50.6 mg, 0.10 mmol) in anhydrous DMF (2.0 mL), and the mixture stirred at room temperature overnight. Solvent was evaporated under vacuum, and the residue was purified on flash silica gel column chromatography (hexane:ethylacetate=1:1) to give the compound 58a (46 mg, 84%) as a syrup.

$^1$H NMR (CDCl$_3$, 400 MHz) δ 8.14 (s, 1H), 7.77-7.75 (m, 4H), 7.44-7.28 (m, 6H), 5.96 (d, J=7.2 Hz, 1H), 5.08 (s, 1H), 4.81 (d, J=6.4 Hz, 1H), 4.25-4.22 (m, 2H), 2.32-2.29 (m, 1H), 1.82-1.78 (m, 1H), 1.60 (s, 3H), 1.33 (s, 3H), 1.29-1.26 (m, 1H), 1.22 (t, J=7.2 Hz, 3H). HRMS calculated for $C_{33}H_{29}N_4O_4$ (M+H)$^+$: 545.2189; found 545.2197.

Ethyl (3aS,3bS,4aS,5R,5aR)-5-(2,6-bis((4-(tert-butyl)phenyl)ethynyl)-9H-purin-9-yl)-2,2-dimethyltetrahydrocyclopropa[3,4]cyclopenta[1,2-d][1,3]dioxole-3b(3aH)-carboxylate (58b)

Compound 58b (86%) was prepared from compound 52a following the same method for compound 58a. $^1$H NMR (CD$_3$OD, 400 MHz) δ 8.61 (s, 1H), 7.72 (d, J=2.8, J$_2$=8.4 Hz, 4H), 7.54 (t, J=8.4 Hz, 4H), 5.97 (d, J=6.8 Hz, 1H), 5.16 (s, 1H), 4.97 (d, J=6.0 Hz, 1H), 4.27-4.17 (m, 2H), 2.43-2.39 (m, 1H), 1.75-1.71 (m, 1H), 1.60-1.56 (m, 4H), 1.38 (s, 18H), 1.32 (s, 3H), 1.18 (t, J=6.8 Hz, 3H). HRMS calculated for $C_{41}H_{45}N_4O_4$ (M+H)$^+$: 657.3441; found 657.3446.

Ethyl (3aR,3bS,4aS,5R,5aS)-5-(2,6-bis((2-chlorophenyl)ethynyl)-9H-purin-9-yl)-2,2-dimethyltetrahydrocyclopropa[3,4]cyclopenta[1,2-d][1,3]dioxole-3b(3aH)-carboxylate (58c)

Compound 58c (82%) was prepared from compound 52a following the same method for compound 58a. $^1$H NMR (CD$_3$OD, 400 MHz) δ 8.65 (s, 1H), 7.91-7.88 (m, 2H), 7.60-7.51 (m, 2H), 7.50-7.40 (m, 4H), 5.99 (d, J=7.2 Hz, 1H), 5.18 (s, 1H), 5.01 (d, J=6.0 Hz, 1H), 4.21-4.10 (m, 2H), 2.43-2.39 (m, 1H), 1.74-1.70 (m, 1H), 1.60-1.56 (m, 4H), 1.31 (s, 3H), 1.15 (t, J=7.2 Hz, 3H). HRMS calculated for $C_{33}H_{27}N_4O_4Cl_2$ (M+H)$^+$: 613.1409; found 613.1400.

Ethyl (3aR,3bS,4aS,5R,5aS)-5-(2-chloro-6-(phenylethynyl)-9H-purin-9-yl)-2,2-dimethyltetrahydrocyclopropa[3,4]cyclopenta[1,2-d][1,3]dioxole-3b(3aH)-carboxylate (60)

Compound 60 (85%) was prepared from compound 52b following the same method for compound 58a. $^1$H NMR (CD$_3$OD, 400 MHz) δ 8.59 (s, 1H), 7.80 (d, J=6.8 Hz, 1H), 7.53-7.50 (m, 4H), 5.88 (d, J=7.2 Hz, 1H), 5.13 (s, 1H), 4.92-4.88 (m 1H), 4.28-4.25 (m, 2H), 2.40-2.36 (m, 1H), 1.73-1.70 (m, 1H), 1.59-1.55 (m, 4H), 1.34 (t, J=7.2 Hz, 3H), 1.30 (s, 3H). HRMS calculated for $C_{25}H_{24}N_4O_4C_1$ (M+H)$^+$: 479.1481; found 479.1482.

(3aS,3bS,4aS,5R,5aR)—N,2,2-trimethyl-5-(6-((Z)-2-(methylamino)-2-phenylvinyl)-2-(phenylethynyl)-9H-purin-9-yl)tetrahydrocyclopropa[3,4]cyclopenta[1,2-d][1,3]dioxole-3b(3aH)-carboxamide (59a)

40% Methylamine solution (2.5 mL) was added to a solution of compound 58a (46 mg, 0.084 mmol) in methanol (3.0 mL) and the mixture stirred at room temperature overnight. Solvent was evaporated under vacuum, and the residue was purified on flash silica gel column chromatography (CH$_2$Cl$_2$:MeOH=40:1) to give the compound 59a (32 mg, 68%) as a fluorescent yellow syrup. $^1$H NMR (CDCl$_3$, 400 MHz) δ 10.27 (d, J=5.2 Hz, 1H), 7.85 (s, 1H), 7.71-7.68 (m, 2H), 7.50-7.45 (m, 8H), 5.83 (s, 1H), 5.81 (s, 1H), 4.90 (d, J=6.8 Hz, 1H), 4.87 (s, 1H), 3.02 (d, J=5.2 Hz, 3H), 2.85 (d, J=4.8 Hz, 3H), 2.03-1.99 (m, 1H), 1.73-1.69 (m, 1H), 1.68-1.55 (m, 4H), 1.32 (s, 3H). HRMS calculated for $C_{33}H_{33}N_6O_3$ (M+H)$^+$: 561.2614; found 561.2612.

(3aS,3bS,4aS,5R,5aR)-5-(6-((Z)-2-(4-(tert-Butyl)phenyl)-2-(methylamino)vinyl)-2-((4-(tert-butyl)phenyl)ethynyl)-9H-purin-9-yl)-N,2,2-trimethyltetrahydrocyclopropa[3,4]cyclopenta [1,2-d][1,3]dioxole-3b(3aH)-carboxamide (59b)

Compound 59b (71%) was prepared from compound 58b following the same method for compound 59a. $^1$H NMR (CDCl$_3$, 400 MHz) δ 10.28 (d, J=5.2 Hz, 1H), 7.84 (s, 1H), 7.62 (d, J=8.4 Hz, 2H), 7.47-7.44 (m, 8H), 8.32 (d, J=7.2 Hz, 1H), 5.80 (s, 1H), 4.88 (d, J=6.0 Hz, 1H), 4.85 (s, 1H), 3.04 (d, J=5.2 Hz, 3H), 2.87 (d, J=4.8 Hz, 3H), 2.01-1.97 (m, 1H), 1.72-1.68 (m, 1H), 1.58 (s, 3H), 1.37 (s, 18H), 1.35-1.30 (m, 4H). HRMS calculated for $C_{41}H_{49}N_6O_3$(M+H)$^+$: 673.3866; found 673.3876.

(3aS,3bS,4aS,5R,5aR)-5-(6-((Z)-2-(2-Chlorophenyl)-2-(methylamino)vinyl)-2-((2-chlorophenyl)ethynyl)-9H-purin-9-yl)-N,2,2-trimethyltetrahydrocyclopropa[3,4]cyclopenta [1,2-d][1,3]dioxole-3b(3aH)-carboxamide (59c)

Compound 59c (72%) was prepared from compound 58c following the same method for compound 59a. $^1$H NMR (CDCl$_3$, 400 MHz) δ 10.41 (s, 1H), 7.86 (s, 1H), 7.72 (d, J=6.0 Hz, 1H), 7.54-7.47 (m, 2H), 7.42-7.38 (m, 5H), 5.83 (d, J=6.8 Hz, 1H), 5.69 (s, 1H), 4.91 (t, J=7.2 Hz, 1H), 4.86 (s, 1H), 2.91 (d, J=5.2 Hz, 3H), 2.83 (d, J=4.8 Hz, 3H), 2.04-1.97 (m, 1H), 1.72-1.69 (m, 1H), 1.58 (s, 3H), 1.30-1.32 (m, 4H). HRMS calculated for $C_{33}H_{31}N_6O_3Cl_2$ (M+H)$^+$: 629.1829; found 629.1835.

(3aS,3bS,4aS,5R,5aR)-5-(2-Chloro-6-((Z)-2-(methylamino)-2-phenylvinyl)-9H-purin-9-yl)-N,2,2-trimethyltetrahydrocyclopropa[3,4]cyclopenta[1,2-d][1,3]dioxole-3b (3aH)-carboxamide (61)

Compound 61 (70%) was prepared from compound 60 following the same method for compound 59a. $^1$H NMR (CDCl$_3$, 400 MHz) δ 9.98 (s, 1H), 7.78 (s, 1H), 7.49-7.46 (m, 5H), 6.95 (d, J=4.4 Hz, 1H), 5.76 (s, 1H), 5.70 (d, J=6.8 Hz, 1H), 4.83-4.80 (m, 2H), 3.01 (d, J=5.2 Hz, 3H), 2.95 (d, J=4.8 Hz, 1H), 2.08-2.04 (m, 1H), 1.72-1.68 (m, 1H), 1.57 (s, 3H), 1.34-1.30 (m, 4H). HRMS calculated for $C_{25}H_{28}N_6O_3C_1$ (M+H)$^+$: 495.1906; found 495.1907.

(1S,2S,3R,4R,5S)-2,3-Dihydroxy-4-(6-((Z)-2-hydroxy-2-phenylvinyl)-2-(phenylethynyl)-9H-purin-9-yl)-N-methylbicyclo[3.1.0]hexane-1-carboxamide (38)

A solution of compound 59a (32 mg, 0.057 mmol) in methanol (3.0 mL) and 10% trifluoromethane sulfonic acid (2.5 mL) was heated at 70° C. overnight. Solvent was evaporated under vacuum, and the residue was purified on flash silica gel column chromatography (CH$_2$Cl$_2$: MeOH=25:1) to give the compound 38 (9 mg, 31%) as yellow syrup, which upon further elution with (CH$_2$Cl$_2$: MeOH=12:1) gave the compound 39 (6 mg, 26%) as a colorless syrup. Data for compound 38: $^1$H NMR (CD$_3$OD, 400 MHz) δ 8.43 (s, 1H), 8.01-7.99 (m, 2H), 7.73 (dd, J$_1$=1.6, J$_2$=5.6 Hz, 2H), 7.52-7.49 (m, 6H), 6.84 (s, 1H), 5.13 (d, J=5.6 Hz, 1H), 4.99 (s, 1H), 4.12 (d, J=6.8 Hz, 1H), 2.85 (s, 3H), 2.18-2.15 (m, 1H), 1.89 (t, J=4.8 Hz, 1H), 1.44-1.40 (m, 1H). HRMS calculated for $C_{29}H_{26}N_5O_4$ (M+H)$^+$: 508.1985; found 508.1991.

Data for compound (1S,2S,3R,4R,5S)-2,3-dihydroxy-N-methyl-4-(6-methyl-2-(phenylethynyl)-9H-purin-9-yl)bicyclo[3.1.0]hexane-1-carboxamide (39): $^1$H NMR (CD$_3$OD, 400 MHz) δ 8.52 (s, 1H), 7.70-7.67 (m, 2H), 7.48-7.46 (m, 3H), 5.15 (d, J=5.2 Hz, 1H), 5.00 (s, 1H), 4.11 (d, J=6.4 Hz, 1H), 2.85 (s, 3H), 2.83 (s, 3H), 2.16-2.13 (m, 1H), 1.88 (t, J=4.8 Hz, 1H), 1.43-1.39 (m, 1H). HRMS calculated for $C_{22}H_{22}N_5O_3$ (M+H)$^+$: 404.1723; found 404.1719.

(1S,2S,3R,4R,5S)-4-(6-((Z)-2-(4-(tert-Butyl)phenyl)-2-hydroxyvinyl)-2-((4-(tert-butyl)phenyl)ethynyl)-9H-purin-9-yl)-2,3-dihydroxy-N-methylbicyclo[3.1.0]hexane-1-carboxamide (40)

Compound 40 (32%) and 41 (21%) were prepared from compound 59b following the same method for compound 38 and 39. Data for compound 40: $^1$H NMR (CD$_3$OD, 400 MHz) δ 8.36 (s, 1H), 7.91 (d, J=4.8 Hz, 2H), 7.64-7.62 (m, 2H), 4.55-7.52 (m, 4H), 6.75 (s, 1H), 5.09 (d, J=5.6 Hz, 1H), 4.95 (s, 1H), 4.10 (d, J=6.4 Hz, 1H), 2.85 (s, 3H), 2.17-2.13 (m, 1H), 1.88 (t, J=5.2 Hz, 1H), 1.38-1.37 (m, 19H). HRMS calculated for $C_{37}H_{42}N_5O_4$ (M+H)$^+$: 620.3237; found 620.3232. Data for compound (1S,2S,3R,4R,5S)-4-(2-((4-(tert-butyl)phenyl) ethynyl)-6-methyl-9H-purin-9-yl)-2,3-dihydroxy-N-methylbicyclo[3.1.0]hexane-1-carboxamide (41): $^1$H NMR (CD$_3$OD, 400 MHz) δ 8.51 (s, 1H), 7.62 (d, J=8.4 Hz, 2H), 7.52 (d, J=8.4 Hz, 2H), 5.15 (d, J=5.2 Hz, 1H), 5.00 (s, 1H), 4.11 (d, J=5.2 Hz, 1H), 2.86 (s, 3H), 2.83 (s, 3H), 2.16-2.13 (m, 1H), 1.88 (t, J=4.8 Hz, 1H), 1.44-1.40 (m, 1H), 1.37 (s, 18H). HRMS calculated for $C_{26}H_{30}N_5O_3$ (M+H)$^+$: 460.2349; found 460.2341.

(1S,2S,3R,4R,5S)-4-(6-((Z)-2-(2-Chlorophenyl)-2-hydroxyvinyl)-2-((2-chlorophenyl) ethynyl)-9H-purin-9-yl)-2,3-dihydroxy-N-methylbicyclo[3.1.0]hexane-1-carboxamide (42)

Compound 42 (72%) was prepared from compound 59c following the same method for compound 38, and no C6-methyl product was detected. $^1$H NMR (CD$_3$OD, 400 MHz) δ 8.43 (s, 1H), 7.78 (d, J=6.0 Hz, 1H), 7.68-7.60 (m, 1H), 7.58 (d, J=7.2 Hz, 1H), 7.53-7.42 (m, 5H), 6.47 (s, 1H), 5.14 (d, J=5.6 Hz, 1H), 5.00 (s, 1H), 4.13 (d, J=6.4 Hz, 1H), 2.84 (s, 3H), 2.18-2.14 (m, 1H), 1.88 (d, J=4.8 Hz, 1H), 1.44-1.40 (m, 1H). HRMS calculated for $C_{29}H_{24}N_5O_4Cl_2$ (M+H)$^+$: 576.1205; found 576.1208.

(1 S,2S,3R,4R,5S)-4-(2-Chloro-6-((Z)-2-hydroxy-2-phenylvinyl)-9H-purin-9-yl)-2,3-dihydroxy-N-methylbicyclo[3.1.0]hexane-1-carboxamide (43)

Compound 43 (75%) was prepared from compound 61 following the same method for compound 38, and no C6-methyl product was detected. $^1$H NMR (CD$_3$OD, 400 MHz) δ 8.43 (s, 1H), 7.99-7.97 (m, 2H), 7.52-7.50 (m, 3H), 6.87 (s, 1H), 5.13 (d, J=6.4 Hz, 1H), 4.93 (s, 1H), 4.08 (d, J=6.8 Hz, 1H), 2.90 (s, 3H), 2.14-2.11 (m, 1H), 1.85 (d, J=4.8 Hz, 1H), 1.43-1.39 (m, 1H). HRMS calculated for $C_{21}H_{21}N_5O_4C_1$ (M+H)$^+$: 442.1277; found 442.1279.

Example 3

This example illustrates the performance of compounds in accordance with an embodiment of the invention in an in vivo model of neuropathic pain.

Experimental Animals.

Male CD-1 mice (25-30 g) from Harlan (Indianapolis, Ind.) were housed 4-5 (for mice) per cage in a controlled environment (12 h light/dark cycles) with food and water available ad libitum. Experiments were performed in accordance with International Association for the Study of Pain, NIH guidelines on laboratory animal welfare and Saint Louis University Institutional Animal Care and Use Committee recommendations. Experimenters were blinded to treatment conditions in all experiments.

CCI Model Ofneuropathic Pain.

CCI to the sciatic nerve of the left hind leg in mice was performed under general anaesthesia using the well characterized Bennett model (Bennett, G. J. et al., *Pain* 1988, 33, 87-107). Briefly, mice (weighing 25-30 g at the time of surgery) were anesthetized with 3% isoflurane/100% O$_2$ inhalation and maintained on 2% isoflurane/100% O$_2$ for the duration of surgery. The left thigh was shaved, scrubbed with Nolvasan (Zoetis, Madison, N.J.), and a small incision (1-1.5 cm in length) was made in the middle of the lateral aspect of the left thigh to expose the sciatic nerve. The nerve was loosely ligated around the entire diameter of the nerve at three distinct sites (spaced 1 mm apart) using silk sutures (6.0). The surgical site was closed with a single muscle suture and a skin clip. Pilot studies established that under the experimental conditions peak mechano-allodynia develops by day 5-day 7 following CCI. Test substances or their vehicles were administered as 3 µmol/kg doses given by gavage (0.2 ml p.o.) at peak mechano-allodynia (day 7). The vehicle used consisted of 10% DMSO in 0.5% methylcellulose (diluted from a 5 mM stock solution in DMSO). Methylcellulose (Lot number 021M0067V) was obtained from Sigma viscosity 400 cP and prepared in sterile distilled water (UPS).

Statistical Analysis for In Vivo Experiments.

Data are expressed as mean±SEM for n animals. Behavioral data were analyzed by two-way ANOVA with Bonferroni comparisons. Significant differences were defined at a P<0.05. All statistical analysis was performed using GraphPad Prism (v5.03, GraphPad Software, Inc., San Diego, Calif.).

The assay was performed as described in Chen, Z. et al., FASEB J. 2012, 26, 1855-1865 and Paoletta, S. et al., J. Med. Chem. 2013, 56, 5949-5963.

Figure 1A:
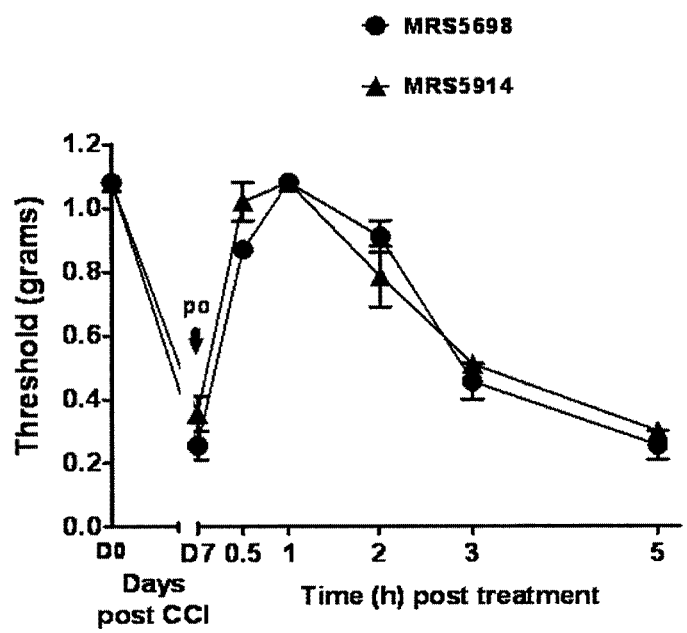
FIGS. 1A-1C illustrate the reversal of mechano-allodynia over time exhibited by compounds 7 (MRS5914), 8 (MRS5917), and 17 (MRS5969), respectively, in a chronic constriction injury model of neuropathic pain.
Figure 1B:
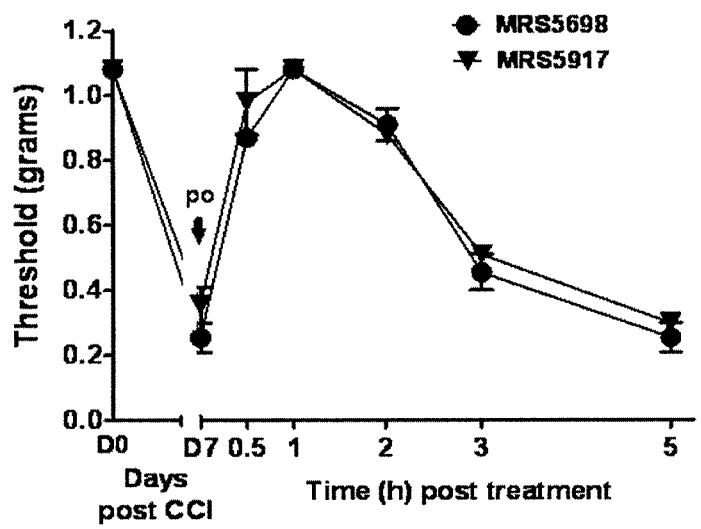
Figure 1C:
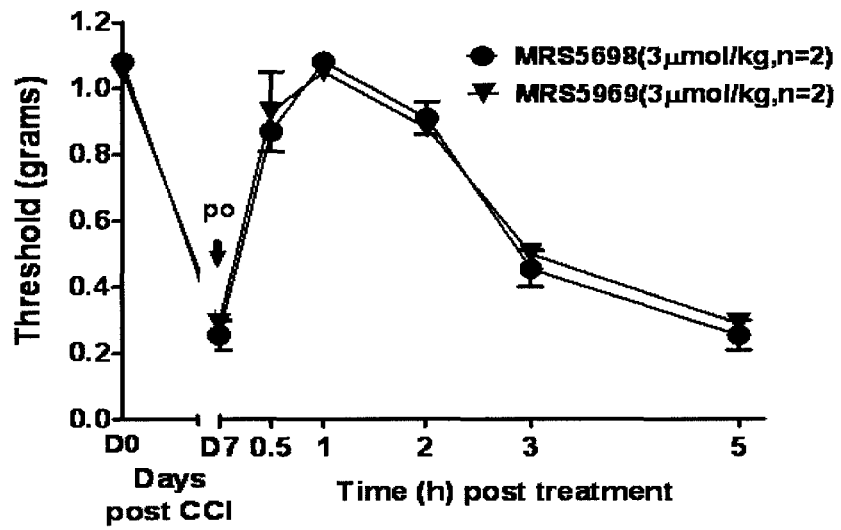
Figure 2:
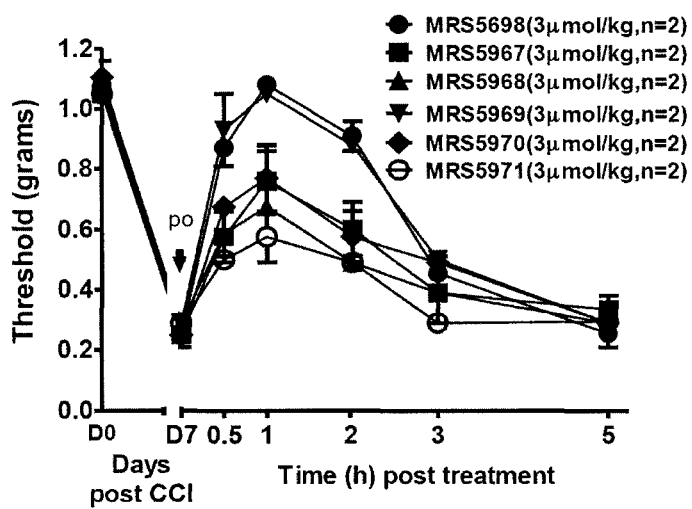
FIG. 2 illustrates the reversal of mechano-allodynia over time exhibited by compounds 13 (MRS5967), 16 (MRS5968), 17 (MRS5969), 14 (MRS5970), and 11 (MRS5971) in a chronic constriction injury model of neuropathic pain.
Figure 3:
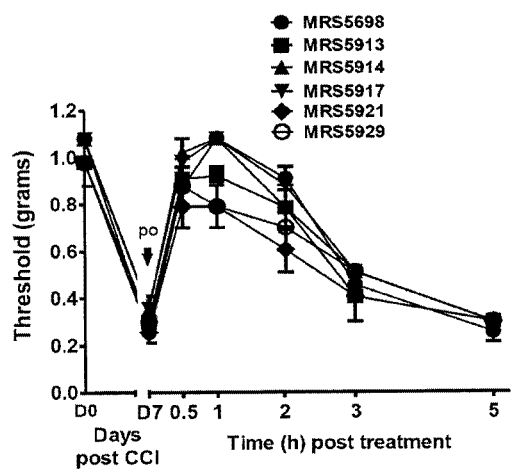
FIG. 3 illustrates reversal of mechano-allodynia over time exhibited by compounds 6 (MRS5913), 7 (MRS5914), 8 (MRS5917), 9 (MRS5921), and 10 (MRS5929) in a chronic constriction injury model of neuropathic pain.
Figure 4:
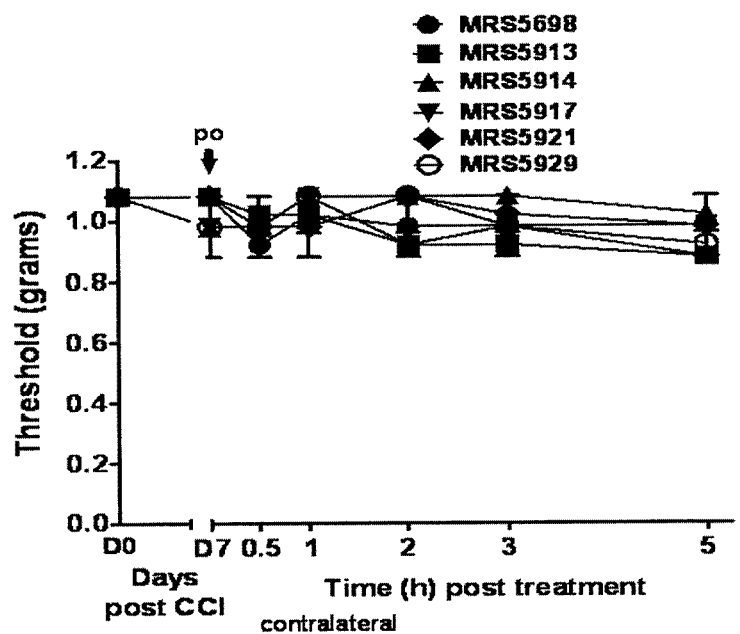
FIG. 4 illustrates the reversal of mechano-allodynia over time exhibited by compounds 6 (MRS5913), 7 (MRS5914), 8 (MRS5917), 9 (MRS5921), and 10 (MRS5929) at the contralateral side in a chronic constriction injury model of neuropathic pain.
Figure 5:
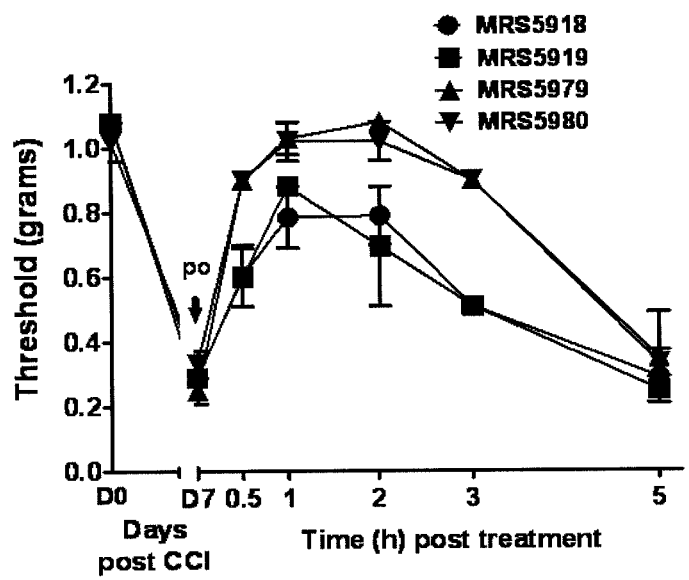
FIG. 5 illustrates the reversal of mechano-allodynia over time exhibited by compounds 40 (MRS5918), 41 (MRS5919), 37 (MRS5979), and 32 (MRS5980) in a chronic constriction injury model of neuropathic pain.
Figure 6:
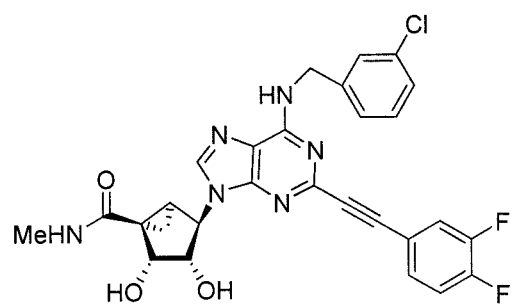
FIG. 6 depicts the structures of MRS5698 and MRS5676.
Figure 6:
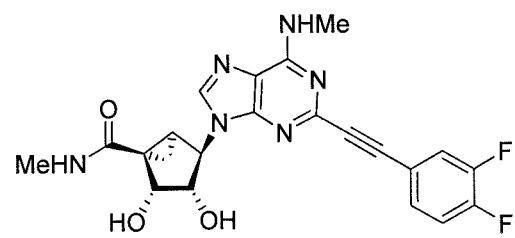
Figure 7A:
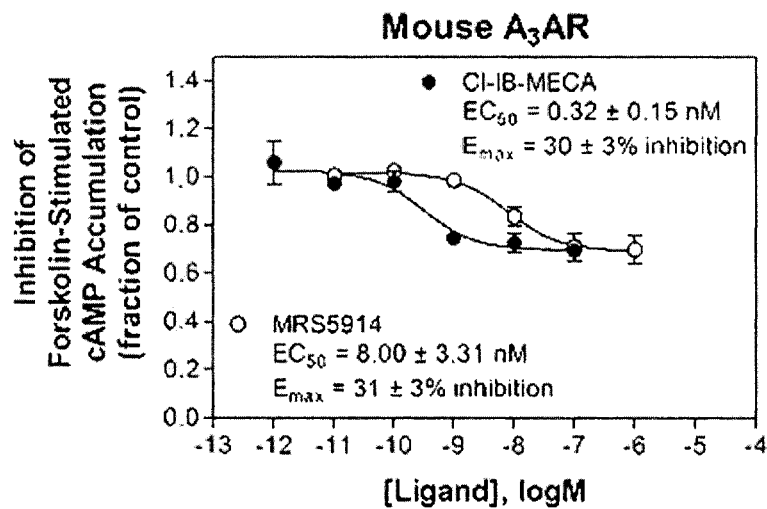
FIGS. 7A-7F illustrate concentration-effect curves for compounds 7, 8, 40, 41, 32, and 101, respectively, in an assay of inhibition of forskolin-stimulated cAMP accumulation with HEK293 cells expressing the mA$_1$AR.
Figure 7B:
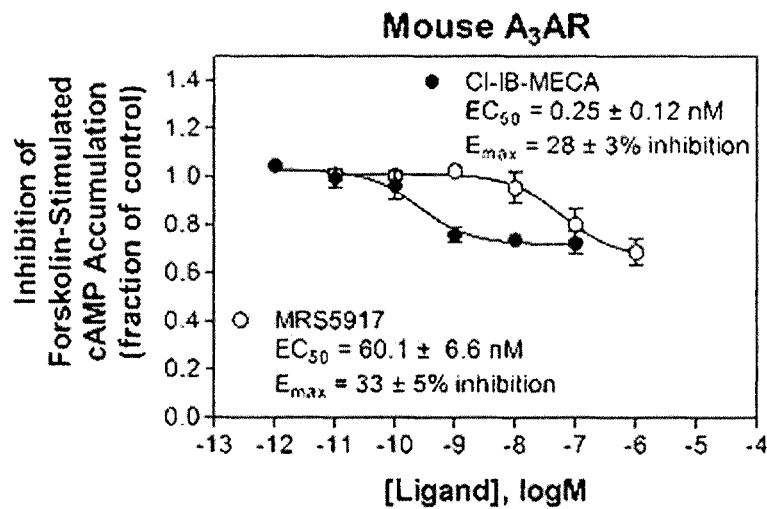
Figure 7C:
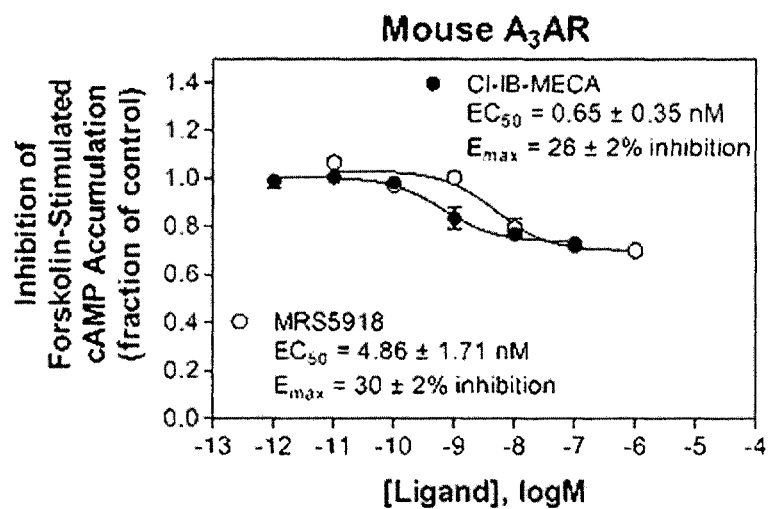
Figure 7D:
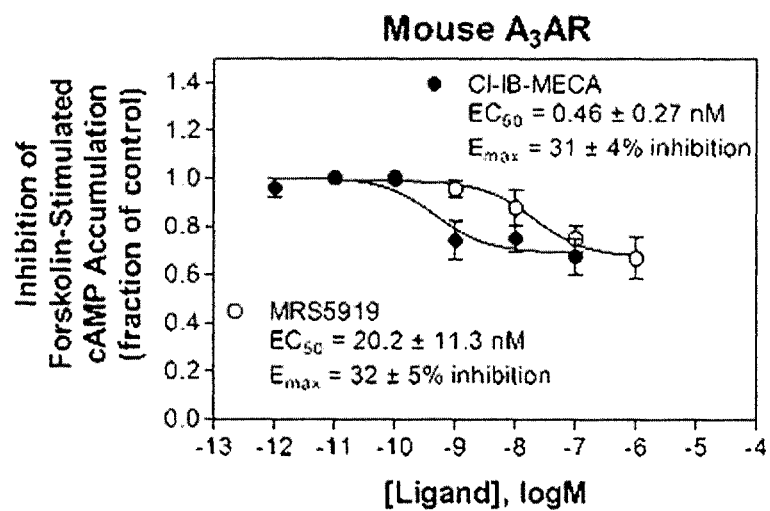
Figure 7E:
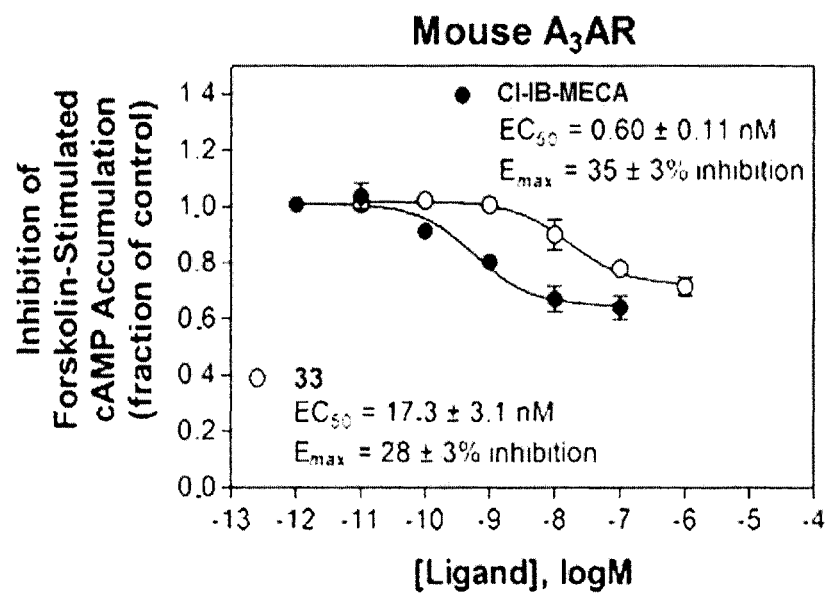
Figure 7F:
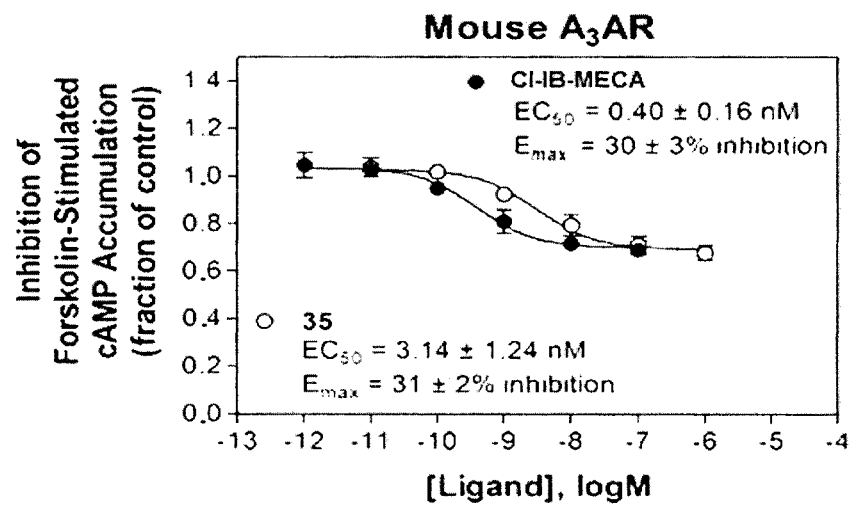

The results are set forth in Tables 6 and 7. The reversal of mechano-allodynia over time exhibited by compounds 7 (MRS5914), 8 (MRS5917), and 17 (MRS5969) are illustrated in FIGS. 1A-1C, respectively. The reversal of mcchano-allodynia over time exhibited by compounds 13 (MRS5967), 16 (MRS5968), 17 (MRS5969), 14 (MRS5970), and 11 (MRS5971) are depicted in FIG. 2. The reversal of mechano-allodynia over time exhibited by compounds 6 (MRS5913), 7 (MRS5914), 8 (MRS5917), 9 (MRS5921), and 10 (MRS5929) are depicted in FIG. 3. The structure of MRS5698 (reference) is depicted in FIG. 6. The reversal of mechano-allodynia over time exhibited by compounds 7, 17, and 32 at doses of 0.3 mmol/kg, 1 mmol/kg, and 3 mmol/kg is depicted in FIGS. 8A-8C. The reversal of mechano-allodynia over time exhibited by compounds 40 (MRS5918), 41 (MRS5919), 37 (MRS5979), and 32 (MRS5980) in a chronic constriction injury model of neuropathic pain are illustrated in FIG. 5. The reversal of mechano-allodynia over time exhibited by compounds 8, 16, and 100 in a chronic constriction injury model of neuropathic pain are illustrated in FIG. 10. The reversal of mechano-allodynia over time exhibited by compounds 100 (MRS7110), 105 (MRS7113), 103 (MRS7114), 101 (MRS7115), and 104 (MRS7116,) respectively, in a chronic constriction injury model of neuropathic pain are illustrated in FIG. 11. The reversal of mechano-allodynia over time exhibited by compounds 112 (MRS7121), 102 (MRS7117), 108 (MRS7118), 111 (MRS7119), 106 (MRS7120), and 110 (MRS7126), respectively, in a chronic constriction injury model of neuropathic pain are illustrated in FIG. 12. The reversal of mechano-allodynia over time exhibited by compound 126 (MRS7135) on oral dosing at 0.3, 1, 2, 10, and 30 µmol/kg dosing is illustrated in FIG. 16. The reversal of mechano-allodynia over time exhibited by compounds 125 (MRS7137), 120 (MRS7138), 121 (MRS7139), and 127 (MRS7140,) respectively, in a chronic constriction injury model of neuropathic pain are illustrated in FIG. 17.

TABLE 6

Activity of orally administered AR agonists (3 µmol/kg) in CCI model of neuropathic pain in mice

| Cmpd. | Time of peak protection (h) | Max. effect $E_{max}$ (% ± SEM) | Effect at 3 h (% ± SEM) | Mol. Wt. | cLogP[b] | tPSA (Å$^2$) |
|---|---|---|---|---|---|---|
| 6 | 0.5-1 | 92.3 ± 7.7 | 18.2 ± 18.2 | 420 | −0.68 | 147 |
| 7 | 1 | 100 ± 0.0 | 21.0 ± 6.0 | 420 | −0.68 | 147 |
| 8 | 1 | 100 ± 0.0 | 21.0 ± 6.0 | 424 | 1.42 | 122 |
| 9 | 0.5-1 | 78.2 ± 21.8 | 23.3 ± 13.0 | 408 | 2.33 | 146 |
| 10 | 0.5 | 71.7 ± 2.7 | 31.7 ± 4.7 | 420 | −0.95 | 147 |
| 11 | 0.5-1 | 37.5 ± 11.2 | 0.0 ± 0.0 | 448 | 1.69 | 131 |
| 12 | 0.5-2 | 39.3 ± 9.4 | 20.8 ± 9.0 | 448 | 1.69 | 131 |
| 13 | 1 | 64.3 ± 10.7 | 17.9 ± 8.4 | 448 | 1.69 | 131 |
| 14 | 0.5-1 | 60.7 ± 7.1 | 27.6 ± 1.3 | 486 | 2.66 | 122 |
| 15 | 0.5-2 | 29.1 ± 17.7 | 13.9 ± 13.9 | 419 | 0.28 | 134 |
| 16 | 0.5-1 | 47.6 ± 5.1 | 13.2 ± 13.2 | 424 | 1.42 | 122 |
| 17 | 1 | 100 ± 0.0 | 27.6 ± 1.3 | 408 | 0.95 | 131 |
| 18 | 1 | 87.3 ± 12.7 | 28.4 ± 0.5 | 420 | −0.11 | 138 |
| 19 | 1-2 | 64.1 ± 10.5 | 18.3 ± 1.9 | 424 | 2.05 | 122 |
| 29 | 1 | 75.4 ± 1.7 | 22.8 ± 3.5 | 436 | 0.95 | 131 |
| 31 | 1 | 48.1 ± 12.4 | 10.1 ± 10.1 | 448 | 0.73 | 142 |

TABLE 6-continued

Activity of orally administered AR agonists (3 µmol/kg) in CCI model of neuropathic pain in mice

| Cmpd. | Time of peak protection (h) | Max. effect $E_{max}$ (% ± SEM) | Effect at 3 h (% ± SEM) | Mol. Wt. | cLogP[b] | tPSA (Å$^2$) |
|---|---|---|---|---|---|---|
| 32 | 0.5-3 | 93 ± 7 | 83 ± 11 | 459 | 2.17 | 122 |
| 33 | 1 | 87.4 ± 0.6 | 40.6 ± 8.1 | 458 | 2.33 | 131 |
| 34 | 1 | 62.4 ± 14.7 | 4.2 ± 4.2 | 436 | 1.90 | 131 |
| 37 | 0.5-3 | 94 ± 6 | 78 ± 3 | 526 | 1.42 | 122 |
| 100 | 1 | 100 ± 0.0 | 48.7 ± 0.0 | 503 | 2.32 | 122 |
| 101 | 1 | 49 | 12 | 425 | 0.12 | 134 |
| 300 | 1 | 40.8 ± 14.5 | 6.7 ± 6.7 | 419 | 0.28 | 134 |
| 400 | 0.5-1 | 44.1 ± 9.9 | 5.0 ± 5.0 | 418 | 1.77 | 122 |
| 200 | 1 | 100 ± 0 | 24 ± 11 | 565 | 4.15 | 122 |

[a]Effect shown for ipsilateral hind paw; there is no effect on the contralateral side.
[b]calculated using ChemDraw.

TABLE 7

Activity of orally administered AR agonists (3 µmol/kg) in CCI model of neuropathic pain in mice and physicochemical parameters.

| Compound Compd. | Time of peak protection (h) | Max. effect $E_{max}$ (% ± SEM)[a] | Effect at 3 h (% ± SEM) | MW (D) | cLogP[b] | tPSA (Å$^2$) |
|---|---|---|---|---|---|---|
| 100 | 1 h | 83 ± 5 | 22 ± 7 | 461 | 1.58 | 150 |
| 101 | 1 h | 69 ± 9 | 8 ± 8 | 496 | 2.04 | 150 |
| 102 | 1 h | 55 ± 6 | 8 ± 8 | 497 | 1.79 | 150 |
| 103 | 1 h | 55 ± 6 | 22 ± 7 | 462 | 0.29 | 162 |
| 104 | 1 h | 89 ± 11 | 39 ± 10 | 463 | −0.67 | 175 |
| 105 | 1 h | 78 ± 0 | 22 ± 7 | 463 | −0.67 | 175 |
| 106 | 1 h | 85 ± 5 | 22 ± 7 | 465 | −0.31 | 165 |
| 107 | 1 h | 65 ± 8 | 21 ± 7 | 451 | 0.96 | 159 |
| 108 | 1 h | 55 ± 6 | 8 ± 8 | 502 | 2.34 | 159 |
| 109 | 1 h | 67 ± 19 | 8 ± 7 | 502 | 2.19 | 150 |
| 110 | 1 h | 89 ± 11 | 8 ± 8 | 515 | 2.72 | 150 |
| 111 | 1 h | 69 ± 9 | 14 ± 2 | 546 | 2.34 | 150 |
| 112 | 1 h | 94.6 | 22 ± 7 | 569 | 1.22 | 165 |
| 125 | 0.5-3 | 100 | 90 | 542 | 3.10 | 150 |
| 120 | 0.5-4 | 100 | 100 | 612 | 4.35 | 150 |
| 121 | 0.5-3 | 90 | 80 | 592 | 4.29 | 150 |

[a]Effect shown for ipsilateral hind paw; there is no effect on the contralateral side.
[b]calculated using ChemBioDraw, v. 13.0.

The in vivo activity of various $N^6$-methyl derivatives were compared and correlated with structure. The unsubstituted C2-phenylethynyl analogue 400 (prior art) displayed low efficacy (~30% of full reversal at peak effect) in the CCI model of chronic neuropathic pain (NP). Substitution of the phenyl ring with methoxy improved the maximal effect (~70), but only in the ortho position in 13. All positions of nitrogen in the pyridyl analogues 401 (prior art), 300 and 15 resulted in the same low efficacy as the phenyl analogue 400. However, dinitrogen substitution in pyrazine 7 increased the efficacy to ~100%, but the efficacy of isomers containing nitrogen at different positions 6 and 10 resulted in less than full efficacy. The 2-furyl 17 and 2-thienyl 8 analogues were fully efficacious with ~3 h duration of action. Addition of chloro to thienyl analogue in compound 32 prolonged the duration of action while maintaining full efficacy. When the sulfur was present at a different position of the thienyl ring in 16, the efficacy was diminished. The ferrocene derivative 37 was fully efficacious. Cycloalkyl analogues 19 and 20 displayed less than full efficacy in vivo (60-70%). In summary, the analogues that reached full (~100% efficacy) in reversing NP in vivo were: 7, 18, 17, 8, 32, and 37.

Example 4

This example demonstrates the effect on intracellular cAMP levels in CHO cells exhibited by compounds in accordance with an embodiment of the invention.

Intracellular cAMP levels in CHO cells expressing the recombinant $hA_3AR$ were measured using an ELISA assay (Nordstedt et al., Anal. Biochem. 1990, 189, 231-234). Cells were first harvested by trypsinization. After centrifugation and resuspended in medium, cells were planted in 96-well plates in 0.1 mL medium. After 24 h, the medium was removed and cells were washed three times with 0.2 mL DMEM, containing 50 mM HEPES, pH 7.4. Cells were then treated with the agonist (1 μM 43 for $hA_3AR$) or test compound in the presence of rolipram (1 μM) and adenosine deaminase (3 units/mL). After 30 min forskolin (10 μM) was added to the medium, and incubation was continued for an additional 15 min. The reaction was terminated by removing the supernatant, and cells were lysed upon the addition of 100 μL of 0. μM ice-cold HCl. The cell lysate was resuspended and stored at $-20°$ C. For determination of cAMP production, 50 μL of the HCl solution was used in the Amersham cAMP Enzyme Immunoassay following the instructions provided with the kit. The results were interpreted using a SpectroMax M5 Microplate reader (Molecular Devices, Sunnyvale, Calif.) at 450 nm. The results for four representative embodiments, compounds 7 (MRS5914), 8 (MRS5917), 40 (MRS5918), and 41 (MRS5919 are illustrated in FIGS. 7A-7D, respectively.

Similar cAMP assays were conducted with HEK293 cells expressing the $mA_1AR$ or $mA_3AR$. HEK293 cells were detached from cell culture plates, resuspended in serum-free DMEM containing 25 mM HEPES (pH 7.4), 1 unit/ml adenosine deaminase, 4-(3-butoxy-4-methoxyphenyl)methyl-2-imidazolidone (Tocris, Ro 20,1724, 2 μM) and 300 nM 8-[4-[4-(4-chlorophenyl)piperazide-1-sulfonyl)phenyl]]-1-propylxanthine (Tocris, PSB603, 300 nM) inhibit $A_{2B}ARs$ expressed endogenously in HEK293 cells, and then transferred to polypropylene tubes ($2\times10^5$ cells/tube). The cells were co-incubated with forskolin (10 μM) and AR ligands for 15 min at 370° C. with shaking, after which the assays were terminated by adding 500 μL 1 N HCl. The lysates were centrifuged at 4000×g for 10 min. The cAMP concentration was determined in the supernatants using a competitive binding assay, as previously described.[59] $EC_{50}$ and $E_{max}$ values were calculated by fitting the data to: $E=E_{min}+(E_{max}-E_{min})/(1+10^{x-log\ EC50})$.

Example 5

This example demonstrates the lack of toxicity exhibited by MRS5698.

The structure of MRS5698 is illustrated in FIG. 6. MRS5698 was formulated in a vehicle comprising 40% PEG 300 and 10% solutol in 10% HP-β-CD in water. The formulation was dosed at up to 150 mg/kg by gavage to Sprague Dawley rats. No abnormal findings were observed at the high dose of 150 mg/kg. These results indicate that MRS5698 is highly $A_3$ specific in its in vivo action.

Example 6

This example demonstrates off-target interactions from binding experiments of compounds in accordance with an embodiment of the invention.

The receptors assayed are set forth in Table 5.

TABLE 5

| Muscarinic receptor | | | | | |
|---|---|---|---|---|---|
| hM1 | hM2 | hM3 | hM4 | hM5 | |
| Adrenergic receptor | | | | | |
| Alpha 1A | Alpha 1B | Alpha 1C | Alpha 2A | Alpha 2B | Alpha 2C |
| h Beta 1 | h Beta 2 | h Beta 3 | | | |
| Dopamine receptor | | | | | |
| hD1 | hD1 | rD3 | hD4 | hD5 | |
| GABA receptor | | | | | |
| rGABAa | | | | | |
| Histamine receptor | | | | | |
| hH1 | hH2 | hH3 | hH4 | | |
| Opiate receptor | | | | | |
| DOR | KOR | MOR | | | |
| Serotonin receptor | | | | | |
| h5HT1A | h5HT1B | h5HT1D | h5HT1E | h5HT1F | |
| h5HT2A | r5HT2A | h5HT2B | h5HT2C-INI | h5HT2C-VGI | |
| h5HT3 | h5HT4 | h5HT5A | h5HT6 | h5HT7 | |
| Transporters | | | | | |
| SERT | NET | DAT | | | |
| hBPZP | | | | | |
| r Sigma 1 | r Sigma 2 | | | | |

The compounds assayed were MRS5698 (prior art), MRS5676 (prior art), 7, 18, 17, 8, and 32. The results are set forth below. Key: Ki<1.0 μM +++; 1-10 μM ++; >10 μM +($K_i$ values, when known, are in parentheses).

MRS5698
$\alpha_{2C}$ ++(2.0 μM)
$\alpha_{2B}$ ++(2.9 μM)
$\alpha_{2B}$ ++(4.8 μM)
$\beta_3$ ++(5.8 μM)
$5HT_{1A}$ ++(7.6 μM)
$5HT_{2B}$ ++(2.6 μM)
$5HT_{2C}$ ++(5.8 μM)
$H_4$ ++(9.4 μM)
$M_2$ ++(5.4 μM)
DOR ++(2.5 μM)
$\sigma_2$ +++(0.91 μM)
PBR +++(0.34 μM)
No interactions at other receptors.
MRS5676
$\beta_3$ ++(3.0 μM)
$H_4$ ++(~10 μM)
$M_1$ ++(3.1 μM)
SERT ++(3.4 μM)

Radioligand binding at the dopamine transporter was ~7× enhanced by the compound at 10 μM.
No interactions at other receptors.
7
$\alpha_{1B}$ ++(9.4 μM)
$\alpha_{1D}$ ++(4.3 μM)
$\alpha_{2A}$ ++(7.9 μM)
$\alpha_{2C}$ ++(6.8 μM)
DAT ++(1.8 μM)
SERT +(>10 μM)
No interactions at other receptors.
18
No interactions (10 μM) at all alpha receptors, beta receptors, histamine, 5HT receptors, muscarinic receptors, dopamine receptors, BZP rat brain, SERT, NET, GABA-A, KOR, DOR, MOR, BZP. However PBR, Sigma-1, Sigma-2 showed weak interactions.
17
No interactions (10 μM) at all alpha receptors, beta receptors, histamine, 5HT receptors, muscarinic receptors, dopamine receptors, BZP rat brain, SERT, NET, GABA-A, KOR, DOR, MOR, BZP. However PBR, Sigma-1, Sigma-2 showed weak interactions.
8
$\alpha_{2B}$ ++(5.5 μM)
DAT +++(0.76 μM)
$D_2$ +(>10 μM)
No interactions at other receptors.
32
No interactions (10 μM) at all alpha receptors, beta receptors, histamine, 5HT receptors, muscarinic receptors, dopamine receptors, BZP rat brain, SERT, NET, GABA-A, KOR, DOR, MOR, BZP. However PBR, Sigma-1 ($K_i$ 1.4 μM), Sigma-2 ($K_i$ 0.63 μM) showed 60-70% inhibition at 10 μM. Radioligand binding at the dopamine transporter was ~5× enhanced by the compound at 10 μM.
101
No significant interactions (>50% at 10 μM).
37
Significant interactions (<10 μM) at 5HT2A, 5HT2B, 5HT2C, 5HT3, 5HT6, 5HT7, α2B, α2C, M1, M3, M4 and H1 receptors. Ki value at 5HT2C and 5HT3 receptors determined to be 0.277 and 2.62 μM, respectively. No significant interactions (>50% at 10 μM) at others.

As is apparent from the results set forth above, compounds 7, 18, 17, 8, 32, 101, and 37 exhibited significantly fewer off-target effects than did MRS5698 and MRS5676.

Example 7

In vitro stability parameters for selected compounds are set forth in Table 6, in accordance with an embodiment of the invention.

TABLE 6

| Test | Compound | | | | |
|---|---|---|---|---|---|
| | 7 | 17 | 32 | 100 | 37 |
| Aq. Solubility (pH 7.4, μg/mL) | >208 | >202 | 16.8 ± 1.1 | 15.6 ± 0.9 | 14.5 ± 1.0 |
| Stability in simulated fluids ($t_{1/2}$, min): | | | | | |
| Gastric | >480 | >480 | >480 | >480 | 46.5 |
| Intestinal | >480 | >480 | >480 | >480 | 174 |

TABLE 6-continued

| Test | Compound | | | | |
|---|---|---|---|---|---|
| | 7 | 17 | 32 | 100 | 37 |
| % Unbound in plasma: | | | | | |
| Human | 61.2 | 24.2 | 6.22 | 2.67 | 7.00 |
| Rat | 57.5 | 40.5 | 5.91 | 4.04 | 6.32 |
| Mouse | 59.1 | 50.2 | 6.40 | 2.75 | 4.85 |
| Inhibition of 5 CYP isozymes: IC50, μM | >10 | >10 | >10 | >7[b] | >9[c] |
| Stability in liver microsomes ($t_{1/2}$, min): | | | | | |
| Human | 236 | 145 | 230 | 205 | 3.66 |
| Rat | >145 | 140 | 128 | 91 | 6.64 |
| Mouse | >145 | 141 | 143 | 96 | 1.98 | a-mean (±SD, where given) for n = 3.
[b]% inhibition at 10 μM: 1A2, 15.0; 2C9, 24.2; 2C19, 34.0; 2D6, 57.5 (IC$_{50}$ 7.4 μM); 3A4, 3.1 (average of n = 2).
[c]% inhibition at 10 μM: 1A2, 30.5; 2C9, 17.2; 2C19, 18.1; 2D6, 20.5; 3A4, 51.6 (IC$_{50}$ 9.4 μM), (average of n = 2).
d-CL$_{int}$ values (μL/min/mg protein) in human liver microsomes: 7, 2.99; 17, 3.09; 32, 3.69; 100, 3.38.

Example 8

This example demonstrates the maximal tolerated dose of compound 32 in Sprague Dawley rats at a single dose in escalated dose levels (100 and 150 mg/kg, which is roughly 100-times a pharmacologically active dose), in accordance with an embodiment of the invention.

A total of eighteen rats (3 rats/sex/dose level) were used in the study. Dose levels tested were 100 and 150 mg/kg single dose via oral route followed by post dose two days observation period. The study was conducted in a staggered manner in three sets (3 rats/sex/dose level). Examined parameters to determine the maximum tolerated dose of compound 32 included: clinical observation, mortality, body weight, gross necropsy and organ weight.

There were no adverse clinical signs observed throughout the study duration. There were no significant changes observed in body weight as compared to animals of vehicle control group throughout the study duration.

There was no significant change in organ weights caused due to treatment with compound 32. There was no major change in organ to body weight ratio.

Example 9

This example demonstrates that compounds 7 and 8 are potent, full agonists of the A$_3$AR.

The activity in the inhibition of cyclic AMP formation at the human A$_1$AR and A$_3$AR were evaluated for compounds 7 and 8. The results are depicted graphically in FIGS. 9A (compound 7) and 9B (compound 8).

Example 10

This example demonstrates that compound 32 shows no acute liver toxicity at a high dose, in accordance with an embodiment of the invention.

Ten male C57BL/6J (6- to 8-week-old) mice were divided into a control group (n=5) and a compound 32-treated group (n=5). Compound 32 dissolved in corn oil was given by oral gavage at a dose of 50 mg/kg body weight, and control mice were treated with corn oil only. During a 24 h in vivo exposure to compound 32, the liver histology remained normal, and no alteration of GSH and GSSG levels in liver was observed. This indicates that there are no significant acute toxic effects due to potential GSH fluctuation resulting from the reaction of GSH and compound 32.

Example 11

This example demonstrates that compound 32 (MRS5980) and MRS5698 can reinstate the efficacy of morphine over a dosage period.

The chronic constriction injury (CCI) model as described in Example 3 was used. Morphine was given daily subcutaneous injections (0.2 ml volume) or a combination of morphine sulfate (10.5 μmol/kg/day)±MRS5698 or compound 32 (0.18 μmol/kg/day) or its vehicle (1% DMSO in saline) starting at day 7 and then continuing throughout day 25.

Behavioral measurements were taken on day 0 before surgery, on day 7 post surgery (time of peak pain) and then on alternate days. Testing was done 1 hour after drug injection since this represents the time of peak morphine's analgesia. Mechano-allodynia was assessed using the von Frey up and down method as described previously. Calibrated von Frey filaments [Stoelting, ranging from 2.83 (0.07 g) to 4.31 (2 g) bending force] were applied to the midplantar surface of the hindpaw (2). Data were expressed as % Reversal of mechano-allodynia at peak (1h post dosing). All animals were allowed to acclimate for ~15 min on an elevated mesh platform in an enclosure.

As seen in FIG. 14, s.c injection of morphine at day 7 (time of peak development of mechano-allodynia following constriction of the sciatic nerve in mice) causes near-to-maximal reversal of mechano-allodynia. However, morphine loses its ability to reverse mechano-allodynia when given daily over 25 days in nerve-injured rats typical of the well-known development of analgesic tolerance. However, morphine retained its ability to reverse neuropathic pain over this dosing period when injected together with doses of $A_3AR$ agonists (MRS5698; compound 32 (MRS5980)) that has no analgesic effects per se. These results suggest that an $A_3AR$ agonist can re-instate the opioid's efficacy during prolonged use by blocking analgesic tolerance; combination of an opioid/$A_3AR$ approach may allow for the long-term use of opioids without the need for dose-escalation anticipated to precipitate known unwanted side-effects. Such pharmacodynamic differences in analgesia are not explained by altered morphine pharmacokinetics with $A_3AR$ co-administration since plasma levels of morphine concentrations were similar in the presence of absence of the $A_3AR$ agonist.

Example 12

This example demonstrates the bioavailability of compound 32 (MRS5980) in the male SD rat.

Male SD rats were dosed intravenously at 1 mg/kg and orally at 1, 3, and 10 mg/kg. Plasma concentration as a function of time is depicted in FIG. 15. The bioavailabity data is set forth in Table 7.

TABLE 7

| | i.v. 1 mg/kg | p.o. 1 mg/kg | 3 mg/kg | 10 mg/kg |
|---|---|---|---|---|
| Bioavailability | | 22 ± 0.3 | 19 ± 3.5 | 33 ± 2.2 |
| $t_{1/2}$ (h) | 0.7 ± 0.3 | 3.6 ± 0.4 | 5.3 ± 0.8 | 7.8 ± 2.0 |
| $C_{max}$ | | | | |
| ng/ml | | 29 ± 8.6 | 47 ± 24 | 326 ± 57 |
| nM | | 63 ± 19 | 101 ± 53 | 711 ± 125 |

Example 13

This example demonstrates allosteric interactions with the dopamine transporter in binding assays, in accordance with an embodiment of the invention.

Some of the compounds interact allosterically with the dopamine transporter (DAT) in binding assays. For example, the effect of 10 μM MRS5980 is to enhance radioligand ([$^3$H]WIN35428) binding at the human DAT is to increase the level of binding by 556%. The effect of 10 μM MRS7135 is to enhance radioligand ([$^3$H]WIN35428) binding at the human DAT is to increase the level of binding by 329%.

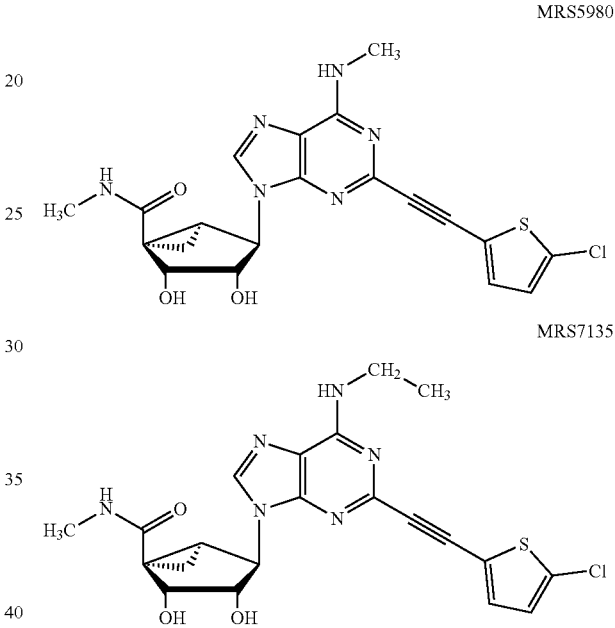

It has been discovered that the 1-deaza modification does not exhibit this off-target interaction. The 1-deaza equivalent of MRS5980 is MRS7140, and the 1-deaza equivalent of MRS7135 is MRS7144. MRS7140 has no effect on radioligand ([$^3$H]WIN35428) binding at the human DAT (1% inhibition). MRS7144 has a longer duration of action in chronic pain suppression than MRS7140 which may be associated with the $N^6$-ethyl group vs. the $N^6$-methyl group in this series.

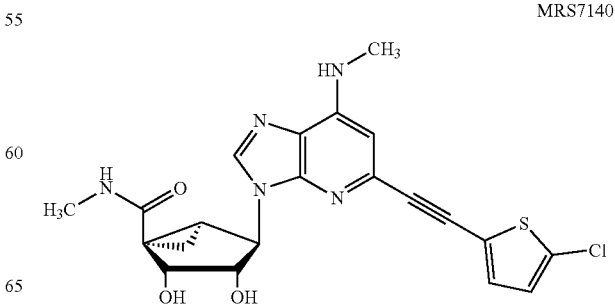

MRS7144

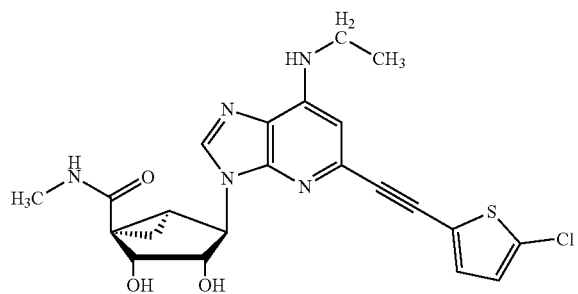

Therefore, the 1-deaza modification in this chemical series may be considered a general means of avoiding interaction with DAT.

Another approach to removing interaction with the DAT is to enlarge the $N^6$ substituent. As the $N^6$-methyl and $N^6$-ethyl derivatives (MRS5980 and MRS7135 above) interact with DAT, a similar $N^6$-(3-chlorobenzyl) derivative MRS5698 does not interact with DAT.

MRS5698

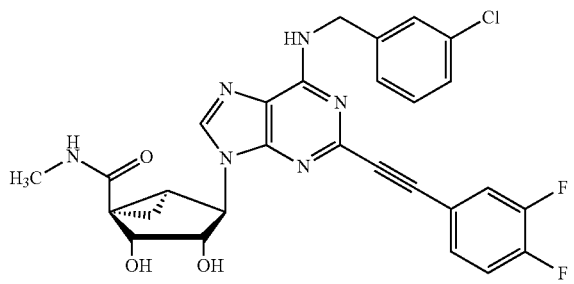

Therefore, the inclusion of larger $N^6$-alkyl, alkyl-aryl, and alkyl-cycloalkyl groups diminish this off-target interaction. Examples of such larger groups include $N^6$-cyclopropyl, $N^6$-cyclobutyl, $N^6$-cyclopropylmethyl, $N^6$-cyclobutylmethyl, and other straight and branched alkyl groups such as isobutyl.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for treating pain comprising administering to a subject in need thereof a therapeutically effective amount of a compound selected from:

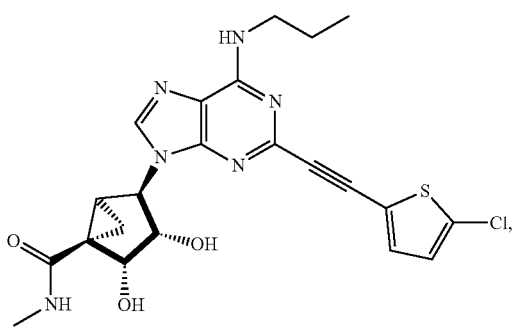

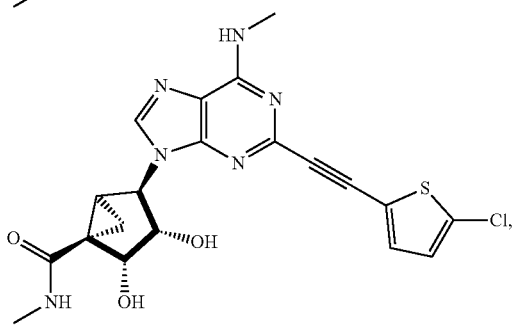

-continued

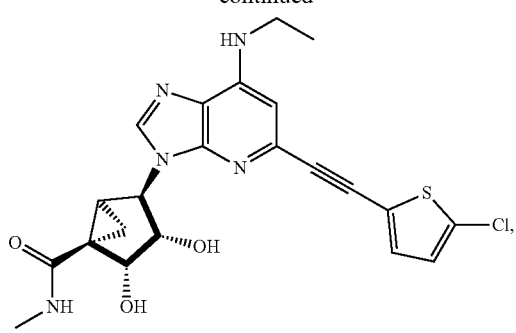

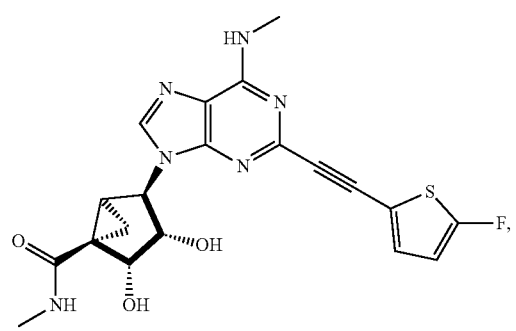

or a pharmaceutically acceptable salt of any one thereof.

2. The method of claim 1, wherein the compound administered is:

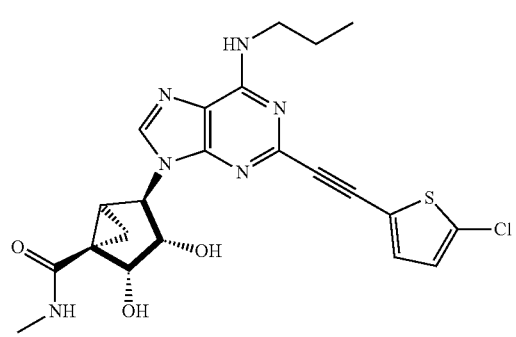

or a pharmaceutically acceptable salt thereof.

3. The method of claim 1, wherein the compound administered is:

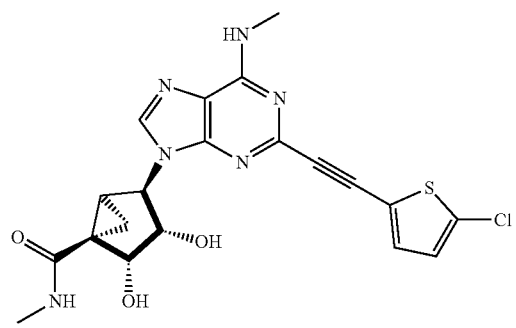

or a pharmaceutically acceptable salt thereof.

4. The method of claim 1, wherein the compound administered is:

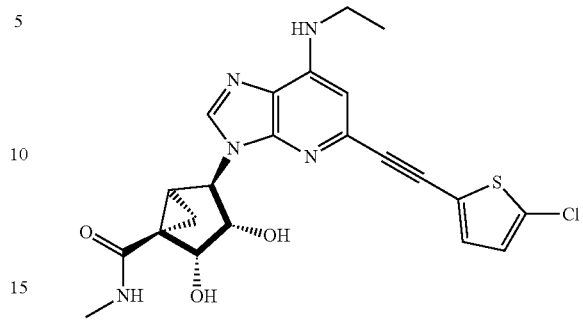

or a pharmaceutically acceptable salt thereof.

5. The method of claim 1, wherein the compound administered is:

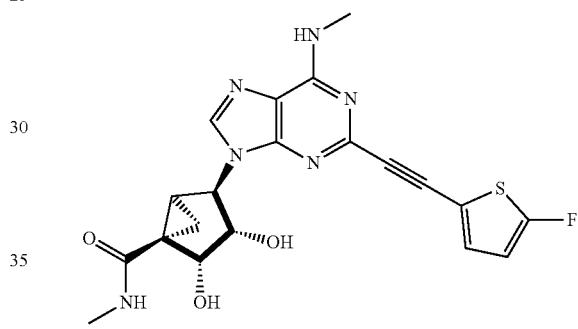

or a pharmaceutically acceptable salt thereof.

6. The method of claim 2, wherein the compound administered is:

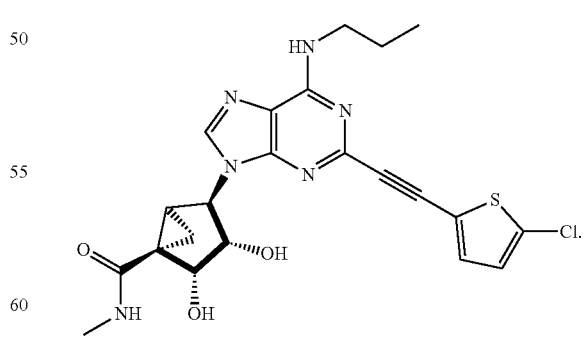

7. The method of claim 3, wherein the compound administered is:

8. The method of claim 4, wherein the compound administered is:
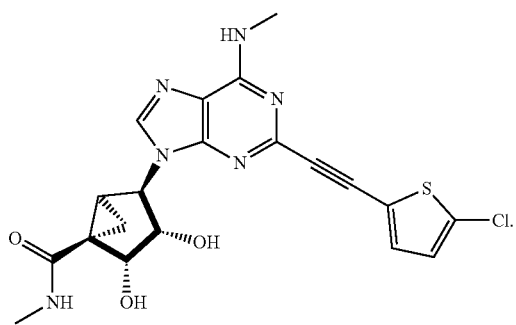
9. The method of claim 5, wherein the compound administered is:
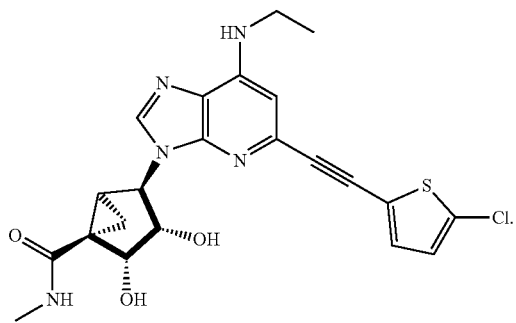
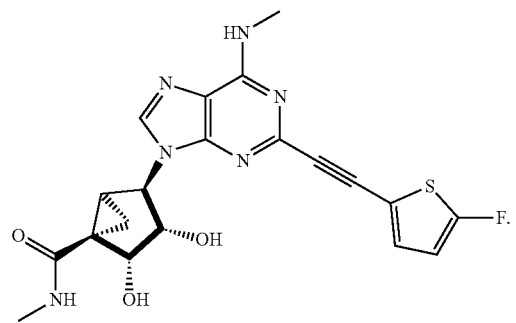
10. The method of claim 1, wherein the pain is neuropathic pain.
11. The method of claim 6, wherein the pain is neuropathic pain.
12. The method of claim 1, wherein the compound selected from:
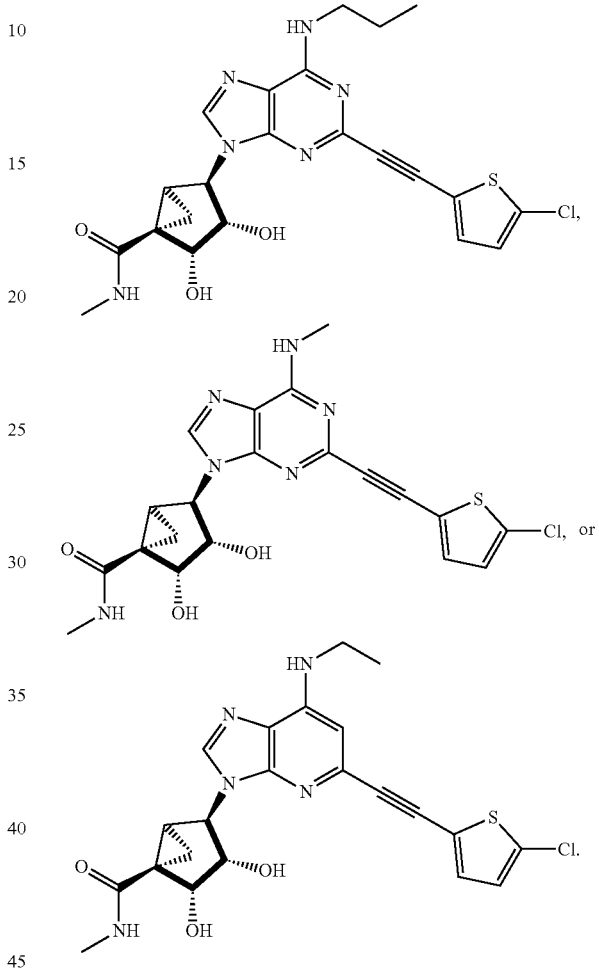
13. The method of claim 12, wherein the pain is neuropathic pain.
* * * * *

UNITED STATES PATENT AND TRADEMARK OFFICE
CERTIFICATE OF CORRECTION

PATENT NO. : 10,577,368 B2
APPLICATION NO. : 15/949701
DATED : March 3, 2020
INVENTOR(S) : Jacobson et al.

Page 1 of 1

It is certified that error appears in the above-identified patent and that said Letters Patent is hereby corrected as shown below:

Please amend Claim 12 as follows:

12. The method of claim 55, wherein the compound is selected from:

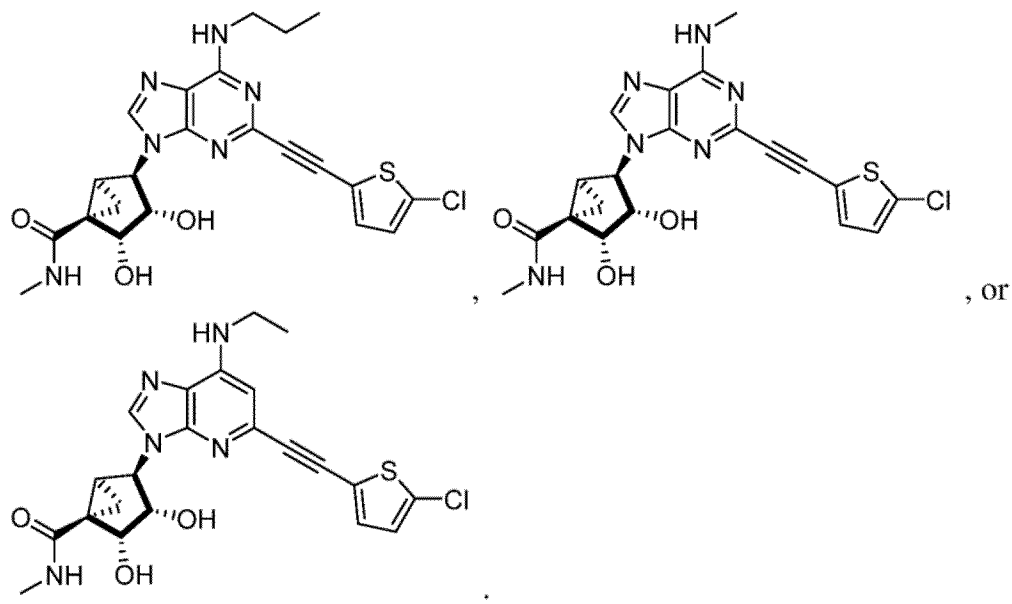

, or

Signed and Sealed this
Second Day of June, 2020

Andrei Iancu
*Director of the United States Patent and Trademark Office*